United States Patent
Krauss et al.

(10) Patent No.: US 6,479,663 B2
(45) Date of Patent: *Nov. 12, 2002

(54) INTERMEDIATES USEFUL FOR THE PREPARATION OF ANTIHISTAMINIC PIPERIDINE DERIVATIVES

(75) Inventors: Richard C. Krauss, Midland, MI (US); Robert M. Strom, Midland, MI (US); Carey L. Scortichini, Sanford, MI (US); William J. Kruper, Sanford, MI (US); Richard A. Wolf, Midland, MI (US); Weishi W. Wu, Midland, MI (US); Albert A. Carr, Cincinnati, OH (US); David A. Hay, Cincinnati, OH (US); Duane E. Rudisill, West Chester, OH (US); Gianbattista Panzone, Cornaredo (IT)

(73) Assignee: Merrell Pharmaceuticals Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/726,625

(22) Filed: Dec. 1, 2000

(65) Prior Publication Data

US 2001/0000038 A1 Mar. 15, 2001

Related U.S. Application Data

(60) Division of application No. 08/275,685, filed on Jul. 14, 1994, now Pat. No. 6,242,606, which is a continuation-in-part of application No. 08/237,466, filed on May 11, 1994, now abandoned, which is a continuation-in-part of application No. 08/144,084, filed on Oct. 27, 1993, now abandoned, which is a continuation-in-part of application No. 08/082,693, filed on Jun. 25, 1993, now abandoned.

(51) Int. Cl.[7] .......................... C07D 211/14

(52) U.S. Cl. .................. 546/239; 546/240

(58) Field of Search ............... 546/239, 240

(56) References Cited

U.S. PATENT DOCUMENTS

| | | | |
|---|---|---|---|
| 3,687,956 A | 8/1972 | Zivkovic | 546/240 |
| 3,806,526 A | 4/1974 | Carr et al. | 546/190 |
| 3,829,433 A | 8/1974 | Carr et al. | 546/232 |

(List continued on next page.)

FOREIGN PATENT DOCUMENTS

| | | |
|---|---|---|
| AU | 3860893 | 8/1978 |
| AU | 2015088 | 2/1989 |
| CA | 2117892 | 10/1993 |
| EP | 0399414 | 11/1990 |
| JP | 087193 | 7/1977 |
| JP | 008081 | 1/1983 |
| JP | 115547 | 6/1985 |

OTHER PUBLICATIONS

Green et al, Protecting Groups in Organic Synthesis, Wiley & Sons, pp. 224–228, 270–271 (1991).
Sekuur et al, CA 66:15320 (1966).
Paulus et al, CA 84:121876 (1975).
Sundberg et al, CA 110:23789 (1988).
Carr et al, CA 94:156759 (1980).
Young et al, CA 120:253379 (1994).
Muro et al, CA 88:50648 (1977).
Muro et al, CA 85:78127 (1976).
Yurchenko, CA 86:155751 (1977).
Santilli et al, CA 101:151836 (1984).
Routsalainen, CA 73:13984 (1970).
Yusupov, CA 125:195092 (1996).

(List continued on next page.)

Primary Examiner—Ceila Chang
(74) Attorney, Agent, or Firm—Morgan, Lewis & Bockius LLP

(57) ABSTRACT

The present invention is related to a novel intermediates and processes which are useful in the preparation of certain antihistaminic piperidine derivatives of the formula

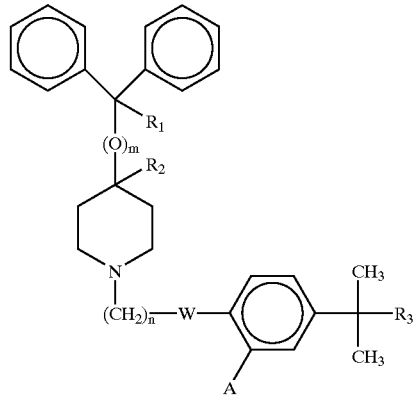

wherein
W represents —C(=O)— or —CH(OH)—;
$R_1$ represents hydrogen or hydroxy;
$R_2$ represents hydrogen;
$R_1$ and $R_2$ taken together form a second bond between the carbon atoms bearing $R_1$ and $R_2$;
n is an integer of from 1 to 5;
m is an integer 0 or 1;
$R_3$ is —COOH or —COOalkyl wherein the alkyl moiety has from 1 to 6 carbon atoms and is straight or branched
each of A is hydrogen or hydroxy; and
pharmaceutically acceptable salts and individual optical isomers thereof,
with the proviso that where $R_1$ and $R_2$ are taken together to form a second bond between the carbon atoms bearing $R_1$ and $R_2$ or where $R_1$ represented hydroxy m is an integer 0.

2 Claims, No Drawings

U.S. PATENT DOCUMENTS

| | | | | |
|---|---|---|---|---|
| 3,839,431 | A | 10/1974 | Sheehan et al. | 562/461 |
| 3,862,173 | A | 1/1975 | Carr et al. | 546/213 |
| 3,878,217 | A | 4/1975 | Carr et al. | 546/191 |
| 3,898,271 | A | 8/1975 | Sheehan et al. | 560/57 |
| 3,922,276 | A | 11/1975 | Duncan, Jr. et al. | 546/226 |
| 3,931,197 | A | 1/1976 | Carr et al. | 546/237 |
| 3,941,795 | A | 3/1976 | Carr et al. | 546/240 |
| 3,946,022 | A | 3/1976 | Carr et al. | 546/191 |
| 3,956,296 | A | 5/1976 | Duncan, Jr. et al. | 544/130 |
| 3,965,257 | A | 6/1976 | Carr et al. | 424/45 |
| 3,978,071 | A | 8/1976 | Nakanishi et al. | 546/121 |
| 4,028,404 | A | 6/1977 | Bays et al. | 514/570 |
| 4,105,790 | A | 8/1978 | Hughes et al. | 514/541 |
| 4,254,129 | A | 3/1981 | Carr et al. | 514/317 |
| 4,254,130 | A | 3/1981 | Carr et al. | 514/317 |
| 4,285,957 | A | 8/1981 | Carr et al. | 514/317 |
| 4,285,958 | A | 8/1981 | Carr et al. | 514/317 |
| 4,381,398 | A | 4/1983 | Takizawa et al. | 549/360 |
| 4,407,823 | A | 10/1983 | Kirsch et al. | 514/569 |
| 4,434,182 | A | 2/1984 | Cruickshank et al. | 514/640 |
| 4,452,985 | A | 6/1984 | Santilli et al. | 548/131 |
| 4,550,116 | A | 10/1985 | Soto et al. | 514/327 |
| 4,686,018 | A | 8/1987 | Chaussard et al. | 204/59 |
| 4,742,175 | A | 5/1988 | Fawcett et al. | 546/241 |
| 4,990,658 | A | 2/1991 | Stahly et al. | 562/406 |
| 5,153,207 | A | 10/1992 | Ito et al. | 514/327 |
| 5,214,047 | A | 5/1993 | Ostersehit et al. | 514/257 |
| 5,581,011 | A | 12/1996 | D'Ambra | 560/8 |
| 5,750,703 | A | 5/1998 | D'Ambra | 546/240 |

OTHER PUBLICATIONS

D. McTavish et al, Drugs, 29:552 (1990).
Kingsolving et al, Pharmacologist, 15:221 (1973).
Woodward et al, Arzneim–Forsh, 32:1154 (1982).
Mann et al, Clin Pharm, 6:331 (1989).
Tetrahedron Letters, 11:809 (1976).
Roche et al, Sulfur Lett., 15(3):127–133 (1992).
Kimura et al, J. Am. Chem. Soc., 116(9):4087–8 (1994).
Gonzales et al, Heterocycles, 34(7):1311–15 (1992).
Okamoto et al, Bull. Chem. Soc. Jpn., 65(6):1731–3 (1992).
Itoh et al, Bull. Chem. Soc. Jpn., 64(10):2965–77 (1991).
Kalyanam et al, J. Chem. Soc., Chem. Commun., 13:1028–9 (1987).
Shridhar et al, Indian J. Chem., Sect. B, 21B(6):602–4 (1982).
Masuoka et al, Physiol. Chem. Phys., 13(2):145–52 (1981).
Uchida et al, Chem. Pharm. Bull., 37(4):958–61 (1989).
Madesclaire et al, Synthesis, 10:828–9 (1981).
Colah et al, Bull. Haffkine Inst., 5(1):20–2 (1977).
Sundberg et al, J. Heterocycl. Chem., 25(1):129–37 (1988).
Gyongyi et al, J. Chem. Res., 5:155 (1978).
Boyer et al, Synthesis, 12:980–1 (1988).
Ruotsalainen et al, Suom. Kemistilehti B., 43(2):91–7 (1970).
Khalaf et al, Bull. Soc. Chim. Fr., pp. 285–91 (1984).
Heidbuchel et al, Bull. Soc. Chim. Belg., 77(304):149–52 (1968).
Shridhar et al, Indian J. Chem., Sect. B, 22B(3):297–9 (1983).
Kim et al, Synth. Commun., 20(11):1625–29 (1990).
McPherson et al, J. Labelled Compound. Radiopharm., 28(8):877–99 (1990).
Kane et al, J. Heterocycl. Chem., 25(5):1471–4 (1988).
Archiv der Pharmazie, 306:807–813 (1973).
Morrison et al, Organic Chemistry, Allyn & Bacon Inc., p. 528 (1973).
Jaeu et al, Synthesis of the enantiomers of reduced haloperidol, CA 115(15); 158935m (1991).
J. Pharm. Biomed. Anal., 9(10–12):929–33 (1991).
Tetrahedron, 34:1651–1660 (1978).
Journal of Organic Chemistry, 50(25):5446–5448 (1985).
Journal of the Chemical Society, Dalton Trans., 1091–1097 (1982).
Burger, A Guide to the Chemical Basis fo Drug Design, p. 15.
J. Amer. Chem. Soc., 91(11):3028–34.
J. of Organic Chem., 52:2033–36 (1987).
J. of Applied Electrochem., 18:109 (1988).
Tetrahedron Letters, 33(43):6499–6502 (1992).
J. of Medicinal Chem., 16(5):487–490 (1973).
J. of Organic Chem., 31:1090–93 (1966).
j. of Organic Chem., 29:2490–91 (1964).
J. of Organic Chem., 236:2773–6 (1971).
Fuson et al, Reaction sof Mesityl Cyclopropyl and Propenyl Ketons, pp. 3255–3257 (Oct. 1948).
Greene, Protective groups in organic synthesis, Wiley & Sons, pp. 155, 189, 190 (1982).
Bohlmann et al, Tetrahedron Letters, 33:3683–84 (1968).
Schaal et al, Bull. Soc. Chim. FR 8:3064–70 (1971).

INTERMEDIATES USEFUL FOR THE PREPARATION OF ANTIHISTAMINIC PIPERIDINE DERIVATIVES

This is a divisional of application Ser. No. 08/275,685 filed Jul. 14, 1994 now U.S. Pat. No. 6,242,606, which is a Continuation-In-Part Application of Patent application Ser. No. 08/237,466, filed May 11, 1994 now abandoned which is a Continuation-In-Part Application of patent application Ser. No.08/144,084, filed Oct. 27, 1993 now abandoned which is a Continuation-In-Part Application of patent application Ser. No. 08/082,693, filed Jun. 25, 1993 now abandoned.

BACKGROUND OF THE INVENTION

The present invention is related to novel intermediates which are useful in the preparation of certain piperidine derivatives which are useful as antihistamines, antiallergy agents and bronchodilators [U.S. Pat. No. 4,254,129, Mar. 3, 1981, U.S. Pat. No. 4,254,130, Mar. 3, 1981, U.S. Pat. No. 4,285,958, Apr. 25, 1981 and U.S. Pat. No. 4,550,116, Oct. 29, 1985].

These antihistaminic piperidine derivatives can be described by the following formula:

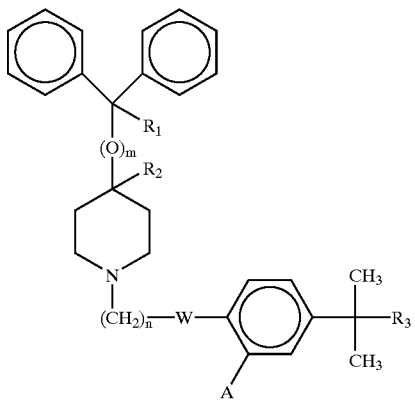

(I)

wherein

W represents —C(=O)— or —CH(OH)—;

$R_1$ represents hydrogen or hydroxy;

$R_2$ represents hydrogen;

$R_1$ and $R_2$ taken together form a second bond between the carbon atoms bearing $R_1$ and $R_2$;

n is an integer of from 1 to 5;

m is an integer 0 or 1;

$R_3$ is —COOH or —COOalkyl wherein the alkyl moiety has from 1 to 6 carbon atoms and is straight or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0.

SUMMARY OF THE INVENTION

The present invention provides novel intermediates useful for the preparation of certain antihistaminic piperidine derivatives of formula (I)

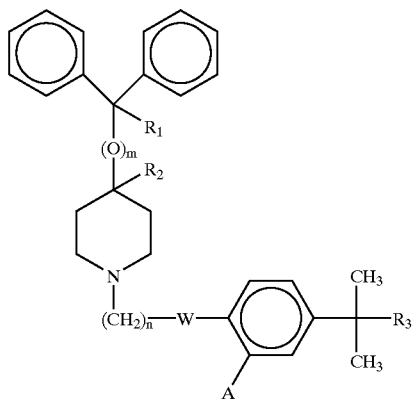

(I)

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_3$ is —COOH or —COOalkyl wherein the alkyl moiety has from 1 to 6 carbon atoms and is straight or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0.

These novel intermediates are described by the following formulas:

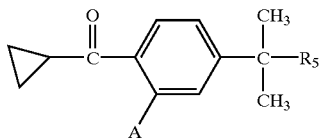

(II)

wherein

A is a hydrogen or hydroxy; and $R_5$ is H, —CH$_2$OD wherein D is hydrogen, acetate or benzoate, —CHO, Br, Cl, I, CN, —COOH, —COOalkyl or —CONR$_6$R$_7$ wherein the alkyl moiety has from 1 to 6 carbon atoms and is straight or branched and $R_6$ and $R_7$ are each independently H, $C_1$–$C_6$alkyl, $C_1$–$C_6$alkoxy or $R_6$ and $R_7$ taken together with the nitrogen atom form a pyrrolidine, piperidine or morpholine, with the proviso that $R_6$ and $R_7$ cannot both be represented by $C_1$–$C_6$alkoxy.

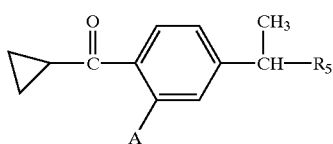
(III)

wherein
A is a hydrogen or hydroxy; and
R$_5$ is H, Br, Cl, I, CN, —COOH, —COOalkyl or —CONR$_6$R$_7$ wherein the alkyl moiety has from 1 to 6 carbon atoms and is straight or branched and R$_6$ and R$_7$ are each independently H, C$_1$–C$_6$alkyl, C$_1$–C$_6$alkoxy or R$_6$ and R$_7$ taken together with the nitrogen atom form a pyrrolidine, piperidine or morpholine, with the proviso that R$_6$ and R$_7$ cannot both be represented by C$_1$–C$_6$alkoxy.

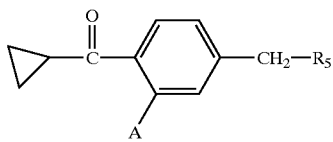
(IV)

wherein
A is a hydrogen or hydroxy; and
R$_5$ is H, Br, Cl, I, CN, —COOH, —COOalkyl or —CONR$_6$R$_7$ wherein the alkyl moiety has from 1 to 6 carbon atoms and is straight or branched and R$_6$ and R$_7$ are each independently H, C$_1$–C$_6$alkyl, C$_1$–C$_6$alkoxy or R$_6$ and R$_7$ taken together with the nitrogen atom form a pyrrolidine, piperidine or morpholine, with the proviso that R$_6$ and R$_7$ cannot both be represented by C$_1$–C$_6$alkoxy.

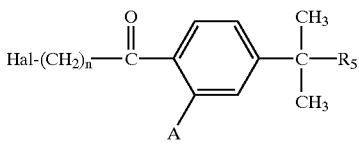
(V)

wherein
Hal is Cl, Br or I;
n is an integer of from 1 to 5;
A is a hydrogen or hydroxy; and
R$_5$ is H, CH$_2$OD wherein D is hydrogen, acetate or benzoate, CHO, Br, Cl, I, CN, —COOH or —CONR$_6$R$_7$ wherein R$_6$ and R$_7$ are each independently H, C$_1$–C$_6$alkyl, C$_1$–C$_6$alkoxy or R$_6$ and R$_7$ taken together with the nitrogen atom form a pyrrolidine, piperidine or morpholine, with the proviso that R$_6$ and R$^7$ cannot both be represented by C$_1$–C$_6$alkoxy.

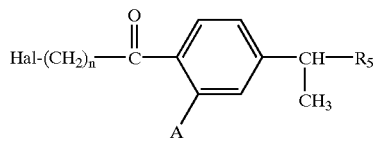
(VI)

wherein
Hal is Cl, Br or I;
n is an integer of from 1 to 5;
A is a hydrogen or hydroxy; and
R$_5$ is H, Br, Cl, I, CN, —COOH,—COOalkyl or —CONR$_6$R$_7$ wherein the alkyl moiety has from 1 to 6 carbonatoms and is straight or branched and R$_6$ and R$_7$ are each independently H, C$_1$–C$_6$alkyl, C$_1$–C$_6$alkoxy or R$_6$ and R$_7$ taken together with the nitrogen atom form a pyrrolidine, piperidine or morpholine, with the proviso that R$_6$ and R$_7$ cannot both be represented by C$_1$–C$_6$alkoxy.

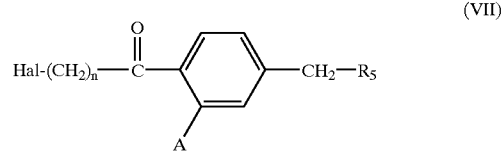
(VII)

wherein
Hal is Cl, Br or I;
n is an integer of from 1 to 5;
A is a hydrogen or hydroxy;
R$_5$ is H, Br, Cl, I, CN, —COOH, —COOalkyl or —CONR$_6$R$_7$ wherein the alkyl moiety has from 1 to 6 carbon atoms and is straight or branched and R$_6$ and R$_7$ are each independently H, C$_1$–C$_6$alkyl, C$_1$–C$_6$alkoxy or R$_6$ and R$_7$ taken together with the nitrogen atom form a pyrrolidine, piperidine or morpholine, with the proviso that R$_6$ and R$_7$ cannot both be represented by C$_1$–C$_6$alkoxy.

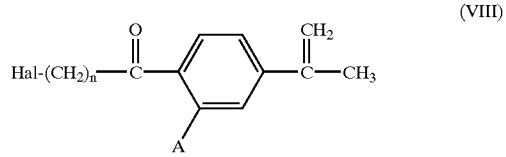
(VIII)

wherein
Hal is Cl, Br or I;
n is an integer of from 1 to 5; and
A is a hydrogen or hydroxy.

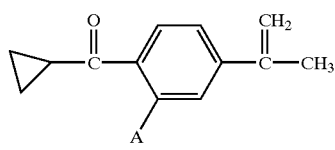
(IX)

wherein A is a hydrogen or hydroxy.

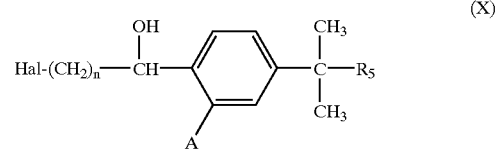
(X)

wherein
Hal is Cl, Br or I;
n is an integer of from 1 to 5;
A is a hydrogen or hydroxy; and
R$_5$ is H, CH$_2$OD wherein D is hydrogen, acetate or benzoate, CHO, Br, Cl, I, CN, —COOH, —Cooalkyl or —CONR$_6$R$_7$ wherein the alkyl moiety has from 1 to 6 carbon atoms and is straight or branched and $R_6$ and $R_7$ are each independently H, $C_1$–$C_6$alkyl, $C_1$–$C_6$alkoxy or $R_6$ and $R_7$ taken together with the nitrogen atom form a pyrrolidine, piperidine or morpholine, with the proviso that $R_6$ and $R_7$ cannot both be represented by $C_1$–$C_6$alkoxy; and individual optical isomers thereof.

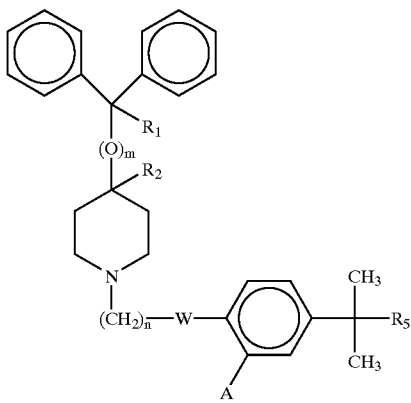

(XI)

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_5$ is H, Br, Cl, I, CN or —CONR$_6$R$_7$ wherein $R_6$ and $R_7$ are each independently H, $C_1$–$C_6$alkyl, $C_1$–$C_6$alkoxy or $R_6$ and $R_7$ taken together with the nitrogen atom form a pyrrolidine, piperidine or morpholine, with the proviso that $R_6$ and $R_7$ cannot both be represented by $C_1$–$C_6$alkoxy;

A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0.

In addition, the present invention provides novel processes for preparing the antihistaminic piperidine derivatives of formula

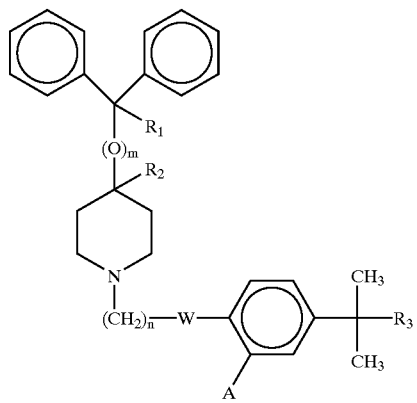

(I)

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_3$ is —COOH or —COOalkyl wherein the alkyl moiety has from 1 to 6 carbon atoms and is straight or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0, comprising the steps of:

(a) reacting a cumene compound of the formula

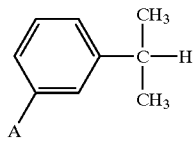

wherein A is as defined above with a ω-halo compound of the formula

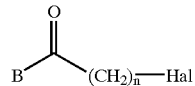

wherein B is halo or hydroxy, Hal represents Cl, Br or I and n is as defined above, in the presence of a suitable Lewis acid to produce a ω-halo cumylketone compound;

(b) reacting the ω-halo cumylketone compound with a suitable halogenating agent to give a ω-halo-halocumylketone compound;

(c) reacting the ω-halo-halocumylketone compound compound with a suitable cyanating agent to give a ω-halo-cyanocumylketone compound;

(d) reacting the ω-halo-cyanocumylketone compound with an appropriate straight or branched $C_1$–$C_6$ alcohol in the presence of a suitable anhydrous acid to give a ω'-halo-α'-keto-α,α-dimethylphenylacetic acid imidate compound;

(e) reacting the ω'-halo-α'-keto-α,αdimethylphenylacetic acid imidate compound with water to give a ω'-halo-α'-keto-α,α-dimethylphenylacetic acid ester compound;

(f) reacting the ω'-halo-α'-keto-α,α-dimethylphenylacetic acid ester compound with a piperidine compound of the formula

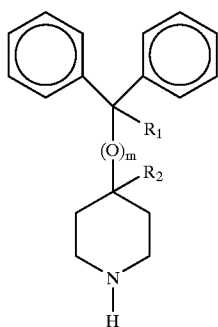

wherein $R_1$, $R_2$ and m are as defined above in the presence of a suitable non-nucleophilic base to produce a ω'-piperidine-α'-keto-α,α-dimethylphenyl derivative of formula (I) wherein $R_3$ is COOalkyl and W is —C(=O)—;

(g) optionally hydrolyzing the ω'-piperidine-α'-keto-α,α-dimethylphenyl derivative of formula (I) wherein $R_3$ is COOalkyl and W is —C(=O)— to produce a ω'-piperidine-α'-hydroxy-α,α-dimethylphenyl derivative of formula (I) wherein $R_3$ is COOH and W is —C(=O)—;

(h) optionally reacting the ω'-piperidine-α'-keto-α,α-dimethylphenyl derivative of formula (I) wherein $R_3$ is COOalkyl and W is —C(=O)— or the ω'-piperidine-α'-keto-α,α-dimethylphenyl derivative of formula (I) wherein $R_3$ is COOH and W is —C(=O)— with a suitable reducing agent to produce a ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)—; and (i) optionally reacting the ω'-piperidine-α'-hydroxy-α,α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl and W is —CH(OH)— or a ω'-piperidine-α'-keto-α,α-dimethylphenyl derivative wherein $R_3$ is —COOalkyl and W is —C(=O)—; and (j) optionally reacting the ω'-piperidine-α'-keto-α,α-dimethylphenyl derivative of formula (I) wherein $R_3$ is —COOH and W is —C(=O)—, the ω'-piperidine-α'-keto-α,α-dimethylphenyl derivative of formula (I) wherein $R_3$ is —COOalkyl and W is —C(=O)—, the ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)— with an appropriate deprotecting reagent, with the proviso that each of the hydroxy groups present in the compounds described in steps a-i are optionally protected or unprotected.

In addition, the present invention provides novel processes for preparing the antihistaminic piperidine derivatives of formula

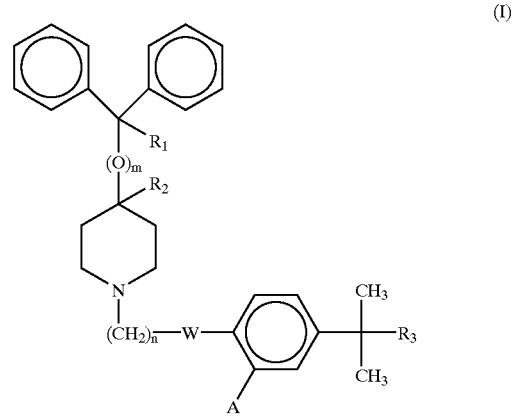

(I)

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_3$ is —COOH or —COOalkyl wherein the alkyl moiety has from 1 to 6 carbon atoms and is straight or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0, comprising the steps of:

(a) reacting a ω-halo-halocumylketone compound with carbon dioxide under electrochemical reduction conditions to give a ω'-halo-α'-keto-α,α-dimethylphenylacetic compound;

(b) reacting the ω'-halo-α'-keto-α,α-dimethylphenylacetic compound compound with an appropriate straight or branched $C_1$–$C_6$ alcohol in the presence of a suitable anhydrous acid to give a ω'-halo-α'-keto-α,α-dimethylphenylacetic acid ester compound;

(c) reacting the ω'-halo-α'-keto-α,α-dimethylphenylacetic acid ester compound with a piperidine compound of the formula wherein $R_1$, $R_2$ and m are as defined above in the presence of a suitable non-nucleophilic base to produce a ω'-piperidine-α'-keto-α,α-dimethylphenyl derivative of formula (I) wherein $R_3$ is COOalkyl and W=—C(=O)—;

(d) optionally hydrolyzing the ω'-piperidine-α'-keto-α,α-dimethylphenyl derivative of formula (I) wherein $R_3$ is

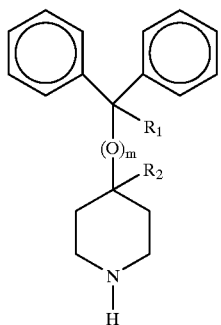

COOalkyl and W is —C(=O)— to produce a ω'-piperidine-α'-keto-α,α-dimethylphenyl derivative of formula (I) wherein $R_3$ is COOH and W is —C(=O)—;

(e) optionally reacting the ω'-piperidine-α'-keto-α,α-dimethylphenyl derivative of formula (I) wherein $R_3$ is COOalkyl and W is —C(=O)— or the ω'-piperidine-α'-keto-α,α-dimethylphenyl derivative of formula (I) wherein $R_3$ is COOH and W is —C(=O)— with a suitable reducing agent to produce a ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)—; and (f) optionally reacting the ω'-piperidine-α'-hydroxy-α,α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl and W is —CH(OH)— or ω'-piperidine-α'-keto-α,α-dimethylphenyl derivative of formula (I) wherein $R_3$ is —COOalkyl and W is —C(=O)—; and (g) optionally reacting the ω'-piperidine-α'-keto-α,α-dimethylphenyl derivative of formula (I) wherein $R_3$ is —COOH and W is —C(=O)—, the ω'-piperidine-α'-keto-α,α-dimethylphenyl derivative of formula (I) wherein $R_3$ is —COOalkyl and W is —C(=O)—, the ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)— with an appropriate deprotecting reagent, with the proviso that each of the hydroxy groups present in the compounds described in steps a–f are optionally protected or unprotected.

In addition, the present invention provides novel processes for preparing the antihistaminic piperidine derivatives of formula

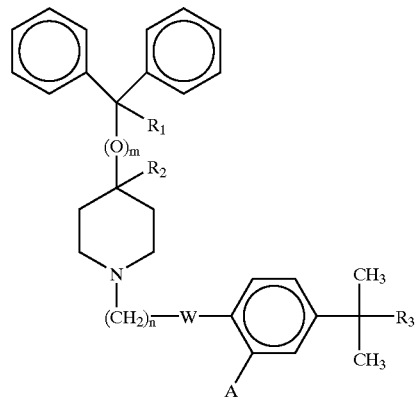

(I)

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer 3;

m is an integer 0 or 1;

$R_3$ is —COOH or —COOalkyl wherein the alkyl moiety has from 1 to 6 carbon atoms and is straight or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0, comprising the steps of:

(a) reacting a cumyl compound of the formula

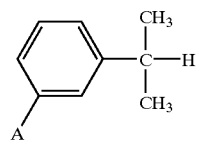

wherein A is as defined above with an appropriate cyclopropyl compound of the structure

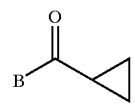

wherein B is halo or hydroxy, in the presence of a suitable Lewis acid to produce a cyclopropyl cumylketone compound;

(b) reacting the cyclopropyl cumylketone compound with a suitable halogenating agent to give a cyclopropyl halocumylketone compound;

(c) reacting the cyclopropyl halocumylketone compound with carbon dioxide under electrochemical reduction conditions to give a cyclopropylketo-α,α-dimethylphenylacetic acid compound;

(d) reacting the cyclopropylketo-α,α-dimethylphenylacetic with an appropriate straight or branched $C_1$–$C_6$ alcohol in the presence of a suitable anhydrous acid to give a ω'-halo-α'-keto-α,α-dimethylphenylacetic acid ester compound;

(e) reacting the ω'-halo-α'-keto-α,α-dimethylphenylacetic acid ester compound with a piperidine compound of the formula

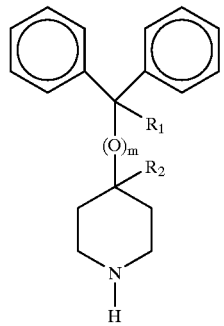

wherein $R_1$, $R_2$ and m are as defined above in the presence of a suitable non-nucleophilic base to produce a ω'-piperidine-α'-keto-α,α-dimethylphenyl derivative of formula (I) wherein $R_3$ is COOalkyl and W=—C(=O)—;

(f) optionally hydrolyzing the ω'-piperidine-α'-keto-α,α-dimethylphenyl derivative of formula (I) wherein $R_3$ is COOalkyl and W is —C(=O)— to produce a ω'-piperidine-α'-keto-α,α-dimethylphenyl derivative of formula (I) wherein $R_3$ is COOH and W is —C(=O)—;

(g) optionally reacting the ω'-piperidine-α'-keto-α,α-dimethylphenyl derivative of formula (I) wherein $R_3$ is COOalkyl and W is —C(=O)— or the ω'-piperidine-α'-keto-α,α-dimethylphenyl derivative of formula (I) wherein $R_3$ is COOH and W is —C(=O)— with a suitable reducing agent to produce a ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)—; and (h) optionally reacting the ω'-piperidine-α'-hydroxy-α,α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl and W is —CH(OH)— or a ω'-piperidine-α'-keto-α,α-dimethylphenyl derivative of formula (I) wherein $R_3$ is —COOalkyl and W is —C(=O)—; and (i) optionally reacting the ω'-piperidine-α'-keto-α,α-dimethylphenyl derivative of formula (I) wherein $R_3$ is —COOH and W is —C(=O)—, the ω'-piperidine-α'-keto-α,α-dimethylphenyl derivative of formula (I) wherein $R_3$ is —COOalkyl and W is —C(=O)—, the ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)— with an appropriate deprotecting reagent, with the proviso that each of the hydroxy groups present in the compounds described in steps a–h are optionally protected or unprotected.

Another embodiment of the present invention involves a process for preparing the piperidine derivatives of formula (I)

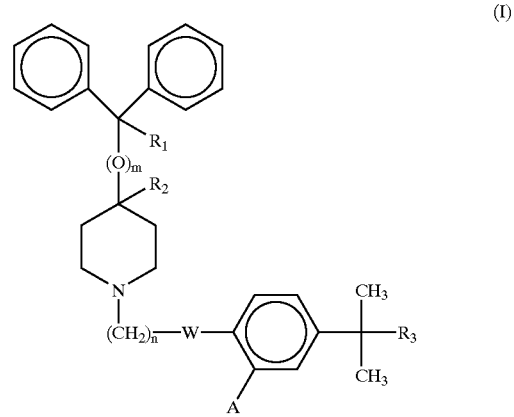

wherein
W represents —C(=O)— or —CH(OH)—;
$R_1$ represents hydrogen or hydroxy;
$R_2$ represents hydrogen; or
$R_1$ and $R_2$ taken together form a second bond between the carbon atoms bearing $R_1$ and $R_2$;
n is an integer of from 1 to 5;
m is an integer 0 or 1;
$R_3$ is —COOH or —COOalkyl wherein the alkyl moiety has from 1 to 6 carbon atoms and is straight or branched;
each of A is hydrogen or hydroxy; and
pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0, comprising the steps of:

(a) reacting α,α-dimethylphenylacetic acid amide compound of the formula

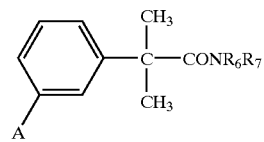

wherein A is as defined above and $R_6$ and $R_7$ are each independently H, $C_1$–$C_6$alkyl, $C_1$–$C_6$alkoxy or $R_6$ and $R_7$ taken together with the nitrogen atom for a pyrrolidine, piperidine or morpholine, with the proviso that $R_6$ and $R_7$ cannot both be represented by $C_1$–$C_6$alkyl with a ω-halo compound of the formula

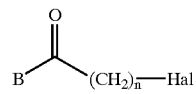

wherein B is halo or hydroxy, Hal represents Cl, Br or I and n is as defined above, in the presence of a suitable Lewis acid to produce a ω'-halo-α'-keto-α, α-dimethylphenylacetic acid amide compound;

(b) reacting the ω'-halo-α'-keto-α,α-dimethylphenylacetic acid amide compound with a piperidine compound of the formula

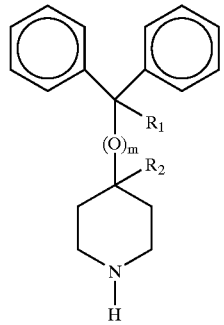

wherein $R_1$ and $R_2$ are as defined above in the presence of a suitable non-nucleophilic base to produce a ω'-piperidine-α'-keto-α,α-dimethylphenyl derivative of formula (XI) wherein $R_5$ is —$CONR_6R_7$ wherein $R_6$ and $R_7$ are as defined above;

(c) optionally hydrolyzing the ω'-piperidine-α'-keto-α, α-dimethylphenyl derivative of formula (XI) wherein $R_5$ is —$CONR_6R_7$ wherein $R_6$ and $R_7$ are as defined above to produce a ω'-piperidine-α'-keto-α, α-dimethylphenyl derivative of formula (I) wherein $R_3$ is COOH and W is —C(=O)—;

(d) optionally reacting the ω'-piperidine-α'-keto-α,α-dimethylphenyl derivative of formula (I) wherein $R_3$ is COOH and W is —C(=O)— with a suitable reducing agent to produce a ω'-piperidine-α'-hydroxy-α,α-dimethylphenyl derivative of formula (I) wherein $R_3$ is —COOH and W is —CH(OH)—; and (e) optionally reacting the ω'-piperidine-α'-hydroxy-α, α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl and W is —CH(OH)— or a ω'-piperidine-α'-keto-α,α-dimethylphenyl derivative of formula (I) wherein $R_3$ is —COOalkyl and W is —C(=O)—; and (f) optionally reacting the ω'-piperidine-α'-keto-α,α-dimethylphenyl derivative of formula (I) wherein $R_3$ is —COOH and W is —C(=O)—, the ω'-piperidine-α'-keto-α,α-dimethylphenyl derivative of formula (I) wherein $R_3$ is —COOalkyl and W is —C(=O)—, the ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl derivative of formula (I) wherein $R_3$ is —COOalkyl and W is —CH(OH)— with an appropriate deprotecting reagent, with the proviso that each of the hydroxy groups present in the compounds described in steps a–e are optionally protected or unprotected.

Another embodiment of the present invention involves a process for preparing the piperidine derivatives of formula

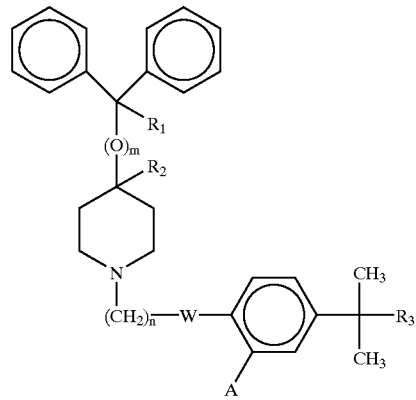

(I)

wherein
W represents —C(=O)— or —CH(OH)—;
$R_1$ represents hydrogen or hydroxy;
$R_2$ represents hydrogen; or
$R_1$ and $R_2$ taken together form a second bond between the carbon atoms bearing $R_1$ and $R_2$;
n is an integer of from 1 to 5;
m is an integer 0 or 1;
$R_3$ is —COOH or —COOalkyl wherein the alkyl moiety has from 1 to 6 carbon atoms and is straight or branched;
each of A is hydrogen or hydroxy; and
pharmaceutically acceptable salts and individual optical isomers thereof, with the proviso that where $R_1$ and $R_2$ are taken together to form a second bond between the carbon atoms bearing $R_1$ and $R_2$ or where $R_1$ represented. hydroxy, m is an integer 0, comprising the steps of:

(a) reacting a toluene compound of the formula

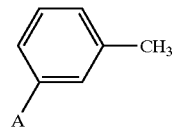

wherein A is as defined above with a ω-halo compound of the formula

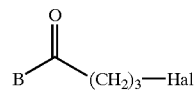

wherein B is halo or hydroxy, Hal represents Cl, Br or I and n is as defined above, in the presence of a suitable Lewis acid to produce a ω-halo-tolylketone compound;

(b) reacting the ω-halo-tolylketone compound with a suitable base to give a cyclopropyl-tolylketone compound;

(c) reacting the cyclopropyl-tolylketone compound with a suitable halogenating agent to give a cyclopropyl-halotolylketone compound;

(d) reacting the cyclopropyl-halotolylketone compound with a suitable cyanating agent to give a cyclopropyl cyanotolylketone compound;

(e) reacting the cyclopropyl cyanotolylketone compound with a suitable methylating agent to give a cyclopropyl cyanocumylketone compound;

(f) reacting the cyclopropyl cyanocumylketone compound with a suitable base to give a cyclopropylketo-α,α-dimethylphenylacetic acid amide;

(g) reacting the cyclopropylketo-α,α-dimethylphenylacetic acid amide with an appropriate straight or branched $C_1$–$C_6$ alcohol in the presence of a suitable anhydrous acid to give a ω'-halo-α'-keto-α,α-dimethylphenylacetic acid ester compound;

(h) reacting the ω'-halo-α'-keto-α,α-dimethylphenylacetic acid ester compound with a piperidine compound of the formula

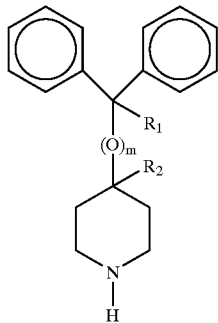

wherein $R_1$, $R_2$ and m are as defined above in the presence of a suitable non-nucleophilic base to produce a ω'-piperidine-α'-keto-α,α-dimethylphenyl derivative;

(i) optionally hydrolyzing the ω'-piperidine-α'-keto-α,α-dimethylphenyl derivative to produce a ω'-piperidine-α'-keto-α,α-dimethylphenyl derivative of formula (I) wherein $R_3$ is COOH and W is —C(=O)—;

(j) optionally reacting the ω'-piperidine-α'-keto-α,α-dimethylphenyl derivative of formula (I) wherein $R_3$ is COOH and W is —C(=O)— with a suitable reducing agent to produce a ω'-piperidine-α'-hydroxy-α,α-dimethylphenyl derivative of formula (I) wherein $R_3$ is —COOH and W is —CH(OH)—; and (k) optionally reacting the ω'-piperidine-α'-hydroxy-α,α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl and W is —CH(OH)— or a ω'-piperidine-α'-keto-α,α-dimethylphenyl derivative of formula (II) wherein $R_3$ is —COOalkyl and W is —C(=O)—; and (l) optionally reacting the ω'-piperidine-α'-keto-α,α-dimethylphenyl derivative of formula (II) wherein $R_3$ is —COOH and W is —C(=O)—, the ω'-piperidine-α'-keto-α,α-dimethylphenyl derivative of formula (II) wherein $R_3$ is —COOalkyl and W is —C(=O)—, the ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl of formula (I) wherein $R_3$ is —COOalkyl and W is —CH(OH)— with an appropriate deprotecting reagent, with the proviso that each of the hydroxy groups present in the compounds described in steps a–k are optionally protected or unprotected.

Another embodiment of the present invention involves a process for preparing the piperidine derivatives of formula

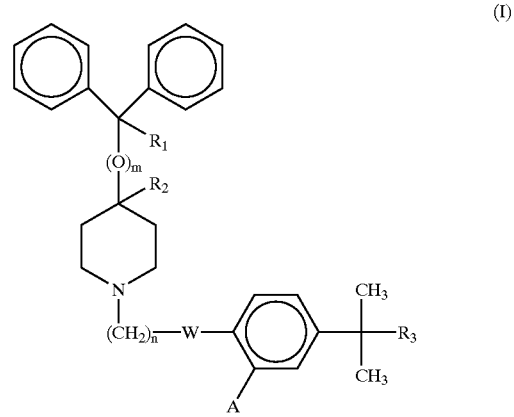

(I)

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_3$ is —COOH or —COOalkyl wherein the alkyl moiety has from 1 to 6 carbon atoms and is straight-or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0, comprising the steps of:

(a) reacting a phenylacetic acid ester compound of the formula

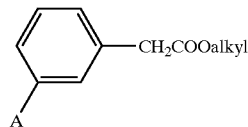

wherein A is as defined above with a ω-halo compound of the formula

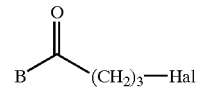

wherein B is halo or hydroxy, Hal represents Cl, Br or I and n is as defined above, in the presence of a suitable Lewis acid to produce a ω'-halo-α'-keto-phenylacetic acid ester compound;

(b) reacting the ω'-halo-α'-keto-phenylacetic acid ester compound with a suitable methylating agent in the presence of a suitable base to give a cyclopropylketo-α,α-dimethylphenylacetic acid ester;

(c) purifying the cyclopropylketo-α,α-dimethylphenylacetic acid ester by distillation and/or recrystallization;

(d) reacting the cyclopropylketo-α,α-dimethylphenylacetic acid ester with an appropriate straight or branched $C_1$–$C_6$ alcohol in the presence of a suitable anhydrous acid to give a ω'-halo-α'-keto-α,α-dimethylphenylacetic acid ester compound;

(e) reacting the ω'-halo-α'-keto-α,α-dimethylphenylacetic acid ester compound with a piperidine compound of the formula

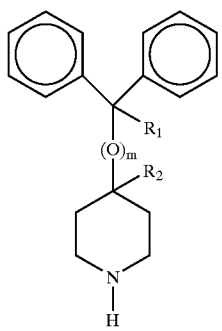

wherein $R_1$, $R_2$ and m are as defined above in the presence of a suitable non-nucleophilic base to produce a ω'-piperidine-α'-keto-α,α-dimethylphenyl derivative of formula (I) wherein $R_3$ is —COOalkyl and W is —C(=O)—;

(f) optionally hydrolyzing the ω'-piperidine-α'-keto-α,α-dimethylphenyl derivative of formula (I) wherein $R_3$ is —COOalkyl and W is —C(=O)— to produce a ω'-piperidine-α'-keto-α,α-dimethylphenyl derivative of formula (I) wherein $R_3$ is COOH and W is —C(=O)—;

(g) optionally reacting the ω'-piperidine-α'-keto-α,α-dimethylphenyl derivative of formula (I) wherein $R_3$ is COOH and W is —C(=O)— with a suitable reducing agent to produce a ω'-piperidine-α'-hydroxy-α,α-dimethylphenyl derivative of formula (I) wherein $R_3$ is —COOH and W is —CH(OH)—; and (h) optionally reacting the ω'-piperidine-α'-hydroxy-α,α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl ad W is —CH(OH)— or a ω'-piperidine-α'-keto-α,α-dimethylphenyl derivative of formula (I) wherein $R_3$ is —COOalkyl and W is —C(=O)—; and (i) optionally reacting the ω'-piperidine-α'-keto-α,α-dimethylphenyl derivative of formula (I) wherein $R_3$ is —COOH and W is —C(=O)—, the ω'-piperidine-α'-keto-α,α-dimethylphenyl derivative of formula (I) wherein $R_3$ is —COOalkyl and W is —C(=O)—, the ω'-piperidine-α'-hydroxy-α,α-dimethylphenyl derivative of formula (I) wherein $R_3$ is —COOH and W is —CH(OH)— or the ω'-piperidine-α'-hydroxy-α,α-dimethylphenyl of formula (I) wherein $R_3$ is —COOalkyl and W is —CH(OH)— with an appropriate deprotecting reagent, with the proviso that each of the hydroxy groups present in the compounds described in steps a–h are optionally protected or unprotected.

(g) optionally reacting the ω'-piperidine-α'-keto-α,α-dimethylphenyl derivative of formula (I) wherein $R_3$ is COOH and W is —C(=O)— with a suitable reducing agent-to produce a ω'-piperidine-α'-hydroxy-α,α-dimethylphenyl derivative of formula (I) wherein $R_3$ is —COOH and W is —CH(OH)—; and (h) optionally reacting the ω'-piperidine-α'-hydroxy-α,α-dimethylphenyl derivative of formula (I) wherein $R_3$ is —COOH and W is —CH(OH)— or the appropriate ω'-piperidine-α'-keto-α,α-dimethylphenyl derivative of formula (I) wherein $R_3$ is —COOH and W is —C(=O)— with an appropriate straight or branched $C_1$–$C_6$ alcohol in the presence of a suitable acid to produce a ω'-piperidine-α'-hydroxy-α,α-dimethylphenyl derivative of formula (I) wherein $R_3$ is —COOalkyl and W is —CH(OH)— or a ω'-piperidine-α'-keto-α,α-dimethylphenyl derivative of formula (I) wherein $R_3$ is —COOalkyl and W is —C(=O)—; and (i) optionally reacting the ω'-piperidine-α'-keto-α,α-dimethylphenyl derivative of formula (I) wherein $R_3$ is —COOH and W is —C(=O)—, the ω'-piperidine-α'-keto-α,α-dimethylphenyl derivative of formula (I) wherein $R_3$ is —COOalkyl and W is —C(=O)—, the ω'-piperidine-α'-hydroxy-α,α-dimethylphenyl derivative of formula,(I) wherein $R_3$ is —COOH and W is —CH(OH)— or the ω'-piperidine-α'-hydroxy-α,α-dimethylphenyl of formula (I) wherein $R_3$ is —COOalkyl and W is —CH(OH)— with an appropriate deprotecting reagent, with the proviso that each of the hydroxy groups present in the compounds described in steps a–h are optionally protected or unprotected.

As used herein, the term "$C_1$–$C_6$alkyl" or "alkyl" refers to a straight or branched alkyl group having from 1 to 6 carbon atoms and as referred to herein are methyl, ethyl, n-propyl, isopropyl, n-butyl, sec-butyl, tert-butyl, n-pentyl, neopentyl and n-hexyl. The term "$C_1$–$C_6$alkoxy" refers to a straight or branched alkoxy group having from 1 to 6 carbon atoms and as referred to herein are methoxy, ethoxy, n-propoxy, isopropoxy, n-butoxy, sec-butoxy, tert-butoxy, n-pentoxy, neopentoxy and n-hexoxy. The term "Hal" or "halo" refers to a halogen group and includes Cl, Br or I.

The piperidine derivatives of the formula (IX) can form pharmaceutically acceptable salts. Pharmaceutically acceptable acid addition salts of the compounds of this invention are those of any suitable inorganic or organic acid. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranillic, cinnamic, salicyclic, 4-aminosalicyclic, 2-phenoxybenzoic, 2-acetoxybenzoic, and mandelic acid, sulfonic acids, such as, methanesulfonic, ethanesulfonic and β-hydroxyethanesulfonic acid. Non-toxic salts of the compounds of the above-identified formula formed with inorganic or organic bases are also included within the scope of this invention and include, for example, those of alkali metals, such as, sodium, potassium and lithium, alkaline earth metals, for example, calcium and magnesium, light metals of group IIIA, for example, aluminum, organic amines, such as, primary, secondary or tertiary amines, for example, cyclohexylamine, ethylamine, pyridine, methylaminoethanol and piperazine. The salts are prepared by conventional means as, for example, by treating a piperidine derivative of formula (I) with an appropriate acid or base.

The novel intermediates of formula (II), formula (III), formula (IV), formula (V), formula (VI) and formula (VII) wherein $R_5$ is hydrogen may be prepared as described in Scheme A. In Scheme A, all substituents are as previously defined unless otherwise indicated.

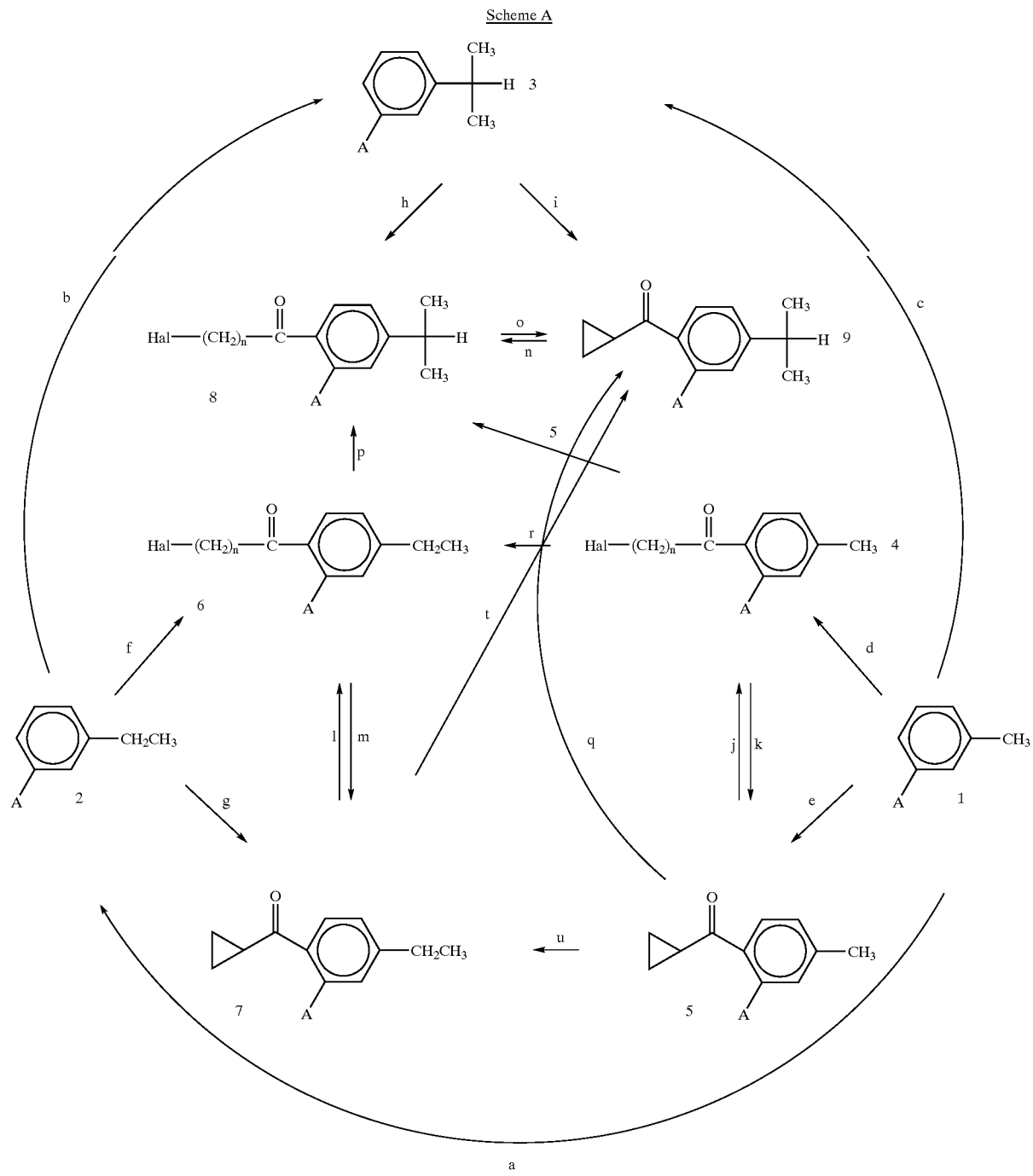

Scheme A provides various general synthetic procedures for preparing the novel intermediates of formula (II), formula (III) and formula (IV) wherein $R_5$ is hydrogen.

In step a, the appropriate toluene derivative of structure (1) is methylated to give the corresponding ethylbenzene derivative of structure (2).

For example, the appropriate toluene derivative of structure (1) is reacted with a slight molar excess of an appropriate methylating agent, such as iodomethane, chloromethane or bromomethane in the presence of a suitable non-nucleophilic base, such as potassium t-butoxide or sodium hydride. The reaction is typically conducted in a suitable organic solvent, such as diglyme, tert-butyl methyl ether or methylene chloride, for a period of time ranging from 30 minutes to 24 hours and at a temperature range of from −78° C. to room temperature. The corresponding ethylbenzene derivative of structure (2) is recovered from the reaction zone by extractive methods as is known in the art and may be purified by distillation.

In step b, the appropriate ethylbenzene derivative of structure (2) is methylated to give the corresponding cumene derivative of structure (3) as described previously in step a, but using at least 2 molar equivalents of methylating agent.

In step c, the appropriate toluene derivative of structure (1) is dimethylated to give the corresponding cumeme derivative of structure (3) as described previously in step a but using at least 2 molar equivalents of methylating agent.

In step d, the appropriate toluene derivative of structure (1) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo tolylketone compound of structure (4).

For example, the appropriate ω-halo tolylketone compound of structure (4) may be prepared by reacting an appropriate toluene derivative of structure (1) with an appropriate ω-halo compound of the structure Hal-$(CH_2)_n$—C(=O)—B, wherein B is Hal or hydroxy, Hal is Cl, Br or I and n is as previously defined, which are known in the art or are prepared by procedures well known in the art, under the general conditions of a Friedel—Crafts acylation using a suitable Lewis acid. The reaction is carried out in a solvent, such as carbon disulfide, 1,2-dichloroethane, n-hexane, acetonitrile, 1-nitropropane, nitromethane, diethyl ether and carbon tetrachloride, methylene chloride, tetrachloroethane or nitrobenzene with methylene chloride being the preferred solvent. The reaction time varies from about ½ hour to 25 hours, preferably 10 to 16 hours and the reaction temperature varies from about 0° C. to 25° C. The corresponding ω-halo tolylketone compound of structure (4) is recovered from the reaction Cone by an aqueous quench followed by extraction as is known in the art. The ω-halo tolylketone compound of structure (4) may be purified by procedures well known in the art, such as crystallization and/or distillation.

Alternatively, the appropriate toluene derivative of structure (1) may be acylated with the ω-halo compound of the structure Hal-$(CH_2)_n$—C(=O)—B, wherein B is hydroxy, Hal is Cl, Br or I and n is as previously defined in the presence of a Lewis acid to give the corresponding ω-halo tolylketone compound of structure (4) as described in *Arch. Pharm.* 306, 807 1973. In general, an appropriate toluene derivative of structure (1) and the ω-halo compound of the structure Hal-$(CH_2)_n$—C(=O)—B, wherein B is hydroxy, are melted together at about 50° C., then cooled to about 10° C. after which a Lewis acid is added in an amount about 2.2 times the molar amount of the appropriate toluene derivative of structure (1) employed. The mixture is heated at about 70° C. for about 2 hours after which a 30% sodium acetate solution is added and extracted with ether. The organic layer is dried and the solvent evaporated to give the corresponding ω-halo tolylketone compound of structure (4). The ω-halo tolylketone compound of structure (4) may be purified by procedures well known in the art, such as crystallization and/or distillation.

Suitable Lewis acids for the acylation reaction described in step d are well known and appreciated in the art. Examples of suitable Lewis acids are boron trichloride, aluminum chloride, titanium tetrachloride, boron trifluoride, tin tetrachloride, ferric chloride, cobalt(II) chloride and zinc chloride, with aluminum chloride being preferred. The selection and utilization of suitable Lewis acids for the acylation reaction of step d is well known and appreciated by one of ordinary skill in the art.

The starting ω-halo compound of the structure Hal-$(CH_2)_n$—C(=O)—B, wherein B is Hal or hydroxy, Hal is Cl, Br or I and n is as previously defined are commercially available of easily prepared by generally known methods.

While also not necessary for utilization in the acylation reaction of step d, the phenol functionality of those toluene derivatives of structure (1), wherein A is hydroxy may be protected with a suitable protecting group. For example, suitable protecting groups for the phenolic hydroxy include methyl ether, 2-methoxyethoxymethyl ether (MEM), cyclohexyl ether, o-nitrobenzyl ether, 9-anthryl ether, t-butyldimethylsilyl ether, acetate, benzoate, methyl carbamate, benzyl carbamate, aryl pivaloate and aryl methanesulfonate.

In step e, to appropriate toluene derivative of structure (1) is acylated with an appropriate cyclopropyl compound of the structure

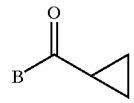

wherein B is as previously defined to give the corresponding cyclopropyl tolylketone derivative of structure (5) as described previously in step d.

In step f, the appropriate ethylbenzene derivative of structure (2) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo ethylphenylketone compound of structure (6) as described previously in step d.

In step g, the appropriate ethylbenzene derivative of structure (2) is acylated with an appropriate cyclopropyl compound of the structure

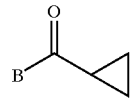

wherein B is as previously defined to give the corresponding cyclopropyl ethylphenylketone derivative of structure (7) as described previously in step e.

In step h, the appropriate cumene derivative of structure (3) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo cumylketone compound of structure (8) as described previously in step d.

In step i, to appropriate cumene derivative of structure (3) is acylated with an appropriate cyclopropyl compound of the structure

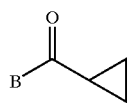

wherein B is as previously defined to give the corresponding cyclopropyl cumylketone derivative of structure (9) as described previously in step e.

In step j, the cyclopropyl functionality of the appropriate cyclopropyl tolylketone derivative of structure (5) is ring-opened to give the corresponding ω-halo tolylketone compound of structure (4) wherein n=3.

For example, the appropriate cyclopropyl tolylketone derivative of structure (5) is reacted with an appropriate hydrogen halide in a suitable organic solvent, such as toluene, xylene and ethanol. The reaction is typically conducted at a temperature range of from room temperature to 70° C. and for a period of time ranging from 20 minutes to 10 hours. The corresponding ω-halo tolylketone compound of structure (4) wherein n=3 is isolated from the reaction zone by evaporation of the solvent or may be stored in a solution of the hydrogen halide.

In step k, the appropriate ω-halo tolylketone compound of structure (4) wherein n=3 is ring-closed to give the corresponding cyclopropyl tolylketone derivative of structure (5).

For example, the appropriate ω-halo tolylketone compound of structure (4) wherein n=3 is reacted with an appropriate non-nucleophilic base, such as sodium hydroxide or potassium hydroxide in a suitable organic protic solvent, such as methanol or ethanol. The reaction is typically conducted at a temperature range of from −10° C. to room temperature and for a period of time ranging from 10 minutes to 5 hours. The corresponding cyclopropyl tolylketone derivative of structure (5) is isolated from the reaction zone by extractive methods as are known in the art and may be purified by distillation.

In step 1, the cyclopropyl functionality of the appropriate cyclopropyl ethylphenylketone derivative of structure (7) is ring-opened to give the corresponding ω-halo ethylphenylketone compound of structure (6) wherein n=3 as described-previously in step j.

In step m, the appropriate ω-halo ethylphenylketone compound of structure (6) wherein n=3 is ring-closed to give the corresponding cyclopropyl ethylphenylketone derivative of structure (7) as described previously in step k.

In step n, the cyclopropyl functionality of the appropriate cyclopropyl cumylketone derivative of structure (9) is ring-opened to give the corresponding ω-halo cumylketone compound of structure (8) wherein n=3 as described previously in step j.

In step o, the appropriate ω-halo cumylketone compound of structure (8) wherein n=3 is ring-closed to give the corresponding cyclopropyl cumylketone derivative of structure (9) as described previously in step k.

In step p, the appropriate ω-halo ethylphenylketone compound of structure (6) is methylated to give the corresponding ω-halo cumylketone compound of structure (8) as described previously in step a.

In step q, the appropriate cyclopropyl tolylketone derivative of structure (5) is dimethylated to give the corresponding cyclopropyl cumylketone derivative of structure (9) as described previously in step c.

In step r, the appropriate ω-halo tolylketone compound of structure (4) is methylated to give the corresponding ω-halo ethylphenylketone compound of structure (6) as described previously in step a.

In step s, the appropriate ω-halo tolylketone compound of structure (4) is dimethylated to give the corresponding ω-halo cumylketone compound of structure (8) as described previously in step c.

In step t, the appropriate cyclopropyl ethylphenylketone derivative of structure (7) is methylated to give the corresponding cyclopropyl cumylketone derivative of structure (9) as described previously in step a.

In step u, the appropriate cyclopropyl tolylketone derivative of structure (5) is methylated to give the corresponding cyclopropyl ethylphenylketone derivative of structure (7) as described previously in step a.

Starting materials for use in Scheme A are readily available to one of ordinary skill in the art.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 1

Step h: 4-Chloro-1-(4-isopropyl-phenyl)-butan-1-one

Slurry aluminum chloride (140.9 g, 1.075 mol) and 4-chlorobutyryl chloride (148 g, 1.05 mol) in methylene chloride (1.0 L) add, by dropwise addition, cumene (125 g, 1.04 mol) over a thirty minute period under a nitrogen atmosphere while maintaining the internal temperature between 5–8° C. with an ice bath. Allow the stirred solution to come to room temperature and continue stirring under nitrogen for 14 hours. Cautiously add the methylene chloride solution to 1 L of crushed ice with stirring and add additional methylene chloride (400 mL). Separate the organic phase and wash with 10% hydrochloric acid (3×300 mL), water (3×300 mL), 10% sodium bicarbonate (3×300 mL) and water (3×300 mL). Dry (MgSO$_4$), filter and wash with methylene chloride (150 mL). Evaporate the solvent to give the title compound (203 g, 86%) as a clear oil which crystallizes on standing; mp 35–37° C.

$^1$H NMR (300 MHz, CDCl$_3$) δ7.91 (d, J=8.2 Hz, 2H), 7.31 (d, J=8.2 Hz, 2H), 3.65 (t, J=6.3 Hz, 2H), 3.13 (t, J=6.9 Hz, 2H), 2.95 (p, J=6.9 Hz, 1H), 2.20 (p, J=6.6 Hz, 2H), 1.26 (d, J=6.9 Hz, 6H); $^{13}$C NMR (75 MHz, CDCl$_3$) δ198.2, 154.4, 134.4, 128.1, 126.5, 44.5, 32.96, 34.0, 26.7, 23.5; IR (CDCl$_3$) 2950, 2920, 1675, 1680, 1600, 1410, 1225 cm$^{-1}$; MS (GCCIMS (methane)) 255 (3), 251 (10), 227 (30 (M+H)), 225 (100 (M+H)), 189 (70), 147 (95), 107 (13, 105 (40).

Anal. Calcd for C$_{13}$H17OCl: C, 69.48; H, 7.62; Found: C, 69.31; H, 7.39.

EXAMPLE 2

Step d: 4-Chloro-1-(4-methyl-phenyl)-butan-1-one

Suspend anhydrous AlCl3 (156 g, 1.15 mol) in toluene (1500 mL) and cool to 2–4° C. Add, by slow addition, a solution of 4-chlorobutyryl chloride (165.5 g, 1.15 mol) in toluene (300 mL). Stir for 15 minutes and pour into stirring ice-water (2.5 L). Stir for 30 hours, decant the toluene and extract the aqueous phase with toluene (700 mL). Combine the organic layers and wash three times with water (1 L, 1 L, 500 mL). Evaporate the solvent in vacuo to give the title compound as a pale yellow oil (292.3 g, 95%).

EXAMPLE 3

Step k: Cyclopropyl-p-tolyl-methanone

Dissolve potassium hydroxide (126 g) in methanol (450 mL), stir and cool in an ice-water bath. Add, by dropwise addition, a solution of 4-chloro-1-(4-methyl-phenyl)-butan-1-one (292 g) in methanol (450 mL). Stir for 20 minutes at 8–10° C. and partially evaporate the methanol in vacuo to give 400 mL of a residue. Pour the residue, with stirring, into water (1500 mL), filter the white solid and dry under vacuum to give the title compound as a white solid (190.8 g, 90%).

The following compounds can be prepared using the methodology depicted in Scheme A:

Cyclopropyl-(4-isopropyl-phenyl)-methanone;
Cyclopropyl-(4-ethyl-phenyl)-methanone; and
4-Chloro-1-(4-ethyl-phenyl)-butan-1-one.

The novel intermediates of formula (II), formula (III), formula (IV), formula (V), formula (VI) and formula (VII) wherein $R_5$ is OH, Cl, Br or I may be prepared as described s in Scheme B. In Scheme B, all substituents are as previously defined unless otherwise indicated.

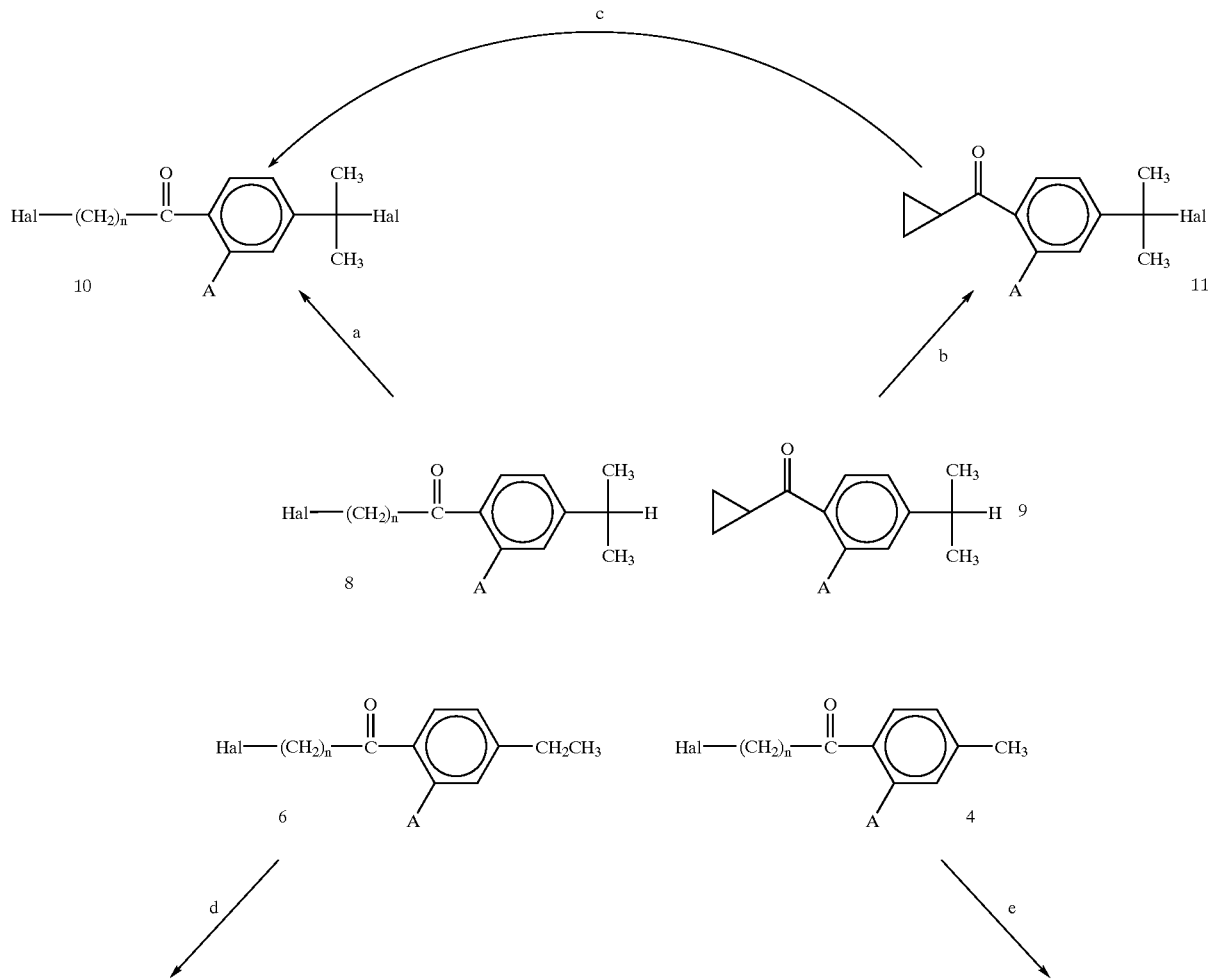

Scheme B

-continued

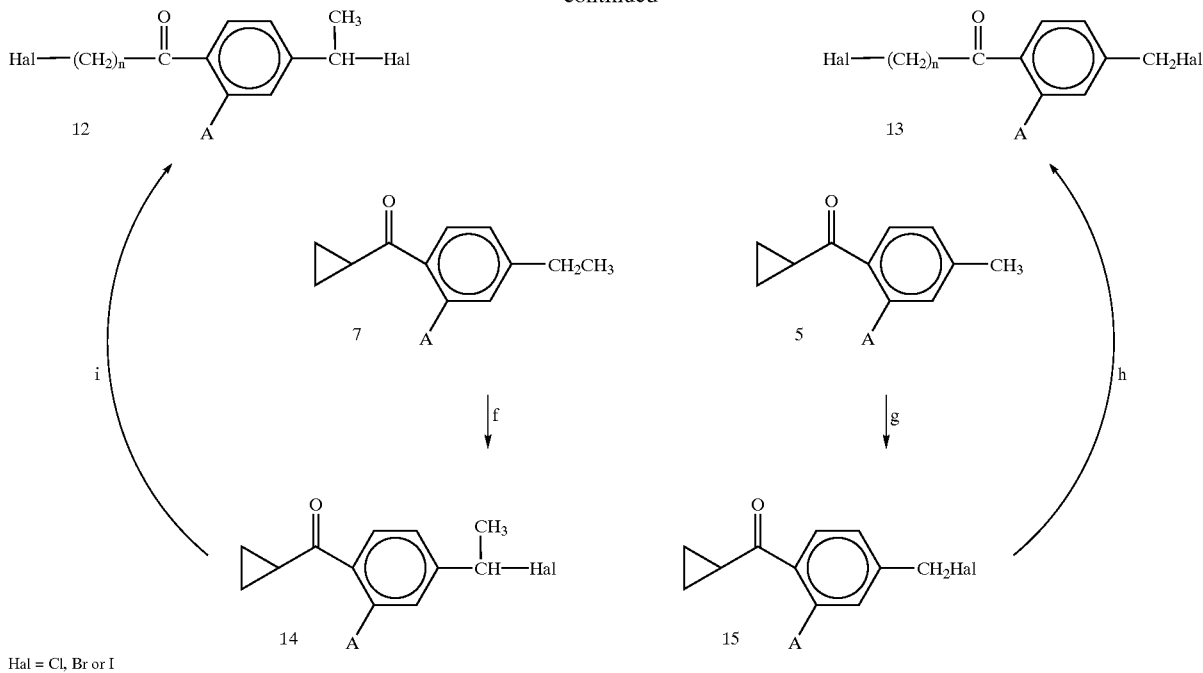

Hal = Cl, Br or I

Scheme B provides various general synthetic procedures for preparing the novel intermediates of formula (II), formula (III), formula (IV), formula (V), formula (VI) and formula (VII) wherein $R_5$ is OH, Cl, Br or I.

In step a, the appropriate ω-halo cumylketone compound of structure (8) is halogenated to give the corresponding ω-halo-halocumylketone compound of structure (10).

For example, the appropriate ω-halo-halocumylketone compound of structure (10) may be prepared by reacting an appropriate ω-halo cumylketone compound of structure (8) with a suitable halogenating agent optionally in the presence of a catalytic amount of a suitable initiator. Examples of suitable brominating agents are N-bromosuccinimide, and 1,3-dibromo-5,5-dimethyl hydantoin, with N-bromosuccinimide being preferred. An example of suitable chlorinating agent is N-chlorosuccinimide and an example of a suitable iodinating agent is N-iodosuccinimide. Examples of suitable initiators are benzoyl peroxide, AIBN, t-butyl peroxide and ultraviolet light. The reaction is carried out in a solvent, such as carbon tetrachloride, methylene chloride, 1,2-dichlorobenzene, 1,2-dichloroethane, ethyl formate or ethyl acetate, with carbon tetrachloride being the preferred solvent. The reaction time varies from about ½ hour to 8 hours, preferably ½ to 2 hours and the reaction temperature varies from about 25° C. to the reflux temperature of the solvent employed, preferably 70° C. to 80° C. The corresponding ω-halo-halocumylketone compound of structure (10) is recovered from the reaction zone by extractive methods as are known in the art followed by evaporation of the solvent.

In addition, the halogenation reaction of step a may be carried out in a 2-phase procedure. For example, the appropriate ω-halo-halocumylketone compound of structure (10) may be prepared by reacting an appropriate ω-halo cumylketone compound of structure (8) with a suitable halogenating agent, such as sodium bromate/sodium bromide, in a solvent mixture such as methylene chloride and water, catalyzing the reaction with, for example, ultraviolet light. The corresponding ω-halo-halocumylketone compound of structure (10) is recovered from the reaction zone by extractive methods as are known in the art followed by evaporation of the solvent.

The ω-halo-halocumylketone compound of structure (10) may dehydrohalogenate to the corresponding a-methylstyrene, giving various mixtures of ω-halo-halocumylketone compound of structure (10) and a-methylstyrene compounds. The α-methylstyrene compounds in such a mixture may be back-converted to ω-halo-halocumylketone compound of structure (10) by treatment with anhydrous hydrogen-halide gas. Typically, a solution of the mixture of ω-halo-halocumylketone compound of structure (10) and α-methylstyrene compounds in a suitable organic solvent, such as methylene chloride or acetonitrile, is treated with a suitable anhydrous hydrogen halide gas, such as hydrogen chloride. The reaction is typically treated with the hydrogen halide gas for a period of time ranging from 30 minutes to 5 hours and at a temperature range of from 0° C. to room temperature. The remediated ω-halo-halocumylketone compound of structure (10) may be isolated by evaporation of solvent, but may be stored as a solution in the organic solvent containing hydrogen halide gas.

In addition, halogen exchange of the benzylic halogen can be accomplished by thorough solvolysis in the presence of the appropriate hydrogen halide.

For example, the ω-chloro-halocumylketone compound of structure (10) can be prepared from the ω-bromo-halocumylketone compound of structure (10) by thorough aqueous solvolysis in the presence of hydrogen chloride.

In step b, the appropriate cyclopropyl cumylketone derivative of structure (9) is halogenated to give the corresponding cyclopropyl halocumylketone compound of structure (11) as described previously in step a.

In step c, the cyclopropyl functionality of the appropriate cyclopropyl halocumylketone compound of structure (11) is ring-opened to give the corresponding ω-halo-halocumylketone compound of structure (10) wherein n=3 as described previously in Scheme A, step j.

In step d, the appropriate ω-halo ethylphenylketone compound of structure (6) is halogenated to give the corresponding ω-halo-haloethylphenylketone compound of structure (12) as described previously in step a.

In step e, the appropriate ω-halo tolylketone compound of structure (4) is halogenated to give the corresponding ω-halo halotolylketone compound of structure (13) as described previously in step a.

In step f, the appropriate cyclopropyl ethylphenylketone derivative of structure (7) is halogenated to give the corresponding cyclopropyl haloethylphenylketone compound of structure (14) as described previously in step a.

In step g, the appropriate cyclopropyl tolylketone derivative of structure (5) is halogenated to give the corresponding cyclopropyl halotolylketone of structure (15) as described previously in step a.

In step h, the appropriate cyclopropyl halotolylketone of structure (15) is ring-opened to give the corresponding ω-halo halotolylketone compound of structure (13) wherein n=3 as described previously in Scheme A, step j.

In step i, the appropriate cyclopropyl haloethylphenylketone compound of structure (14) is ring-opened to give the corresponding ω-halo-haloethylphenylketone compound of structure (12) wherein n=3 as described previously in Scheme A, step j.

In addition, the novel intermediates of formula (II), formula (III), formula (IV), formula (V), formula (VI) and formula (VII) wherein $R_5$ is OH may be prepared by solvolysis of the corresponding novel intermediates of formula (II), formula (III), formula (IV), formula (V), formula (VI) and formula (VII) wherein $R_5$ is Cl, Br or I, with, for example, tetrahydrofuran and water or any slightly acidic medium.

Starting materials for use in Scheme B are readily available to one of ordinary skill in the art.

The following examples present typical syntheses as described in Scheme B. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 4

1-[4-(1-Bromo-1-methyl-ethyl)-phenyl]-4-chloro-butan-1-one

Step a, Method A

Dissolve 4-chloro-1-(4-isopropyl-phenyl)-butan-1-one (2.10 g, 9.35 mmol) in carbontetrachloride (30 mL), add N-bromosuccinimide (1.75 g, 9.83 mmol) and benzoylperoxide (3 mg) and stir at reflux for 1 hour. Cool the reaction mixture, filter, wash with water and brine. Dry (MgSO$_4$), filter and vaporate the solvent in vacuo to give the title compound as an amber oil.

Step a, Method B

Dissolve 4-chloro-1-(4-isopropyl-phenyl)-butan-1-one (5.00 g, 22.2 mmol) and N-bromosuccinimide (4.1 g, 23.0 mmol) in carbon tetrachloride (25 mL) and add AIBN radical initiator (300 mg). Stir and maintain under a nitrogen atmosphere at 80–90° C. or optionally irradiate with a sunlamp until a vigorous exotherm occurs at which point momentarily remove until reflux subsides and then reapply the heat. Reflux for 30 minutes and add another potion of N-bromosuccinimide (100 mg) while maintaining reflux and reflux an additional 15 minutes. Cool to room temperature and precipitate the succinimide from the solution by allowing to stand overnight. Filter and wash the succinimide (2.25 g) with carbon tetrachloride (20 mL). Combine the filtrates and evaporate the solvent in vacuo to give the title compound as a yellow oil (6.80 g, 100%).

$^1$H NMR (300 MHz, CDCl$_3$) δ7.935 (d, J=8.4 Hz, 2H), 7.70 (d, J=8.4 Hz, 2H), 3.66 (t, J=6.3 Hz, 2H), 3.16 (t, J=6.8 Hz, 2H), 2.21 (p, J=6.8 Hz, 2H), 2.19 (s, 6H); $^{13}$C NMR (75 MHz, CDCl$_3$) δ198.1 (151.63), 135.8, 128.0, 126.0, 62.3, 44.5, 35.3, 35.1, 26.7; IR (neat) 2970, 2910, 1680, 1675, 1600, 1402, 1225, 1180 cm$^{-1}$.

Step a, Method C

Dissolve 4-chloro-1-(4-isopropyl-phenyl)-butan-1-one (74.7 g, 333 mmol) in methylene chloride (250 mL) and add sodium bromate (17.6 g, 117 mmol) in water (75 mL) in a three-necked Morton flask equipped with an overhead stirrer. Cool the solution to 10° C. and irradiate with two 150 W incandescent flood lamps. Add, by dropwise addition, a solution of sodium bromide (24 g, 233 mmol) and stir for 2 hours. Illuminate for another 30 minutes, add sodium dithionate (2.0 g), separate the organic phase, dry (MgSO$_4$) and evaporate the solvent in vacuo to give the title compound (100 g, 99%).

Step a, Method D

Dissolve 1-[4-(1-bromo-1-methyl-ethyl)-phenyl]-4-chloro-butan-1-one (10.4 g assayed at 67% by weight and containing 18 wt % 1-[4-(2-propene)-phenyl]-4-chloro-butan-1-one) in methylene chloride (50 mL) and sparge hydrogen chloride through the solution for 70 minutes. Evaporate the solvent in vacuo to give a 3:1 mixture of 1-[4-(1-bromo-1-methyl-ethyl)-phenyl]-4-chloro-butan-1-one and 1-[4-(1-chloro-1-methyl-ethyl)-phenyl]-4-chloro-butan-1-one (11.6 g).

EXAMPLE 5

(4-Bromomethyl-phenyl)-cyclopropyl-methanone

Step g: Dissolve 4-chloro-1-(4-isopropyl-phenyl)-butan-1-one (20 g, 124 mmol) and 2,2'-Azolons (2-methylpropionitrile) (0.5 g) in methylene chloride (100 mL) and cool to 5° C. Add a suspension of N-bromosuccinimide (12 g) in methylene chloride (50 mL) and irradiate with light (150 Watt lamp), maintaining the temperature at 5° C. After 2, 3 and 7 hour time periods, add additional N-bromosuccinimide (6 g, 6 g, 2.8 g) and continue stirring. After 7.5 hours, wash with water (200 mL) and with 0.4M sodium hydrogen carbonate (2×200 mL). Dry (Na$_2$SO$_4$), evaporate the solvent in vacuo and recrystallize (hexane) to give the title compound as a crystalline solid (26.7 g).

The following compounds can be prepared by procedures depicted in Scheme B:

[4-(1-bromoethyl)-phenyl]-cyclopropyl-methanone;
[4-(1-bromo-1-methyl-ethyl)-phenyl]-cyclopropyl-methanone;
1-[4-(1-bromomethyl)-phenyl]-4-chloro-butan-1-one; and
1-[4-(1-bromoethyl)-phenyl]-4-chloro-butan-1-one.

The novel intermediates of formula (VIII) and (IX) and the novel intermediates of formula (II), formula (III), formula (IV), formula (V), formula (VI) and formula (VII) wherein $R_5$ is Cl, Br or I may also be prepared as described in Scheme C. In Scheme C, all substituents are as previously defined unless otherwise indicated.

Scheme C

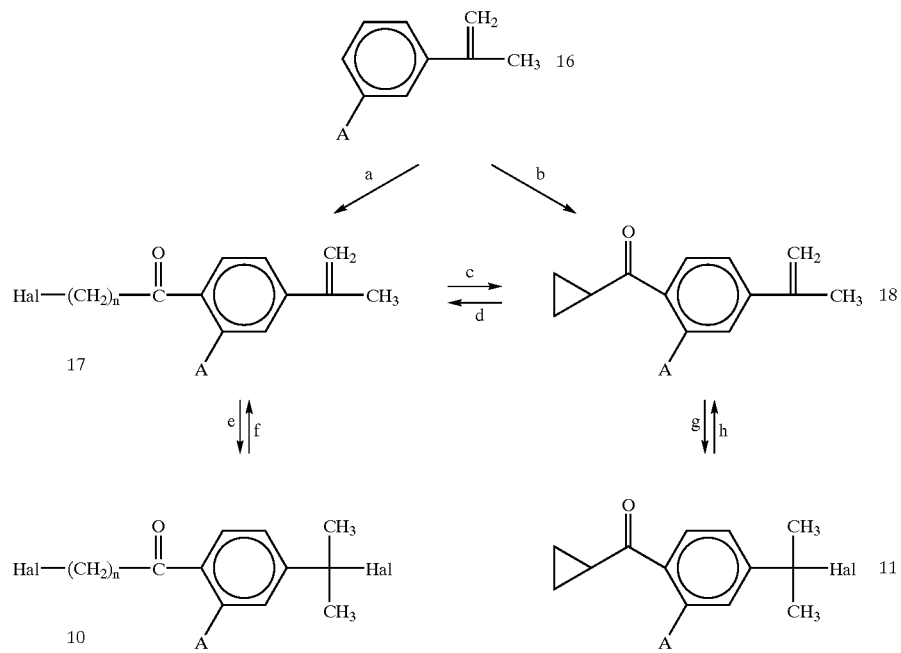

Scheme C provides various general synthetic procedures for preparing the the novel intermediates of formula (VIII) and (IX) and novel intermediates of formula (II), formula (III), formula (IV), formula (V), formula (VI) and formula (VII) wherein $R_5$ is Cl, Br or I.

In step a, the appropriate a-methylstyrene compound of structure (16) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo-α-methylstyrene compound of structure (17) as described previously in Scheme A, step d.

In step b, the appropriate α-methylstyrene compound of structure (16) is acylated with an appropriate cyclopropyl compound of the structure

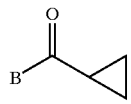

wherein B is as previously defined to give the corresponding cyclopropyl α-methylstyreneketone derivative of structure (18) as described previously in Scheme A, step e.

In step c, the appropriate ω-halo-α-methylstyrene compound of structure (17) wherein n=3 is ring-closed to give the corresponding cyclopropyl α-methylstyreneketone derivative of structure (18) as described previously in Scheme A, step k.

In step d, the appropriate cyclopropyl α-methylstyreneketone derivative of structure (18) is ring-opened to give the corresponding ω-halo-α-methylstyrene compound of structure (17) wherein n=3 as described previously in Scheme A, step j.

In step e, the appropriate ω-halo-α-methylstyrene compound of structure (17) is hydrohalogenated to give the corresponding ω-halo-halocumylketone derivative of structure (10).

For example, the appropriate ω-halo-α-methylstyrene compound of structure (17) is treated with anhydrous hydrogen halide at a temperature range of from −50° C. to room temperature, preferably 0° C.–5° C. and for a period of time ranging from 5 minutes to 2 hours. The ω-halo-halocumylketone derivative of structure (10) is recovered from the reaction zone by purging with nitrogen.

In step f, the appropriate ω-halo-halocumylketone derivative of structure (10) is dehydrohalogenated to give the corresponding ω-halo-α-methylstyrene compound of structure (17) by treatment with base as is known in the art.

In step g, the appropriate cyclopropyl α-methylstyreneketone derivative of structure (18) is hydrohalogenated to give the corresponding cyclopropyl halocumylketone compound of structure (11) as described previously in step e.

In step h, the appropriate cyclopropyl halocumylketone compound of structure (11) is dehydrohalogenated to give the corresponding cyclopropyl α-methylstyreneketone derivative of structure (18) as described previously in step f.

The novel intermediates of formula (II), formula (III), formula (IV), formula (V), formula (VI) and formula (VII) wherein $R_5$ is CN may be prepared as described in Scheme D. In Scheme D, all substituents are as previously defined unless otherwise indicated.

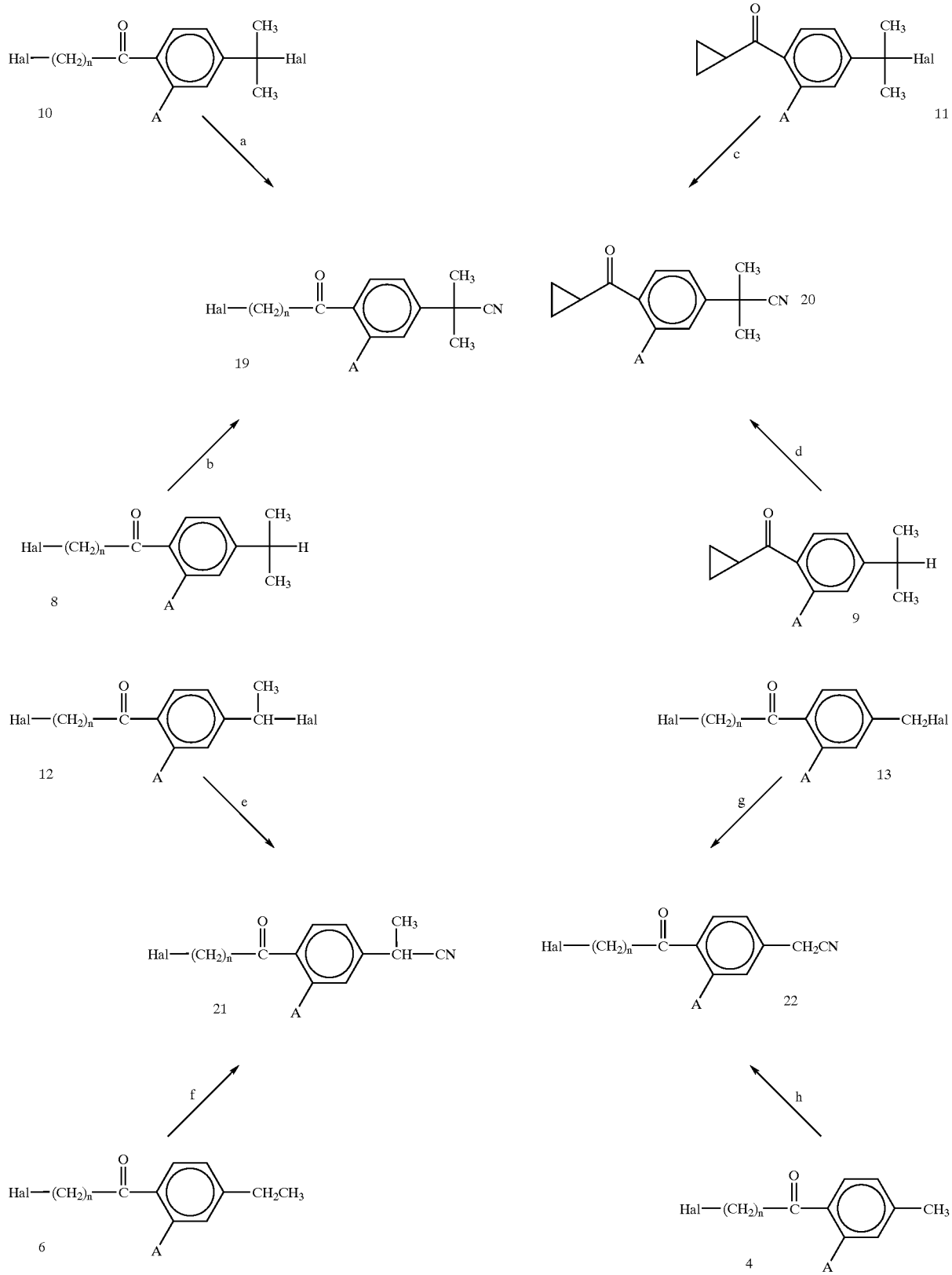
Scheme D

-continued

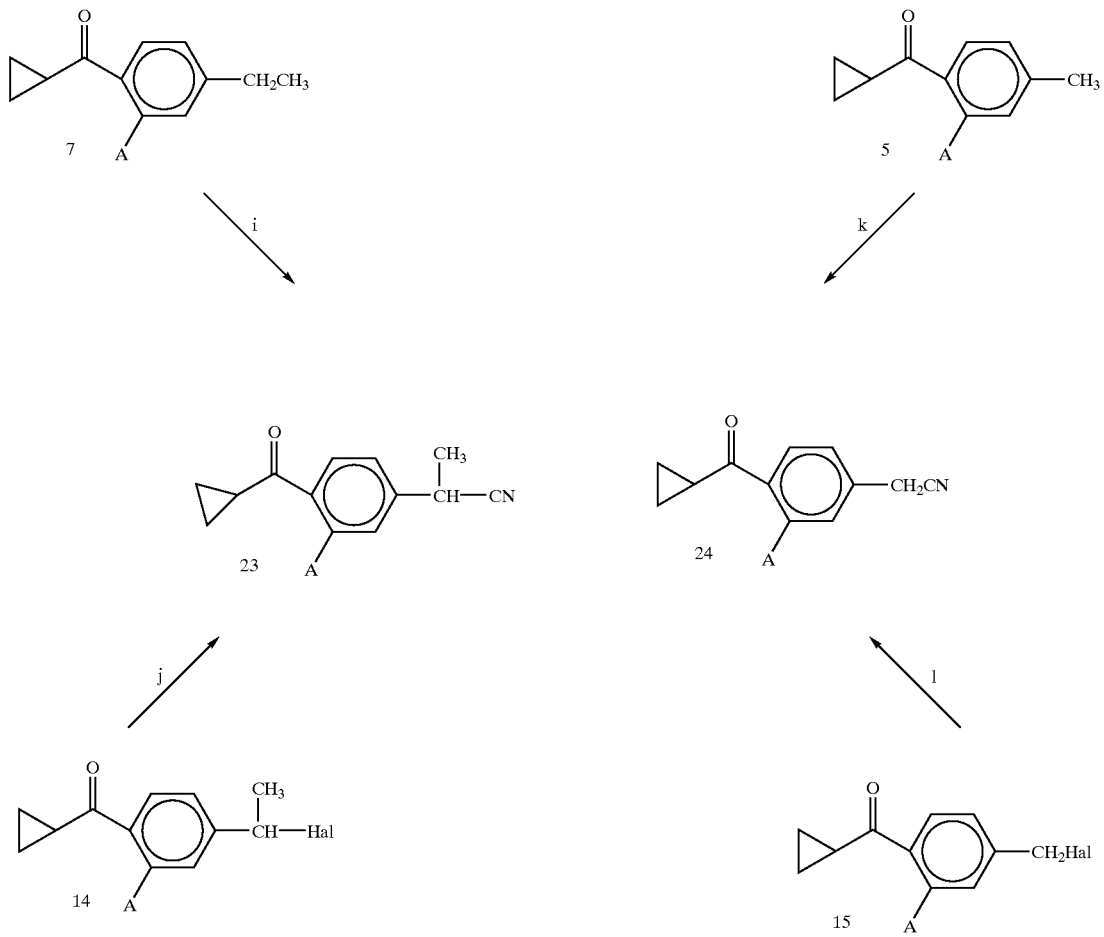

formula (III), formula (IV), formula (V), formula (VI) and formula (VII) wherein $R_5$ is CN.

In step a, the appropriate ω-halo-halocumylketone compound of structure (10) is cyanated to give the corresponding ω-halo-cyanocumylketone compound of structure (19).

For example, the appropriate ω-halo-cyanocunylketone compound of structure (19) may be prepared by reacting an appropriate ω-halo-halocumylketone compound of structure (10) with a suitable cyanating agent. Examples of suitable cyanating agents are trimethylsilyl cyanide, diethylaluminum cyanide and tetrabutylammonium cyanide, with trimethylsilyl cyanide being preferred. The reaction is carried out in a solvent, such as methylene chloride, tetrachloroethane and carbon tetrachloride, with methylene chloride being the preferred solvent. A catalytic amount of a suitable Lewis acid may also be employed in the reaction. Examples of suitable Lewis acids are boron trichloride, aluminum chloride, titanium tetrachloride, boron trifluoride, tin tetrachloride and zinc chloride, with tin tetrachloride being preferred. The reaction time varies from about ½ hour to 8 hours, preferably ½ to 2 hours and the reaction temperature varies from about 0° C. to room temperature, preferably room temperature. The ω-halo-cyanocumylketone compound of structure (16) is recovered from the reaction zone by an aqueous quench followed by extraction as is known in the art. The ω-halo-cyanocumylketone compound of structure (16) may be purified by procedures well known in the art, such as chromatography and crystallization.

In step b, the appropriate ω-halo cumylketone compound of structure (8) is cyanated to give the corresponding ω-halo-cyanocumylketone compound of structure (19).

For example, the ω-halo-cyanocurylketone compound of structure (19) may be prepared by reacting an appropriate the ω-halo cumylketone compound of structure (8) with a suitable cyanating agent. Examples of suitable cyanating agent are cyanogen chloride, cyanogen bromide and cyanogen iodide, with cyanogen chloride being preferred. The reaction is carried out according to the procedures outlined by Tanner and Bunce, *J. Am. Chem. Soc.,* 91, 3028 (1969).

In step c, the appropriate cyclopropyl halocumylketone compound of structure (11) is cyanated to give the corresponding cyclopropyl cyanocumylketone compound of structure (20) as described previously in step a.

In step d, the appropriate cyclopropyl cumylketone derivative of structure (9) is cyanated to give the corresponding cyclopropyl cyanocumylketone compound of structure (20) as described previously in step b.

In step e, the appropriate ω-halo-haloethylphenylketone compound of structure (12) is cyanated to give the corresponding ω-halo-cyanoethylphenylketone compound of structure (21) as described previously in step a.

In step f, the appropriate ω-halo-ethylphenylketone compound of structure (6) is cyanated to give the corresponding ω-halo-cyanoethylphenylketone compound of structure (21) as described previously in step b.

In step g, the appropriate ω-halo halotolylketone compound of structure (13) is cyanated to give the corresponding ω-halo cyanotolylketone compound of structure (22) as described previously in step a.

In step h, the appropriate ω-halo tolylketone compound of structure (4) is cyanated to give the corresponding ω-halo cyanotolylketone compound of structure (22) as described previously in step b.

In step i, the appropriate cyclopropyl ethylphenylketone compound of structure (7) is cyanated to give the corresponding cyclopropyl cyanoethylphenylketone compound of structure (23) as described previously in step b.

In step j, the appropriate cyclopropyl haloethylphenylketone compound of structure (14) is cyanated to give the corresponding cyclopropyl cyanoethylphenylketone compound of structure (23) as described previously in step a.

In step k, the appropriate cyclopropyl tolylketone compound of structure (5) is cyanated to give the corresponding cyclopropyl cyanotolylketone compound of structure (24) as described previously in step b.

In step 1, the appropriate cyclopropyl halotolylketone of structure (15) is cyanated to give the corresponding cyclopropyl cyanotolylketone compound of structure (24) as described previously in step a.

Starting materials for use in Scheme D are readily available to one of ordinary skill in the art.

The following examples present typical syntheses as described in Scheme D. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 6

Step a: 2-[4-(4-chloro-butyryl)-phenyl]-2-methyl-propionitirile

Dissolve 1-[4-(1-bromo-1-methyl-ethyl)-phenyl]-4-chloro-butan-1-one (2.00 g, 6.59 mmol) in anhydrous methylene chloride (20 mL) and place under an argon atmosphere. Add trimethylsilyl cyanide (1.10 mL, 8.25 mmol) followed by tin (IV) chloride (0.20 mL, 1.7 mmol) via syringe. Stir at reflux for 1 hour, add water (20 mL) and stir for an additional ½ hour. Separate the layers and extract the aqueous layer with methylene chloride. Combine the organic layers, wash with brine, dry (MgSO₄), filter and evaporate the solvent in vacuo. Purify by silica gel chromatography (15% ethyl acetate/hexane) to give the title compound as a white solid; mp 79–80° C.

EXAMPLE 7

Step 1: (4-Cyclopropanecarbonyl-phenyl)-acetonitrile

Mix (4-bromomethyl-phenyl)-cyclopropyl-methanone (5.0 g, 21 mmol), potassium cyanide (2.0 g, 30 mmol), tetra-butylammonium bromide (150 mg), water (5 mL) and acetonitrile (50 mL). Mechanically stir at room temperature for 3 hours, pour into water (450 mL) and stir overnight. Collect by filtration and recrystallize (hexane) to give the title compound as a white crystalline solid; mp 86–87° C.

The following compounds can be prepared by the-synthetic procedures depicted in Scheme D:

2-(4-Cyclopropanecarbonyl-phenyl)-propionitrile;
2-(4-Cyclopropanecarbonyl-phenyl)-2-methyl-propionitrile;
[4-(4-Chloro-butyryl)-phenyl]-acetonitrile; and
2-[4-(4-Chloro-butyryl)-phenyl]-propionitrile.

The novel intermediates of formula (II), formula (III), formula (IV), formula (V), formula (VI) and formula (VII) wherein R₅ is CN may also be prepared as described in Scheme E. In Scheme E, all substituents ate as previously defined unless otherwise indicated.

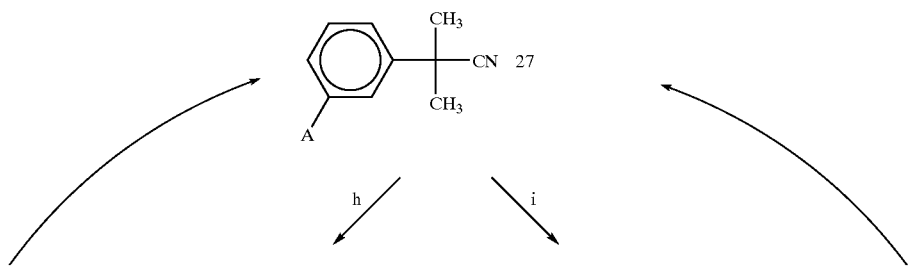

Scheme E

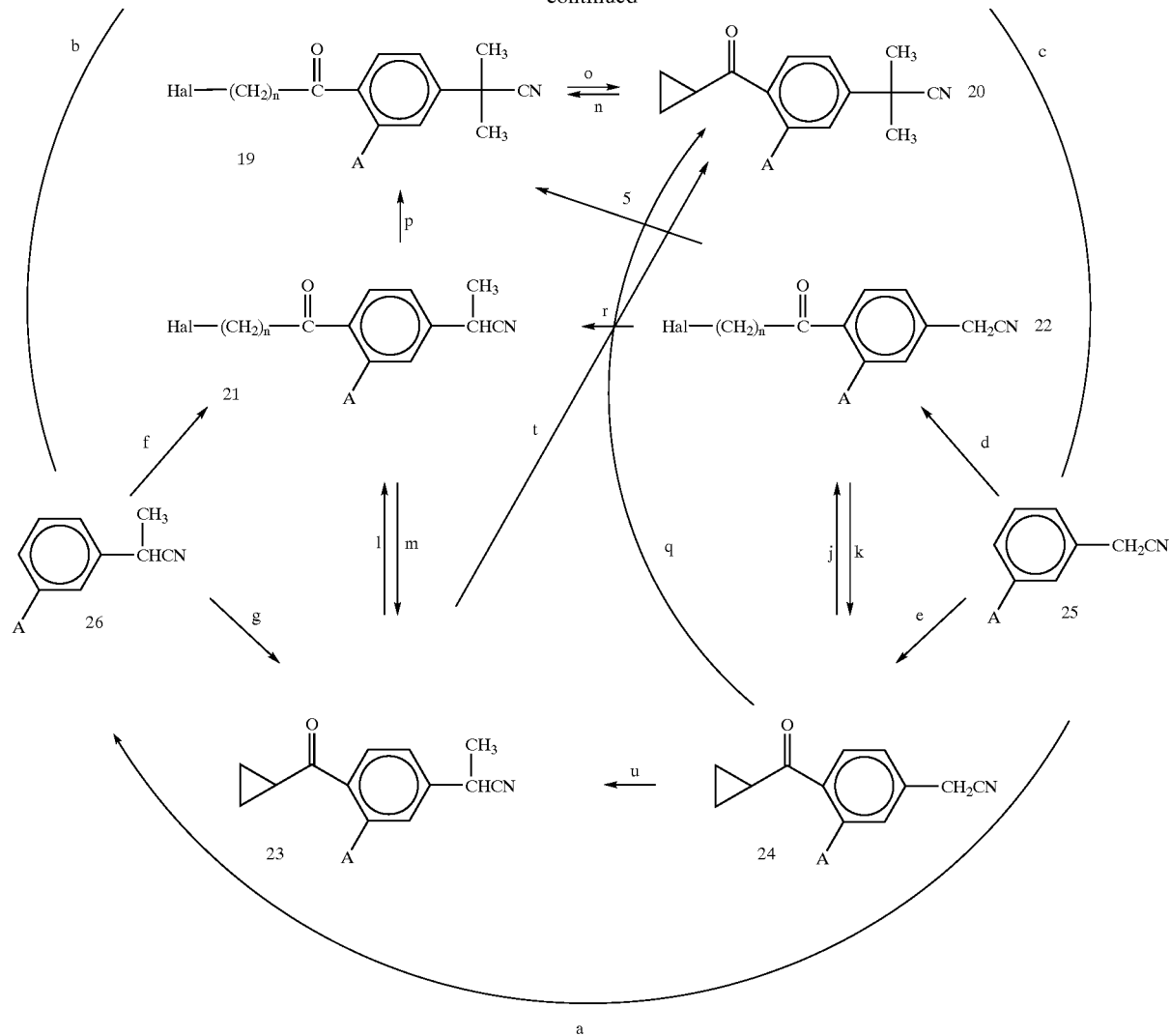

Scheme E provides alternative various general synthetic procedures for preparing the novel intermediates of formula (II), formula (III), formula (IV), formula (V), formula (VI) and formula (VII) wherein $R_5$ is CN.

In step a, the appropriate phenylacetonitrile compound of structure (25) is methylated to give the corresponding 2-cyanoethylbenzene compound of structure (26) as described previously in Scheme A, step a.

Appropriate phenylacetonitrile compounds of structure (25) may be prepared from the corresponding benzyl halide by techniques and procedures well known by one of ordinary skill in the art and described previously in Scheme D, step a.

Appropriate benzyl halide compounds may be prepared from the corresponding toluene derivative of structure (1) as described previously in Scheme B, step a.

In step b, the appropriate 2-cyanoethylbenzene compound of structure (26) is methylated to give the corresponding 2-cyano-2-propylbenzene compound of structure (27) as described previously in Scheme A, step a.

Appropriate 2-cyanoethylbenzene compound of structure (26) may be prepared from the corresponding α-methylbenzyl halide by techniques and procedures well known by one of ordinary skill in the art and as described previously in step a.

Appropriate α-methylbenzyl halide compounds may be prepared from the corresponding ethylbenzene derivative of structure (2) as described previously in Scheme B, step a.

In step c, the appropriate phenylacetonitrile compound of structure (25) is dimethylated to give the corresponding 2-cyano-2-propylbenzene compound of structure (27) as described previously in Scheme A, step c.

In step d, the appropriate phenylacetonitrile compound of structure (25) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo cyanotolylketone compound of structure (22) as described previously in Scheme A, step d.

In step e, the appropriate phenylacetonitrile compound of structure (25) is acylated with an appropriate cyclopropyl compound of the structure

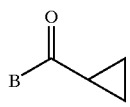

wherein B is as previously defined to give the corresponding cyclopropyl cyanotolylketone compound of structure (24) as described previously in Scheme A, step e.

In step f, the appropriate 2-cyanoethylbenzene compound of structure (26) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo-cyanoethylphenylketone compound of structure (21) as described previously in Scheme A, step d.

In step g, the appropriate 2-cyanoethylbenzene compound of structure (26) is acylated with an appropriate cyclopropyl compound of the structure

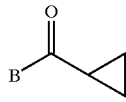

wherein B is as previously defined to give the corresponding cyclopropyl cyanoethylphenylketone compound of structure (23) as described previously in Scheme A, step e.

In step h, the appropriate 2-cyano-2-propylbenzene compound of structure (27) is acylated with an appropriate ω-halo compound of the structure Hal-$(CH_2)_n$—C(=O)—B, wherein B is Hal or hydroxy, Hal is Cl, Br or I and n is as previously defined to give the corresponding ω-halo-cyanocumylketone compound of structure (19) as described previously in Scheme A, step d.

Appropriate 2-cyano-2-propylbenzene compound of structure (27) may be prepared from the corresponding α,α-dimethylbenzyl halide by techniques and procedures well known by one of ordinary skill in the art and as described previously in step a.

Appropriate α,α-dimethylbenzyl halide compounds may be prepared from the corresponding cumene derivative of structure (3) as described previously in Scheme B, step a.

In step i, the appropriate 2-cyano-2-propylbenzene compound of structure (27) is acylated with an appropriate cyclopropyl compound of the structure

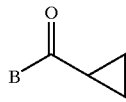

wherein B is as previously defined to give the corresponding cyclopropyl cyanocumylketone compound of structure (20) as described previously in Scheme A, step e.

In step j, the cyclopropyl functionality of the appropriate cyclopropyl cyanotolylketone compound of structure (24) is ring-opened to give the corresponding ω-halo cyanotolylketone compound of structure (22) wherein n=3 as described previously in Scheme A, step j.

In step k, the appropriate ω-halo cyanotolylketone compound of structure (22) wherein n=3 is ring-closed to give the corresponding cyclopropyl cyanotolylketone compound of structure (24) as described previously in Scheme A, step k.

In step 1, the cyclopropyl functionality of the appropriate cyclopropyl cyanoethylphenylketone compound of structure (23) is ring-opened to give the corresponding ω-halo-cyanoethylphenylketone compound of structure (21) wherein n=3 as described previously in Scheme A, step j.

In step m, the appropriate ω-halo-cyanoethylphenylketone compound of structure (21) wherein n=3 is ring-closed to give the corresponding cyclopropyl cyanoethylphenylketone compound of structure (23) as described previously in Scheme A, step k.

In step n, the cyclopropyl functionality of the appropriate cyclopropyl cyanocumylketone compound of structure (20) is ring-opened to give the corresponding ω-halo-cyanocumylketone compound of structure (19) wherein n=3 as described previously in Scheme A, step j.

In step o, the appropriate ω-halo-cyanocumylketone compound of structure (19) is ring-closed to give the corresponding cyclopropyl cyanocumylketone compound of structure (20) as described previously in Scheme A, step k.

In step p, the appropriate ω-halo-cyanoethylphenylketone compound of structure (21) is methylated to give the corresponding ω-halo-cyanocumylketone compound of structure (19) as described previously in Scheme A, step a.

In step q, the appropriate cyclopropyl cyanotolylketone compound of structure (24) is dimethylated to give the corresponding cyclopropyl cyanocumylketone compound of structure (20) as described previously in Scheme A, step c.

In step r, the appropriate ω-halo cyanotolylketone compound of structure (22) is methylated to give the corresponding ω-halo-cyanoethylphenylketone compound of structure (21) as described previously in Scheme A, step a.

In step s, the appropriate ω-halo cyanotolylketone compound of structure (22) is dimethylated to give the corresponding ω-halo-cyanocumylketone compound of structure (19) as described previously in Scheme A, step c.

In step t, the appropriate cyclopropyl cyanoethylphenylketone compound of structure (23) is methylated to give the corresponding cyclopropyl cyanocumylketone compound of structure (20) as described previously in Scheme A, step a.

In step u, the appropriate cyclopropyl cyanotolylketone compound of structure (24) is methylated to give the corresponding cyclopropyl cyanoethylphenylketone compound of structure (23) as described previously in Scheme A, step a.

Starting materials for use in Scheme E are readily available to one of ordinary skill in the art.

The following examples present typical syntheses as described in Scheme E. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "$\mu$L" refers to microliters; "$\mu$g" refers to micrograms; and "$\mu$M" refers to micromolar.

EXAMPLE 8

Step C: Cumyl Cyanide

Place phenylacetonitrile (92.3 mL, 0.800 mol), tetra n-butylammonium chloride (4.45 g of a 50% solution, 8.0 mmol) and 50% aqueous sodium hydroxide solution (2.874 mole NaOH) into a 3-neck round-bottom flask, with a thermowell, overheard stirrer, reflux condenser with a dry-ice/acetone trap and a sparge tube. Heat to 40–70 C. with stirring at 115 RPM (paddle stir blade), and bubble in methyl chloride gas (11.7 g, 0.232 mole) over a 30 minute period. Turn off the methly chloride addition and heat and stir overnight.

Sparge additional methyl chloride (35.4 g, 0.700 mol) into the reaction mixture (heated to 35 C.) over a period of 2 hours. Stir the resulting mixture at ambient temperature for 22 hours and sparge additional methyl chloride (39.5 g, 0.781 mol) into the reaction mixture at a temperature of 40–70 C. (mostly at 55–60 C.). Sparge additional methyl chloride (8.7 g, 0.172 mol) into the reaction mixture and allow to cool to 30 C. Remove the condenser and add deionized water (250 mL) and heptane (250 mL). Transfer to a separatory funnel and draw off the aqueous (bottom) layer. Wash the remining organic layer with fresh water (2×100 mL), evaporate the solvent in vacuo to give a dark red oil.

Add the oil, 50% aqueous sodium hydroxide (79 g, 0.988 mole) and tetra n-butylammonium chloride (1.0 g, 3.6 mmol) to a 500 mL 3-necked round bottom flask with a magnetic stir bar. Using the same experimental procedure described above, sparge in methyl chloride. Heat to 40–60 C., stir and sparge in methyl chloride (20.5 g, 0.40 mole) over 1 hour. Allow the reaction mixture to cool, add deionized water (100 g) and stir. Allow the layers to settle and remove the bottom layer by pipet. Repeat wash with additional water (100 g) to give the title compound as a dark orange oil (111.0 g, wet with water).

EXAMPLE 9

Step q: 2-(4-Cyclopropanecarbonyl-phenyl)-2-methyl-propionitrile

Dissolve potassium t-butoxide (2.42 g, 21.6 mmol) in diglyme (8 mL), cool to 10° C. and slowly add with mechanical stirring, a solution of (4-cyclopropanecarbonyl-phenyl)-acetonitrile (2 g, 10.8 mmol) and methyl iodide (1.5 mL, 24.0 mmol) in diglyme (10 mL). After 10 minutes, add additional potassium t-butoxide (0.3 g, 2.6 mmol) in diglyme (2 mL) and stir for a total of 45 minutes. Pour into a mixture of water (100 mL) and ethyl acetate (50 mL) and adjust the pH to 1.5–2 with dilute hydrochloric acid. Separate the organic phase and extract the aqueous phase with ethyl acetate (50 mL). Combine the organic phases and wash with brine (2×100 mL). Dry ($Na_2SO_4$), evaporate the solvent in vacuo and recrystallize (ethyl ether/hexane) to give the title compound as a yellow solid; mp 80–82° C.

The following compounds can be prepared by procedures depicted in Scheme E:

(4-Cyclopropanecarbonyl-phenyl)-acetonitrile;
2-[4-(4-chloro-butyryl)-phenyl]-2-methyl-propionitirile;
2-(4-Cyclopropanecarbonyl-phenyl)-propionitrile;
[4-(4-Chloro-butyryl)-phenyl]-acetonitrile; and
2-[4-(4-Chloro-butyryl)-phenyl]-propionitrile.

The novel intermediates of formula (II), formula (III), formula (IV), formula (V), formula (VI) and formula (VII) wherein $R_5$ is COOalkyl may also be prepared as described in Scheme F. In Scheme F, all substituents are as previously defined unless otherwise indicated.

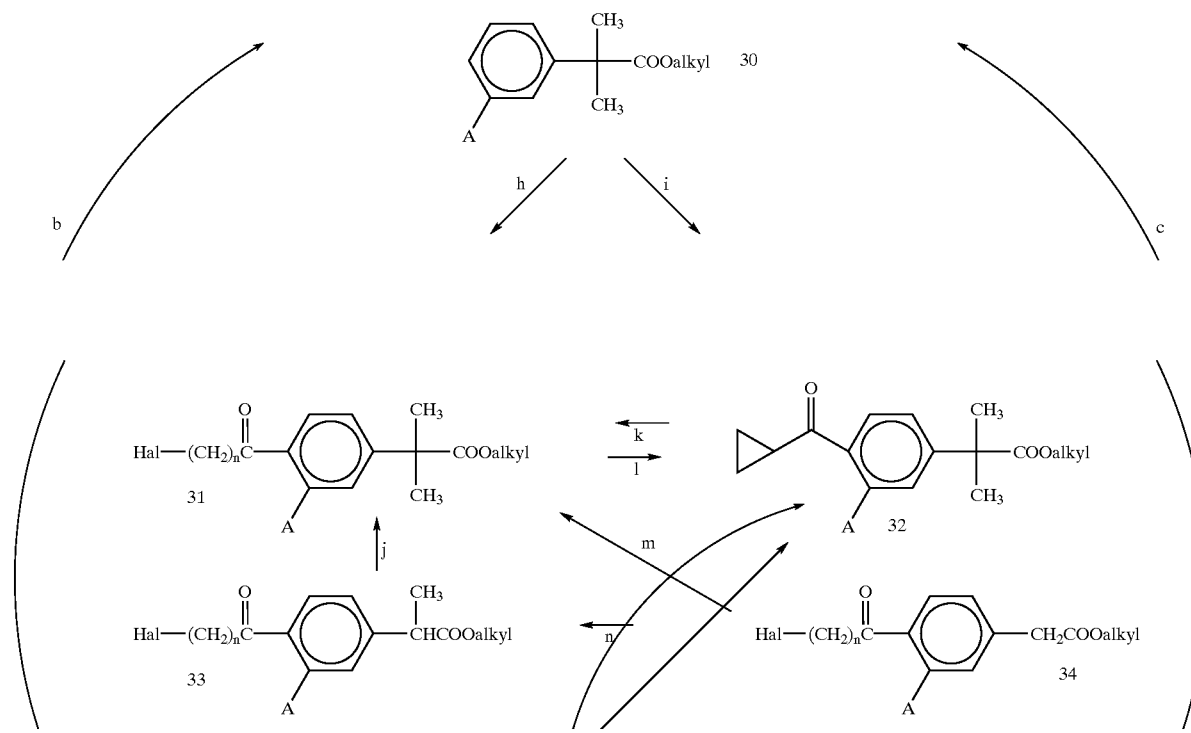

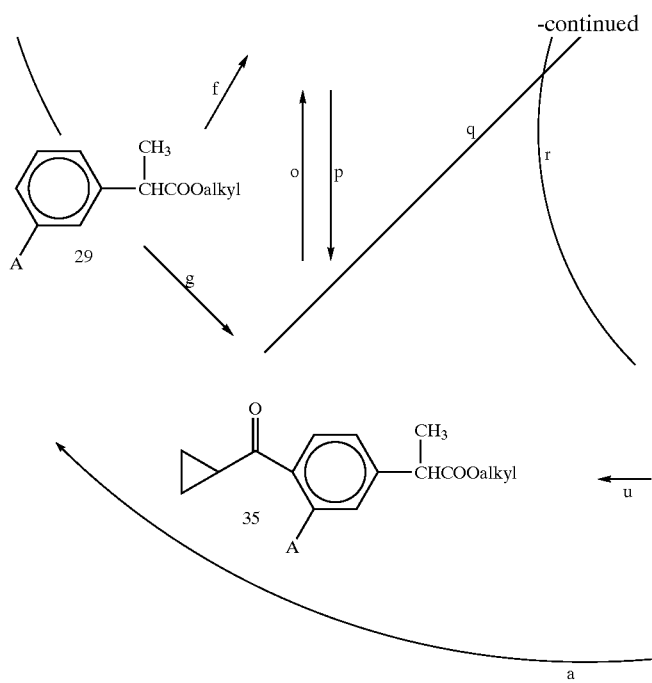
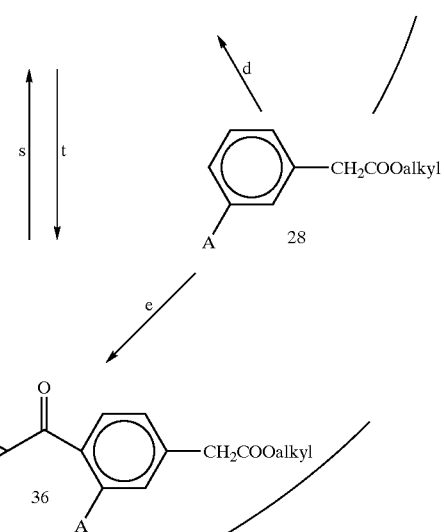

Scheme F provides alternative various general synthetic procedures for preparing the novel intermediates of formula (II), formula (III), formula (IV), formula (V), formula (VI) and formula (VII) wherein $R_5$ is COOalkyl.

In step a, the appropriate phenylacetic acid ester compound of structure (28) is methylated to give the corresponding α-methylphenylacetic acid ester compound of structure (29) as described previously in Scheme A, step a.

Appropriate phenylacetic acid ester compounds of structure (28) are prepared from the corresponding phenylacetic acid compounds by standard esterification reactions which are well known by one of ordinary skill in the art.

Appropriate phenylacetic acid compounds may be prepared by hydrolysis of the corresponding phenylacetonitrile compounds of structure (25) by techniques and procedures well known and appreciated by one of ordinary skill in the art, such as base hydrolysis. Alternatively, the phenylacetic acid compounds may be prepared by electrochemical carboxylation of the corresponding benzyl halide as described in Scheme H, step h.

In step b, the appropriate α-methylphenylacetic acid ester compound of structure (29) is methylated to give the corresponding α,α-dimethylphenylacetic acid ester compound of structure (30) as described previously in Scheme A, step a.

Alternatively α-methylphenylacetic acid ester compound of structure (29) are prepared for the corresponding α-methylphenylacetic acid compounds by standard esterification reactions which are well known by one of ordinary skill in the art as described in step a.

Appropriate α-methylphenylacetic acid compounds may be prepared by hydrolysis of the corresponding 2-cyanoethylbenzene compound of structure (26) as described previously in step a. Alternatively, the α-methylphenylacetic acid compounds may be prepared by electrochemical carboxylation of the corresponding α-methylbenzyl halide as described in Scheme H, step h.

In step c, the appropriate phenylacetic acid ester compound of structure (28) is dimethylated to give the corresponding α,α-dimethylphenylacetic acid ester compound of structure (30) as described previously in Scheme A, step c.

Alternatively α,α-dimethylphenylacetic acid ester compound of structure (30) are prepared for the corresponding α,α-dimethylphenylacetic acid compounds by standard esterification reactions which are well known by one of ordinary skill in the art as described in step a.

Appropriate α,α-dimethylphenylacetic acid compounds may be prepared by hydrolysis of the corresponding 2-cyano-2-propylbenzene compound of structure (27) as described previously in step a. Alternatively, the α,α-dimethylphenylacetic acid compounds may be prepared by electrochemical carboxylation of the corresponding α,α-dimethylbenzyl halide as described in Scheme H, step h. Appropriate α,α-dimethylbenzyl halide compounds may be prepared by hydrohalogenation of the corresponding α-methylstyrene as described previously in Scheme C, step e.

In step d, the appropriate phenylacetic acid ester compound of structure (28) is acylated with an appropriate ω-halo compound of the structure Hal-$(CH_2)_n$—C(=O)—B, wherein B is Hal or hydroxy, Hal is Cl, Br or I and n is as previously defined to give the corresponding ω'-halo-α'-keto-phenylacetic acid ester compound of structure (34) as described previously in Scheme A, step d.

In step e, the appropriate phenylacetic acid ester compound of structure (28) is acylated with an appropriate cyclopropyl compound of the structure

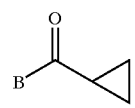

wherein B is as previously defined to give the corresponding cyclopropylketo-phenylacetic acid ester compound of structure (33) as described previously in Scheme A, step e.

In step f, the appropriate α-methylphenylacetic acid ester compound of structure (26) is acylated with an appropriate ω-halo compound of the structure Hal-$(CH_2)_n$—C(=O)—B, wherein B is Hal or hydroxy, Hal is Cl, Br or I and n is as previously defined to give the corresponding ω'-halo-α'-keto-α-methylphenylacetic acid ester compound of structure (30) as described previously in Scheme A, step d.

In step g, the appropriate α-methylphenylacetic acid ester compound of structure (29) is acylated with an appropriate cyclopropyl compound of the structure

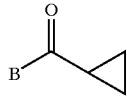

wherein B is as previously defined to give the corresponding cyclopropylketo-α-methylphenylacetic acid ester compound of structure (35) as described previously in Scheme A, step e.

In step h, the appropriate α,α-dimethylphenylacetic acid ester compound of structure (30) is acylated with an appropriate ω-halo compound of the structure Hal-$(CH_2)_n$—C(=O)—B, wherein B is Hal or hydroxy, Hal is Cl, Br or I and n is as previously defined to give the corresponding ω'-halo-α'-keto-α,α-di-methylphenylacetic acid ester compound of structure (31) as described previously in Scheme A, step d.

Appropriate α,α-dimethylphenylacetic acid ester compound of structure (30) are prepared for the corresponding α,α-dimethylphenylacetic acid compounds by standard esterification reactions which are well known by one of ordinary skill in the art as described in step a.

Appropriate α,α-dimethylphenylacetic acid compounds may be prepared by hydrolysis of the corresponding 2-cyano-2-propylbenzene compound of structure (27) as described previously in step a.

In step i, the appropriate α,α-dimethylphenylacetic acid ester compound of structure (30) is acylated with an appropriate cyclopropyl compound of the structure

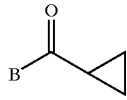

wherein B is as previously defined to give the corresponding cyclopropylketo-α,α-dimethylphenylacetic acid ester compound of structure (32) as described previously in Scheme A, step e.

In step j, the appropriate ω'-halo-α'-keto-α-methylphenylacetic acid ester compound of structure (33) is methylated to give the corresponding ω'-halo-α'-keto-α,α-di-methylphenylacetic acid ester compound of structure (32) as described previously in Scheme A, step a.

In step k, the cyclopropyl functionality of the appropriate cyclopropylketo-α,α-dimethylphenylacetic acid ester compound of structure (32) is ring-opened to give the corresponding ω'-halo-α'-keto-α,α-di-methylphenylacetic acid ester compound of structure (31) wherein n=3 as described previously in Scheme A, step j.

The resulting ω'-halo-α'-keto-α,α-di-methylphenylacetic acid ester compound of structure (31) wherein n=3 may be purified by distillation and/or crystallization. methylphenylacetic acid ester compound of structure (31) wherein n=3 is ring-closed to give the corresponding cyclopropylketo-α,α-dimethylphenylacetic acid ester compound of structure (32) as described previously in Scheme A, step k.

The resulting cyclopropylketo-α,α-dimethylphenylacetic acid ester compound of structure (32) may be purified by distillation and/or crystallization. Additional cyclopropylketo-α,α-dimethylphenylacetic acid ester compound of structure (32) may be recovered from the mother liquors of the crystallization by distillation.

Alternatively, additional ω'-halo-α'-keto-α,α-dimethylphenylacetic acid ester compound of structure (31) wherein n=3 may be recovered from the mother liquors of the crystallization by ring-closure as described in step 1 to give the corresponding cyclopropylketo-α,α-dimethylphenylacetic acid ester compound of structure (32), purifying cyclopropylketo-α,α-dimethylphenylacetic acid ester compound of structure (32) by distillation, ring-opening the purified cyclopropylketo-α,α-dimethylphenylacetic acid ester compound of structure (32) as described previously in step k to give the purified ω'-halo-α'-keto-α,α-di-methylphenylacetic acid ester compound of structure (31).

In step m, the appropriate ω'-halo-α'-keto-phenylacetic acid ester compound of structure (34) is dimethylated to give the corresponding ω'-halo-α'-keto-α,α-di-methylphenylacetic acid ester compound of structure (31) as described previously in Scheme A, step c.

In step n, the appropriate ω'-halo-α'-keto-phenylacetic acid ester compound of structure (34) is methylated to give the corresponding ω'-halo-α'-keto-α-methylphenylacetic acid ester compound of structure (33) as described previously in Scheme A, step a.

In step o, the cyclopropyl functionality of the appropriate cyclopropylketo-α-methylphenylacetic acid ester compound of structure (35) is ring-opened to give the corresponding ω'-halo-α'-keto-α-methylphenylacetic acid ester compound of structure (33) wherein n=3 as described previously in Scheme A, step j.

In step p, the appropriate ω'-halo-α'-keto-α-methylphenylacetic acid ester compound of structure (33) wherein n=3 is ring-closed to give the corresponding cyclopropylketo-α-methylphenylacetic acid ester compound of structure (35) as described previously in Scheme A, step k.

In step q, the appropriate cyclopropylketo-α-methylphenylacetic acid ester compound of structure (35) is methylated to give the corresponding cyclopropylketo-α,α-dimethylphenylacetic acid ester compound of structure (32) as described previously in Scheme A, step a.

In step r, the appropriate cyclopropylketo-phenylacetic acid ester compound of structure (36) is dimethylated to give the corresponding cyclopropylketo-α,α-dimethylphenylacetic acid ester compound of structure (32) as described previously in Scheme A, step c.

In step s, the cyclopropyl functionality of the appropriate cyclopropylketo-phenylacetic acid ester compound of structure (36) is ring-opened to give the corresponding ω'-halo-α'-keto-phenylacetic acid ester compound of structure (34) wherein n=3 as described previously in Scheme A, step j.

In step t, the appropriate ω'-halo-α'-keto-phenylacetic acid ester compound of structure (34) wherein n=3 as is ring-closed to give the corresponding cyclopropylketo-phenylacetic acid ester compound of structure (36) as described previously in Scheme A, step k.

In step u, the appropriate cyclopropylketo-phenylacetic acid ester compound of structure (36) is methylated to give the corresponding cyclopropylketo-α-methylphenylacetic acid ester compound of structure (35) as described previously in Scheme A, step a.

Starting materials for use in Scheme F are readily available to one of ordinary skill in the art.

The following examples present typical syntheses as described in Scheme F. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 10

Step c: 2-Methyl-2-phenylpropionate, Methyl Ester

Equip a two liter, 3-necked, round bottom flask with a thermowell with a thermometer, heating mantle, mechanical agitator, gas inlet for MeCl, rubber septum for sampling by syringe and a cryoscopic condensing system. The condensing system is composed of an 18 inch inner helical coil/outer jacket condenser chilled to −50 C. with refrigerated acetone topped with a dry ice cold finger having approximately 100 square inches of chilled surface area. The cold finder is vented through a drying tube filled with drying agent and MeCl is supplied from a lecture bottle mounted on a digital balance. The feed rate can be accurately controlled using a needle valve and monitored by rotomter. The rotometer is calibrated with MeCl to give an average response of 2.5 mg/min/scale division. Phenylacetic acid, ethyl ester is supplied via 1/16 inch stainless steel tubing inserted through the rubber sampling septum by a HPLC pump from a 1 liter bottle mounted on a digital balance. The bottle is sealed with a septum and vented through a drying tube filled with drying agent. The temperature is controlled using a thermowatch to regulate the heating mantle. If cooling is required, it is accomplished either by immersing the reaction flask in a water bath or simply by removing the mantle.

The phenylacetic acid, ethyl ester pump is primed with phenylacetic acid containing 1 st % t-butanol and the phenylacetic acid, ethyl ester balance is zeroed. The MeCl balance is zoned and a 200 g sample of 60% NaH is weighed into a wide mouth plastic jar in a nitrogen filled glove bag and is transferred to the reaction vessel through a funnel (sampling septum is removed). Through the same funnel is added anhydrous glyme (800 mL) and the septum (pierced by the 1/16 inch phenylacetic acid, ethyl ester feed tube) is replaced. The mixture is agitated and heated to 50 C. while MeCl (40 g) is introduced. When the reaction mixture reaches 50 C., the continuous addition of phenylactic acid, ethyl ester/t-butanol at 1 mL/min and MeCl at approximately 0.62 g/min. is initiated. Samples of about p.1 mL are withdrawn at intervals using a disposable syringe fitted with an 8 inch needle. A portion of the sample (5–15 drops depending on the accumulation of product) is dissolved in 25% aqueous acetonitrile (5 mL) and analyzed immediately. The reaction is continued for an additional 2 hours at 50 C. and then at ambient temperature overnight.

In the apparatus described above, agitate NaH (180 g of 60%) and anhydrous glyme (800 mL) and heat to 50 C. Add MeCl (52 g) along with methyl phenylacetate (20 g). Stir for 1 hour at 50 C., then add, by continuous addition, methyl phenylacetate (0.8 mL/min) and MeCl approximately 0.53 g/min). Stir for 1 hour, stop the additoina and continue heating for 1.5 hours. Resume the additions and run for 45 minutes. Allow to agitate at ambient temperature overnight. Heat the reaction to 50 C. and resume the addition of methyl phenylacetate (0.4 mL/min) and MeCl (approximately 0.27 g/min). When a total of 246 g of methyl phenylacitate has been added, stop the addition and agitate overnight. Distill the glyme at 1 atm. until the pot temperature reaches 125 C. Cool the residue and pour into water (1 L) containing acetic acid (100 mL). Filter through filter aid and separate the phases. Distill the organic phase through a 10-plate Oldershaw column fitted with a reflux splitting head at 4 mm Hg. Collect 10 mL at a 5:2 reflux ratio and discard. Collect the title compound at a 2:1 reflux ratio and head temperature of 93 C. (100 g).

EXAMPLE 11

Step d: [4-(4-Chloro-butyryl)-phenyl]-acetic Acid, Ethyl Ester and [3-(4-Chloro-butyryl)-phenyl]-acetic Acid, Ethyl Ester Method A: Load a 3-neck flask with sublimed AlCl$_3$ (293 g, 2.08 mmol) and heptane (400 mL). Cool to below 5° C. and slowly add chlorobutyryl chloride (125 mL), keeping the temperature below 5° C. Add phenylethyl acetate (160 mL), keeping the temperature below 10 C. and stir overnight. Decant the heptane layer and dissolve the residue in methylene chloride (400 mL). Slowly pour the-methylene chloride solution into a mixture of concentrated hydrochloric acid (200 mL) and cracked ice. Separate the organic phase, wash with water 1 L), followed by 5% sodium hydrogen carbonate (1 L). Evaporate the solvent in vacuo to give a red oil (243 g).

Dissolve the red oil (243 g) in methylene chloride (250 mL) and sparge with hydrogen chloride gas for 1.5 hours and evaporate the solvent in vacuo to give the title compound as a 50:50 mixture of para and meta isomers (243 g).

Method B: Place aluminum chloride (293 g) and methylene chloride (300 mL) in a 1L, 3-neck round bottom flask with a thermowell and equipped with a thermomter, mechanical stirrer, reflux condenser, equilibrating dropping funnel and ice bath. Cool to 10 C. and add, by dropwise addition, 4-chlorobutyryl chloride (169 g), keeping the temperature below 10 C. After addition is complete, add, by dropwise addition, phenylethyl acetate (164 g), keeping the temperature below 10 C. Heat the reaction to 40 C. for 16 hours, slowly pour into a mechanically agistated 4 L beaker containing ice/water (2000 g) and stir for 1 hour. Separate the layers, extract the water phase with methylene chloride (50 mL), filter the combined organic phases through a ¼ inch thick bed of filter aid and extract eequentially with water (100 mL) and 10 wt % Na2CO3 (200 mL). Re-extract the cargbonate solution with fresh methylene chloride (50 mL) and wash the combined methylene chloride solutions with water (100 mL). Distill off solvent at atmospheric pressure until the pot temperature reaches 120 C. Cool the residue and dilute with 2B absolute ethanol (200 mL). Heat the solution to 70 C. and sparge in anhydrous HCl (20 g) over 10 minutes. After 40 minutes, cool the reaction and hold overnight under nitrogen. Evaporate the solvent in vacuo to give the title compound (258 g).

EXAMPLE 12

Step k: 2-[4-(4-Chloro-butyryl)-phenyl]-2-methyl-propionic Acid, Ethyl Ester

Method A: Dissolve 2-(4-cyclopropanecarbonyl-phenyl)-2-methyl-propionic acid, ethyl ester (100 g) in xylene (500 mL) and ethanol (100 mL) and heat to 70° C. Sparge the atmosphere of the reaction with hydrogen chloride gas (24.6 g) over 220 hours. Evaporate the solvent in vacuo to give the title compound.

Method B: Add a solution of 5M HCl in acetonitrile (50 mL, 9 g of HCl, 247 mmol) to 2-(4-cyclopropanecarbonylphenyl)-2-methyl-propionic acid, ethyl ester (25.5 g, 98 mmol) and seal in a 100 mL flask with a rubber septum. Heat to 50° C. for 4 hours, dilute with toluene (50 mL), wash with water (50 mL), aqueous 10% Na2CO3 (50 mL) and then water (50 mL). Evaporate the solvent in vacuo to give the title compound as an oil (27.2 g).

Method C: Place 2-(4-cyclopropanecarbonyl-phenyl)-2-methyl-propionic acid, ethyl ester (86 g, 330 mmol) and dry acetonitrile (70 mL) in a 250 mL 3-neck round-bottom flask equipped with a magnetic stirbar, thermometoer, gas inlet and distillation head connected to a balloon by way of a T fitting for pressure control. Slowly warm the reaction mixture with stirring to 60° C. while sparging excess HCl into the reaction mixture for 6 hours, dilute with toluene (50 mL), wash with water (50 mL), aqueous 10% Na2CO3 (50 mL) and then water (50 mL). Evaporate the solvent in vacuo to give the title compound.

Method D: Place 2-(4-cyclopropanecarbonyl-phenyl)-2-methyl-propionic acid, ethyl ester (91 g, 350 mmol) in a 1 L 3-neck round-bottom flask equipped with a magnetic stirbar, thermometer, gas inlet, and distillation head connected to a balloon by way of a T fitting for pressure control. Slowly sparge in anhydrous HCl, keeping the balloon slightly inflated. After 10 minutes, add acetonitrile (590 mL), heat to 65° C. and add excess HCl over 7 hours. Heat the mixture and remove acetonitrile/HCl overhead. After 500 mL of acetonitrile is removed, add mixed xylene (200 mL) and continue the distillation. Add additional xylene (200 m) and after a total of 640 mL of solvent has been removed (pot=130° C. and overhead=130° C.), add ethanol 2B (100 mL). Remove the ethanol by distillation to give the title compound as a oil (330 g).

Method E: Place 2-(4-cyclopropanecarbonyl-phenyl)-2-methyl-propionic acid, ethyl ester (98 g, 410 mmol) and xylenes (600 mL) in a 1 L 3-neck round-bottom flask equipeed with a magnetic stirbar, thermometer, gas inlet and distillation head connected to a balloon by way of a T fitting for pressure control. Heat the reaction mixture to 80° C. and slowly sparge in anhydrous HCl. After 100 minutes, add ethanol 2B (100 mL) and HCl (26 g) and heat to 35° C. for 2 hours. Remove the ethanol and HCl by distillation with aspirator vacuum (pot=35° C., overhead=30° C.) to give the title compound as a solution in xylene.

Method F: Place 2-(4-cyclopropanecarbonyl-phenyl)-2-methyl-propionic acid, ethyl ester (500 g) in a 4L Hastelloy reactor equipped with a gas inlet, overhead stirrer, temperature control and dip pipe for sampling. Heat the oil to 60 C. and evacuate the head space. Add HCl raising the pressure to 10psig and react for 80–300 minutes. Vent the excess HCl and sparge the oil with nitrogen for 5 minutes to give the title compound.

Method G: Fit a 2 L 3-neck round bottom flask with an overhead paddle stirrer, a gas sparge tube (with fritted end to disperse gas) and a reflux condenser (with drying tube on top, filled with drying agent). Fit the bottom of the flask with a heating mantle and put 2-(4-cyclopropanecarbonyl-phenyl)-2-methyl-propionic acid, ethyl ester (78.10 g, 0.300 mol), xylenes (400 mL) and absolute 2B ethanol (90 mL) into the flask. Stir to dissolve all the solids at ambient temperature. Sparge hydrogen chloride from a lecture bottle (38.36 g, 1.052 mol) into the stirred solution without external heating over a 15 minute period. Replace the sparge tube with a glass stopper and heat the solution by mantle, with stirring, at 40–79 C. for 45 minutes and 79 C. for 15 minutes. Replace the reflux condenser with a simple still head fitted with a thermometer and condenser. Collect 200 mL of distillate (80–138 C. at atmospheric pressure) and allow the remaining light yellow solution to cool to give a mixture of the title compound and xylenes.

EXAMPLE 13

Step t: (4-Cyclopropanecarbonyl-phenyl)-acetic Acid, Ethyl Ester and (3-Cyclopropanecarbonyl-phenyl)-acetic Acid, Ethyl Ester Dissolve the mixture of [4-(4-chloro-butyryl)-phenyl]-acetic acid, ethyl ester and [3-(4-chloro-butyryl)-phenyl]-acetic acid, ethyl ester (650 g) in 2B ethanol (1250 mL). Add, by dropwise addition, a solution of 2B ethanolic KOH (168 g in 1000 mL), keeping the temperature below 10 C. After the addition, stir magnetically for 5 hours at −10 C. Bring the mixture to pH 6 with acetic acid (5 mL) and filter through a celite pre-coat. Evaporate the solvent in vacuo to give the title compound as an oil (538 g).

EXAMPLE 14

Step d: [4-(4-Chloro-butyryl)-phenyl]-acetic Acid, 2-ethylhexyl Ester

Mix 2-ethyl-1-hexanol (6.5 g, 5 mol), triethylamine (50.5 g, 0.5 mol) and methylene chloride (50 mL). Add, by dropwise addition, 2-phenylacetyl chloride (5 mol) and warm to 50° C. Stir at room temperature overnight, filter and wash the filtercake with methylene chloride (50 mL). Combine the organic phases and wash with 5% aqueous hydrochloric acid (50 mL) and water. Dry (MgSO$_4$), evaporate the solvent in vacuo and purify by distillation to give 2-phenylacetic acid, 2-(2-ethylhexy)l ester.

Mix chlorobutyryl chloride (16.9 g) and AlCl$_3$ (29.3 g) at room temperature. Add 2-phenylacetic acid, 2-ethylhexyl ester (27.6 g), keeping the temperature below 10° C. Heat at 35° C. for 24 hours, quench in ice water (200 g). Separate the organic phase, dry (MgSO$_4$) and evaporate the solvent in vacuo. Dilute the residue with ethanol (150 mL), add hydrogen chloride (5 g) and heat to 75° C. After 2.5 hours, add another 5 g of hydrogen chloride and stir at 75° C. for 24 hours. Evaporate the solvent in vacuo to give the title compound.

EXAMPLE 15

Step h: 2-[4-(4-Chloro-butyrl)-phenyl]-2-methyl-proprionic Acid, Ethyl Ester and 2-[3-(4-Chloro-butyrl)-phenyl]-2-methyl-proprionic Acid, Ethyl Ester Method A: Place aluminum chloride (58.4 g, 438 mmol) and methylene chloride (100 mL) in a 250 mL 3 neck flask equipped with a condenser, thermometer, and overhead stirrer. Cool to 10 C. and add, by dropwise addition, 4-chlorobutyryl chloride (32.4 g, 230 mmol), keeping the temperature below 10 C. Add, by dropwise addition, ethyl dimethylphenylacetate (40 g, 208 mmol) at 10 C. After the addition, slowly warm the mixture to room temperature and then heat at reflux for 17 hours. Quench the reaction into ice (400 g) and stir for 1 hour. Extract with methylene chloride (2×25 mL), wash with water (25 mL), 10% aqueous sodium carbonate (25 mL) and water (25 mL). Evaporate the solvent in vacuo to give a red oil (58.7 g).

Dissolve the red oil (58.7 g) in 2B ethanol (40 mL) and place in a 250 mL round bottom flask equipped with an overhead stirrer, condenser, thermometer and gas inlet tube. Add anhydrous HCl (3 g. 80 mmol) with vigorous stirring and heat to 70 C. for 1 hour. Evaporate the solvent in vacuo to give the title compound as a yellow oil (59 g).

Method B: Place AlCl₃ (146.5 g. 1.1 mol) and methylene chloride (75 mL) in a 3-neck, 500 mL round-bottomed flack equipped with an overhead stirrer, bottom drop valve, thermometer, condenser and temperature control and cool to 15° C. Add, by dropwise addition, 4-chlorobutyryl chloride (84.5 g, 0.6 mol), keeping the temerature below 15° C. Add, by dropwise addition, ethyl 2-methyl-2-phenylpropionate (96 g, 0.5 mol), keeping the temperature below 15° C. After addition is complete, stir the reaction mixture at 22° C. for 1 hour, then heat at reflux (57° C.) for 2 hours. Add the reaction mixture, by dropwise addition, by way of the bottom drop valve, to water (500 mL) at 95° C. contained in a 2 L 3 neck flask equipped with a magnetic stirbar, thermometer and distillation head. During addition, hold the reaction mixture at 70° C. by allowing the methylene chloride to distill overhead. After the quench is complete, separate the the organic layer, dry (MgSO₄) and evaporate the solvent in vacuo to give the title compound (150 g).

EXAMPLE 16

Step h: 2-[4-(4-Chloro-butyrl)-phenyl]-2-methyl-proprionic Acid, Methyl Ester

Method A: Mix AlCl₃ (128 g) and methylene chloride (66 mL) and cool with a dry ice/acetone bath to −15 C. Add, by dropwise addition, 4-chlorobutyryl chloride (73.8 g), keeping the temperature below 15 C. Add, by dropwise addition, methyl 2-methyl-2-phenylpropionate (77.8 g), keeping the temperature below 15 C. After addition is complete, stire the reaction mixture at 22 C. for 10 minutes, then heat to 45 C. for 3 hours. Quench into ice/water (875 g), filter through filter aid, separate the layers and wash the aqueous phase with methylene chloride (50 mL). Combine the organics and evaporate the solvent in vacuo to give 131 g. Decant solids off and place the oil? in a 500 mL 3-neck flask along with methanol (150 mL). Purge with HCl and heat at reflux for 1 hour and allow to stand overnight. Evaporate the solvent in vacuo, dissolve in methylene chloride (250 mL), wash with water (200 mL) and NaHCO3 (300 mL). Evaporate the solvent in vacuo to give a mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately m:p 50:50) (121 g).

Place the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately m:p 50:50) (40.1 g) in a 250 mL, 3-necked flask with a mechanical agitator, N₂ blanket and cooling bath. Add methanol (80 mL) at room temperature and cool to −5 C. with and ice/acetone/water bath. Seed with 2-[4-(4-chloro-butyrl)-phenyl]-2-methyl-proprionic acid, methyl ester and allow to stand at −5 C. for 1 hour. Cool to −10 C. with ice/acetone and allow to stand for 1.5 hours. Cool to −16 C. and hold for 30 minutes. Vacuum filter through a 60 mL sintered glass jacketed filter funnel chilled to −10 C. Wash the filtercake with cold (−50 C.) methanol (30 mL) and cold (−50 C.) n-pentane (30 mL). Dry the filtercake briefly in a stream of nitrogen and vacuum dry (20 C. at 15 mm Hg) to give the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately m:p 10:90) (10.5 g).

Dissolve the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately m:p 10:90) in methanol (30 mL), cool to 10 C. in an ice/water bath and seed with 2-[4-(4-chloro-butyrl)-phenyl]-2-methyl-proprionic acid, methyl ester. Cool to 0 C. and hold for 20 minutes. Vacuum filter, wash and dry as above to give the title compound (5.6 g) as an off-white solid; mp 29.5–30.5 C.

Method B: Mix AlCl₃ (128 g) and methylene chloride (66 mL) and cool with a dry ice/acetone bath to −15 C. Add, by dropwise addition, 4-chlorobutyryl chloride (73.8 g), keeping the temperature below 15 C. Add, by dropwise addition, methyl 2-methyl-2-phenylpropionate (77.8 g), keeping the temperature below 15 C. After addition is complete, stire the reaction mixture at 22 C. for 10 minutes, then heat to 45 C. for 3 hours. Quench into ice/water (875 g), filter through filter aid, separate the layers and wash the aqueous phase with methylene chloride (50 mL). Combine the organics and evaporate the solvent in vacuo to give 131 g. Decant solids off and place the oil in a 500 mL 3-neck flask along with methanol (150 mL). Purge with HCl and heat at reflux for 1 hour and allow to stand overnight. Evaporate the solvent in vacuo, dissolve in methylene chloride (250 mL), wash with water (200 mL) and NaHCO₃ (300 mL). Evaporate the solvent in vacuo to give a mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (121 g) (approximately 50:50 m:p).

Place the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately 50:50 m:p) (40.1 g) is a 250 mL, 3-necked flask with a mechanical agitator, N₂ blanket and cooling bath. Add methanol (80 mL) at room temperature and cool to −5 C. with and ice/acetone/water bath. Seed with 2-[4-(4-chloro-butyrl)-phenyl]-2-methyl-proprionic acid, methyl ester and allow to stand at −5 C. for 1 hour. Cool to −10 C. with ice/acetone and allow to stand for 1.5 hours. Cool to −16 C. and hold for 30 minutes. Vacuum filter through a 60 mL sintered glass jacketed filter funnel chilled to −10 C. Wash the filtercake with cold (−50 C.) methanol (30 mL) and cold (−50 C.) n-pentane (30 mL). Dry the filtercake briefly in a stream of nitrogen and vacuum dry (20 C. at 15 mm Hg) to give the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately 10:90 m:p) (10.5 g).

To the methanol solution of the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately 50:50 m:p) (approximately 70:30 m:p) from crystallization (i.e. mother liquor), slowly add 1 to 1.2 euivalents of 25% NaOMe/MeOH solution. Agitate for approximately 30 minutes at 25 C. Neutralize the excess NaOMe with excess carbon dioxide. Add water (300 mL) per mole of subtrate, evaporate the methanol by vacuum distisallation and decant the aqueous layer to give a mixture of 2-(4-cyclopropanecarbonyl-phenyl)-2-methyl-propionic acid, methyl ester and 2-(3-cyclopropanecarbonyl-phenyl)-2-methyl-propionic acid, methyl ester (approximately 70:30 m:p).

Distill the mixture of 2-(4-cyclopropanecarbonyl-phenyl)-2-methyl-propionic acid, methyl ester and 2-(3-cyclopropanecarbonyl-phenyl)-2-methyl-propionic acid, methyl ester (approximately 70:30 m:p) at 0.5 mm Hg and discard a light fraction boiling at 25–130 C. (pot temp −105–165 C.). Continue distilling the oil at 0.5 mm Hg and collect a second fraction boiling at 130–150 C. (pot temperature 165–190) to give the mixture of 2-(4-cyclopropanecarbonyl-phenyl)-2-methyl-propionic acid, methyl ester and 2-(3-cyclopropanecarbonyl-phenyl)-2-methyl-propionic acid, methyl ester (approximately 70:30 m:p)

Pack a ³¹⁄₃₂ in. I.D. vacuum jacked and silvered column with 53 inches of 1 in. diameter, 316 stainless steel packing. For high temperature distillation, the column is fitted with an adiabatic jacket composed of an inner layer of 1 in. fiber glass wrapped with heat tape in an upper and lower zone and finally covered with 2 in. fiber glass insulation. The upper zone is heated at 135 C. and the lower zone at 185 C. The magnetic reflux splitting head is controlled by a reflux timer and fitted with a standard thermometer for monitoring overhead temperature. Vacuum is supplied by a system composed of a pump protected by a dry ice trap and fitted with a McLeod gage for monitoring the overhead pressure. The 1 L distillation pot is heated with an electric mantel at 65 volts, agitated magnetically and fitted with a mercury manometer for monitoring bottoms pressure, and a thermocouple for monitoring bottoms temperature.

The still pot is charged with 265 g each of m- and p-xylene and fitted with a rubber septum for sampling by syringe. The xylene mixture is heated at total reflux-and atmosphere pressure with the temperature 135 C. at the head and 139 C. in the bottoms. Samples are withdrawn for analysis by collecting a few drops of distillate and extracting about 1mL from the pot. The still is sampled after 3 hours and again after 18 hours for calibration by GC and theoretical plate calculations using the Fenske correlation and a relative volatility, α=1.0209.

Charge the mixture of 2-(4-cyclopropanecarbonyl-phenyl)-2-methyl-propionic acid, methyl ester and 2-(3-cyclopropanecarbonyl-phenyl)-2-methyl-propionic acid, methyl ester (approximately 70:30 m:p) to the still pot and neat at total reflux until the column has equilibrated. Take a forecut at 2:1 reflux ratio and increase the reflux ratio to 5:1 and the 2-(3-cyclopropanecarbonyl-phenyl)-2-methyl-propionic acid, methyl ester stripped. Cool and release vacuum and allow to sit overnight. Add bis(2-ethylhexyl) phthalate (dioctyl phthalate) (100 mL) to the still pot and restart the still as before. Once the still has equilibrated, collect mixed fractions of 2-(4-cyclopropanecarbonyl-phenyl)-2-methyl-propionic acid, methyl ester and 2-(3-cyclopropanecarbonyl-phenyl)-2-methyl-propionic acid, methyl ester at 50:50 reflux ratio.

Place the mixture of 2-(4-cyclopropanecarbonyl-phenyl)-2-methyl-propionic acid, methyl ester and 2-(3-cyclopropanecarbonyl-phenyl)-2-methyl-propionic acid, methyl ester (approximatelty m:p 50:50) (330 mmol) and dry acetonitrile (70 mL) in a 250 mL 3-neck round-bottom flask equipped with a magnetic stirbar, thermometoer, gas inlet and distillation head connected to a balloon by way of a T fitting for pressure control. Slowly warm the reaction mixture with stirring to 60° C. while sparging excess HCl into the reaction mixture for 6 hours, dilute with toluene (50 mL), wash with water (50 mL), aqueous 10% Na2CO3 (50 mL) and then water (50 mL). Evaporate the solvent in vacuo to give the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (121 g) (approximately 50:50 m:p).

Place the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately 50:50 m:p) (40.1 g) in a 250 mL, 3-necked flask with a mechanical agitator, $N_2$ blanket and cooling bath. Add methanol (80 mL) at room temperature and cool to −5 C. with and ice/acetone/water bath. Seed with 2-[4-(4-chloro-butyrl)-phenyl]-2-methyl-proprionic acid, methyl ester and allow to stand at −5 C. for 1 hour. Cool to −10 C. with ice/acetone and allow to stand for 1.5 hours. Cool to −16 C. and hold for 30 minutes. Vacuum filter through a 60 mL sintered glass jacketed filter funnel chilled to −10 C. Wash the filtercake with cold (−50 C.) methanol (30 mL) and cold (−50 C.) n-pentane (30 mL). Dry the filtercake briefly in a stream of nitrogen and vacuum dry (20 C. at 15 mm Hg) to give the mixture of 2-[4-(4-chloro-butyrl)-phenyl]-2-methyl-proprionic acid, methyl ester and 2-[3-(4-chloro-butyrl)-phenyl]-2-methyl-proprionic acid, methyl ester (approximately 10:90 m:p) (10.5 g).

Dissolve the mixture of 2-(4-cyclopropanecarbonyl-phenyl)-2-methyl-propionic acid, methyl ester and 2-(3-cyclopropanecarbonyl-phenyl)-2-methyl-propionic acid, methyl ester (approximately 10:90 m:p) in methanol (30 mL), cool to 10 C. in an ice/water bath and seed with 2-[4-(4-chloro-butyrl)-phenyl]-2-methyl-proprionic acid, methyl ester. Cool to 0 C. and hold for 20 minutes. Vacuum filter, wash and dry as above to give the title compound (5.6 g) as an off-white solid; mp 29.5–30.5 C.

EXAMPLE 17

Step 1: 2-(4-Cyclopropanecarbonyl-phenyl)-2-methyl-propionic Acid, Ethyl Ester

Dissolve a mixture of 2-[4-(4-chloro-butyryl)-phenyl]-2-methyl-proprionic acid, ethyl ester and 2-[3-(4-chloro-butyryl)-phenyl]-2-methyl-proprionic acid, ethyl ester (59 g) in 2B ethanol (100 mL) and add, by dropwise addition, a solution of KOH (49.4 g of 85%) in 2B ethanol (250 mL), keeping the temperature below 15 C. After the addition, warm the reaction mixture to room temperature and stir magentically for 1 hour. Bring to pH 6 with acetic acid and filter through a celite pre-coat. Evaporate the solvent in vacuo to give a mixture of 2-(4-cyclopropanecarbonyl-phenyl)-2-methyl-propionic acid, ethyl ester and 2-(3-cyclopropanecarbonyl-phenyl)-2-methyl-propionic acid, ethyl ester as an oil (57.1 g) Purify by one of the following methods:

Method A: Pack a ³¹⁄₃₂ in. I.D. vacuum jacked and silvered column with 53 inches of 1 in. diameter, 316 stainless steel packing. For high temperature distillation, the column is fitted with an adiabatic jacket composed of an inner layer of 1 in. fiber glass wrapped with heat tape in an upper and lower zone and finally covered with 2 in. fiber glass insulation. The upper zone is heated at 135 C. and the lower zone at 185 C. The magnetic reflux splitting head is controlled by a reflux timer and fitted with a standard thermometer for monitoring overhead temperature. Vacuum is supplied by a system composed of a pump protected by a dry ice trap and fitted with a McLeod gage for monitoring the overhead pressure. The 1 L distillation pot is heated with an electric mantel at 65 volts, agitated magnetically and fitted with a mercury manometer for monitoring bottoms pressure, and a thermocouple for monitoring bottoms temperature.

The still pot is charged with 265 g each of m- and p-xylene and fitted with a rubber septum for sampling by syringe. The xylene mixture is heated at total reflux and atmosphere pressure with the temperature 135 C. at the head and 139 C. in the bottoms. Samples are withdrawn for analysis by collecting a few drops of distillate and extracting about 1 mL from the pot. The still is sampled after 3 hours and again after 18 hours for calibration by GC and theoretical plate calculations using the Fenske correlation and a relative volatility, $\alpha=1.0209$.

Charge the mixture of 2-(4-cyclopropanecarbonyl-phenyl)-2-methyl-propionic acid, ethyl ester and 2-(3-cyclopropanecarbonyl-phenyl)-2-methyl-propionic acid, ethyl ester (901.2 g) to the still pot and heat at total reflux until the column has equilibrated. Take a forecut at 2:1 reflux ratio and increase the reflux ratio to 5:1 and the 2-(3-cyclopropanecarbonyl-phenyl)-2-methyl-propionic acid, ethyl ester stripped. Cool and release vacuum and allow to sit overnight. Add bis(2-ethylhexyl)phthalate (dioctyl phthalate) (100 mL) to the still pot and restart the still as before. Once the still has equilibrated, collect mixed fractions of 2-(4-cyclopropanecarbonyl-phenyl)-2-methyl-propionic acid, ethyl ester and 2-(3-cyclopropanecarbonyl-phenyl)-2-methyl-propionic acid, ethyl ester at 10:1 reflux ratio. Once the overheads are free of 2-(3-cyclopropanecarbonyl-phenyl)-2-methyl-propionic acid, ethyl ester by GC analysis, reduce the reflux ratio to 2:1 and collect the title compound.

Method B: Place crude mixture of 2-(4-cyclopropanecarbonyl-phenyl)-2-methyl-propionic acid, ethyl ester and 2-(3-cyclopropanecarbonyl-phenyl)-2-methyl-propionic acid, ethyl ester (4872 g) on a rotary evaporator and strip of vaolatives to an end point of 85 C., 15 mm to give a brown oil (4006 g). Charge a 3 L round bottom three neck flask equipped with magnetic stirbar, thermometer and distillation head with stripped crude mixture of 2-(4-cyclopropanecarbonyl-phenyl)-2-methyl-propionic acid, ethyl ester and 2-(3-cyclopropanecarbonyl-phenyl)-2-methyl-propionic acid, ethyl ester. Distill the oil at 0.5 mm Hg and discard a light fraction boiling at 25–130 C. (pot temp –105–165 C., 9.5 g). Continue distilling the oil at 0.5 mm Hg and collect a second fraction boiling at 130–150 C. (pot temperature 165–190, 3217 g).

Place the crude flash distilled product (1000 g) in a 4 L Hastelloy reactor equipped with Camille control along with water (500 mL) and ethanol 2B (2 L). Heat the mixture to 40 C. while agitating at 400 rpm. Set the reactor jacket to cool the contents at approximately 12 C./hour to a final temperature of 0 C. after a clear solution is observed. Then set the jacket to cool the reactor contents at approximately 12 C./hour to a final temperature of –15 C. and hold at that temperature for more than one hour. Filter the slurry, wash with cold (–15 C.) ethanol, cold heptanes (–15 C.) and dry to give a solid (507 g). Purify by recrystallization from mixed heptanes as above to give the title compound (503 g) after drying.

Recycle: Pack a 31/32 in. I.D. vacuum jacked and silvered column with 53 inches of 1 in. diameter, 316 stainless steel packing. For high temperature distillation, the column is fitted with an adiabatic jacket composed of an inner layer of 1 in. fiber glass wrapped with heat tape in an upper and lower zone and finally covered with 2 in. fiber glass insulation. The upper zone is heated at 135 C. and the lower zone at 185 C. The magnetic reflux splitting head is controlled by a reflux timer and fitted with a standard thermometer for monitoring overhead temperature. Vacuum is supplied by a system composed of a pump protected by a dry ice trap and fitted with a McLeod gage for monitoring the overhead pressure. The 1 L distillation pot is heated with an electric mantel at 65 volts, agitated magnetically and fitted with a mercury manometer for monitoring bottoms pressure, and a thermocouple for monitoring bottoms temperature.

The still pot is charged with 265 g each of m- and p-xylene and fitted with a rubber septum for sampling by syringe. The xylene mixture is heated at total reflux and atmosphere pressure with the temperature 135 C. at the head and 139 C. in the bottoms. Samples are withdrawn for analysis by collecting a few drops of distillate and extracting about 1 mL from the pot. The still is sampled after 3 hours and again after 18 hours for calibration by GC and theoretical plate calculations using the Fenske correlation and a relative volatility, $\alpha=1.0209$.

Charge the still pot with the mother liquors from the crystllization of the mixture of 2-(4-cyclopropanecarbonyl-phenyl)-2-methyl-propionic acid, ethyl ester and 2-(3-cyclopropanecarbonyl-phenyl)-2-methyl-propionic acid, ethyl ester (759 g, 14.7 wt % p-isomer). Distill as described above to give 510 g overhead at a 5:1 reflux ratio (0.2 mm bottom pressure, 7–13 mm overhead pressure, 182–205 C. bottom termperature, 92–144 C. overhead temperature). Save the bottoms (214 g, 52 wt % p-isomer) for recycle.

Charge a 250 ml round bottom flask equipped with a distillation head, thermometer, and magnetic stirbar with 190 g of the saved bottoms from above. Flash distill, retaining the fraction boiling at 149–165 C. (0.6 mm, pot temperature=159–190 C.) to give 178 g (50.5% p-isomer).

Mix flash distilled material (981 g) with material obtained from the recycle flash distillation (108 g) to give 1100 g of recycle material for crystallization. Crystallize 92.5 g (94 wt % p-isomer) from 25% water-ethanol to give the title compound (39.7 g) after drying.

EXAMPLE 18

Step h and step 1: 2-(4-Cyclopropanecarbonyl-phenyl)-2-methyl-propionic Acid, Ethyl Ester and 2-(3-Cyclopropanecarbonyl-phenyl)-2-methyl-propionic Acid, Ethyl Ester Method A: Place aluminum chloride (586 g, 4.4 moles) and methylene chloride (300 mL) in a 2 L 3-neck round bottom flask equipped with an overhead stirrer, dry ice condenser, and nitrogen atmosphere. Cool to 10 C. and add, by dropwise addition, chlorobutyryl chloride (338 g, 2.4 moles), keeping the temperature below 15 C. After addition is complete, add, by dropwise addition, ethyl 2-methyl-2-phenylpropionate (384 g, 2 mol), keeping the temperature below 15 C. After addition was complete, warm the reaction mixture to 22 C. and stir for 1 hour. Raise the temperature to 90 C., stir for 90 minutes, cool to room temperature and slowly pounr into a 6 L stirred flask containing ice/water (4 kg). Filter through a celite precoat, separate the organic phase and wash the aqueous phase with methylene chloride (50 mL). Evaporate the solvent in vacuo to give a mixture of 2-[4-(4-chloro-butyryl)-phenyl]-2-methyl-proprionic acid, ethyl ester and 2-[3-(4-chloro-butyryl)-phenyl]-2-methyl-proprionic acid, ethyl ester.

Dissolve the mixture of 2-[4-(4-chloro-butyryl)-phenyl]-2-methyl-proprionic acid, ethyl ester and 2-[3-(4-chloro-butyryl)-phenyl]-2-methyl-proprionic acid, ethyl ester in 2B ethanol (400 mL) and place in a 3 L 3-neck round bottom flask equipped with an overhead stirrer, gas inlet and reflux condenser. Add anhydrous HCl (50 g) and sitr the mixture at 70 C. for 1 hour. Cool the solution to 15 C. and add, by dropwise addition, aqueous 50% NaOH (260 g), keeping the temperature below 15 C. After the addition, stir the mixture an addition 1 hour at 22 C. Add toluene (700 mL) followed by acetic acid (2 g) and then water (500 mL). Separate the layers and evaporate the solvent in vacuo to give the title compuond as a yellow oil (551 g).

Method B: Place aluminum chloride (458 g, 3.4 mole) and methylene chloride (234 mL) in a 2 L 3 nck round bottom flask equipped with an overhead stirrer, dry ice condenser and nitrogen atmosphere. Cool to 10 C. and add, by dropwise addition, 4-chlorobutyryl chloride (264 g, 1.9 mol), keeping the temperature below 15 C. After addition is complete, add, by dropwise addition, ethyl 2-methyl-2-phenylpropionate (300 g, 1.56 mol), keeping the temperature below 15 C. After the addition is complete, warm the reaction mixture to 24 C. and stir for 1 hour. Raise the temperature to 57 C. for 2 hours, cool to room temperature and slowly pour into a 6 L stirred flask containing ice/water (3.1 kg). Filter through a celite precoat and separate the phases. Evaporate the solvent in vacuo to give an oil.

Dissolve the oil in 2B ethanol (312 mL) and place in a 3 L 3 neck round bottom flask equiped with an overhead stirrer, gas inlet and reflux condenser. Add anhydrous HCl (39 g) and stir the mixture at 70 C. for 1 hour. Cool to 50 C. and add, by dropwise addition, aqueous 20% NaOH (641 g), keeping the temperature below 50 C. After the addition, stir the mixture for an additional 1 hour at 50 C., cool to room temperature and neutralize with acetic acid (6.25 g). Separate the layers and evaporate the solvent in vacuo to give the title compound (391 g).

EXAMPLE 19

Step h and step 1: 2-(4-Cyclopropanecarbonyl-phenyl)-2-methyl-propionic Acid, 2-ethylhexyl Ester Mix methylene chloride (50 mL), 2-ethylhexyl alcohol (130 g, 1 mol) and triethylamine (50 g, 0.5 mol). Add, by dropwise addition, ethyl dimethylphenylacetyl chloride (91 g, 0.5 mol). Heat the reaction mixture to 68 C. for 1 hour, add methylene chloride (100 mL) and stir overnight. Remove the solids by filtration, wash with methylene chloride (50 mL), combine with the liquid organics, wash with aqueous 5% HCl, (50 mL), water (50 mL) and dry over MgSO4. Evaporate the solvent in vacuo and purify by distillation (119 C. at 1mmHg) (105 g, 76%).

Place aluminum chloride (29.3 g) and methylene chloride (30 mL) in a 250 mL round bottom flask with an overhead stirrer, temperature control, condenser, additonal funnel and nitrogen atmosphere. Add, by dropwise addition, chlorobutyryl chloride (16.9 g), keeping the temperature below 10 C. After addition is complete, warm the reaction mixture to 36 C. and hold for 24 hours. Quench the reaction mixture into ice/water (200 g) and extract with methylene chloride (50 mL). Wash the organics with water (50 mL) and dry (MgSO4). Evaporate the solvent in vacuo to give an oil (30 g). Place the oil in a 250 mL flask equipped with an overhead stirrer, gas inlet, condenser and thermometer. Add 2B ethanol (150 mL) followed by anhydrous HCl (5 g). Heat the reaction mixture to 76 C. for 2.5 hours then add additional HCl (5 g). Heat the reaction mixture at 76 C. for 22 hours, evaporate the solvent in vacuo to give an oil. Dissolve the oil in 2B ethanol (100 mL), treat with solid KOH (10 g) and heat at reflux for 2 hours.

EXAMPLE 20

Step m and step 1: 2-(4-Cyclopropanecarbonyl-phenyl)-2-methyl-propionic Acid, Ethyl Ester Dissolve 2-[4-(4-chloro-butyryl)-phenyl]-acetic acid, ethyl ester (28.5 g) in toluene (50 mL) and evaporate the solvent in vacuo to remove traces of ethanol. Dissolve the residue in diglyme (50 mL) and add, by dropwise addition, to a suspension of sodium hydride (12.2 g of a 60% suspension in mineral oil) slurried in diglyme (150 mL) containing methyl chloride (10 g). Slowly add methyl chloride (10 g) and stir for 15 minutes. Filter through filter aid, wash filtercake with acetonitrile and evaporate the solvent. Remove meta-isomer by distillation (150° C. @ 1 mm) and crystallize (ethanol) to give the title compound (93%).

EXAMPLE 21

Step f and step: 2-(4-Cyclopropanecarbonyl-phenyl)-propionic Acid, Ethyl Ester and 2-(3-Cyclopropanecarbonyl-phenyl)-propionic Acid, Ethyl Ester Dissolve 2-phenylpropionic acid (30 g) in 2B ethanol (100 mL and add anhydrous HCl (10 g). Allow to sit for 48–72 hours, evaporate the solvent in vacuo and purify by distillation to give ethyl 2-phenylpropionate (31 g); bp 100 C. at 6 mmm.

Place aluminum chloride (49.4 g, 0.371 mole) and methylene chloride (50 mL) in a 250 mL 3-neck round bottom flask equipped with an overhead stirrer, addition funnel and thermometer. Cool to less then 10 C. and add, by dropwise addition, chlorobutyrylchloride (23.8 g, 0.202 mol), keeping the temperature below 10 C. After addition is complete, add, by dropwise addition, ethyl 2-phenylpropianate (30 g, 0.17 mol), keeping the temperature below 10 C. Stir at room temperature for 1 hour then heat at reflux for 14 hours. Quench into ice/water (350 g) and filter through a celite pre-coat. Separate the layers and evaporate the solvent in vacuo to give a red oil.

Dissolve the red oil in 2B ethanol (35 mL) and place in a round bottom flask with a condenser and gas inlet. Add anhydrous HCl (4.3 g) and heat the solution to 70 C. for 1 hour. Cool the solution to 10 C and add, by dropwise addition, 20% aqueous sodium hydroxide. Separate the layers and evaporate the solvent in vacuo to give an oil.

Re-treat the oil with HCl in 2B ethanol as above, cool to 10 C. and treat with a 20% solution of sodium ethoxide in ethanol. Neutralize with acetic acid, filter the solids and evaporate the solvent in vacuo. Purify by distillation to give the title compound; bp 161–167 at 1.2 mm.

The novel intermediates of formula (II), formula (III), formula (IV), formula (V), formula (VI) and formula (VII) wherein $R_5$ is $CONR_6R_7$ may also be prepared as described in Scheme G. In Scheme G, all substituents are as previously defined unless otherwise indicated.

(II), formula (III), formula (IV), formula (V), formula (VI) and formula (VII) wherein $R_5$ is $CONR_6R_7$.

In step a, the appropriate phenylacetic acid amide compound of structure (37) is methylated to give the corresponding α-methylphenylacetic acid amide compound of structure (38) as described previously in Scheme A, step a.

Appropriate phenylacetic acid amide compound of structure (37) are prepared from the corresponding phenylacetic acid by standard amide-forming reactions as are known in the art. The appropriate phenylacetic acids may be prepared

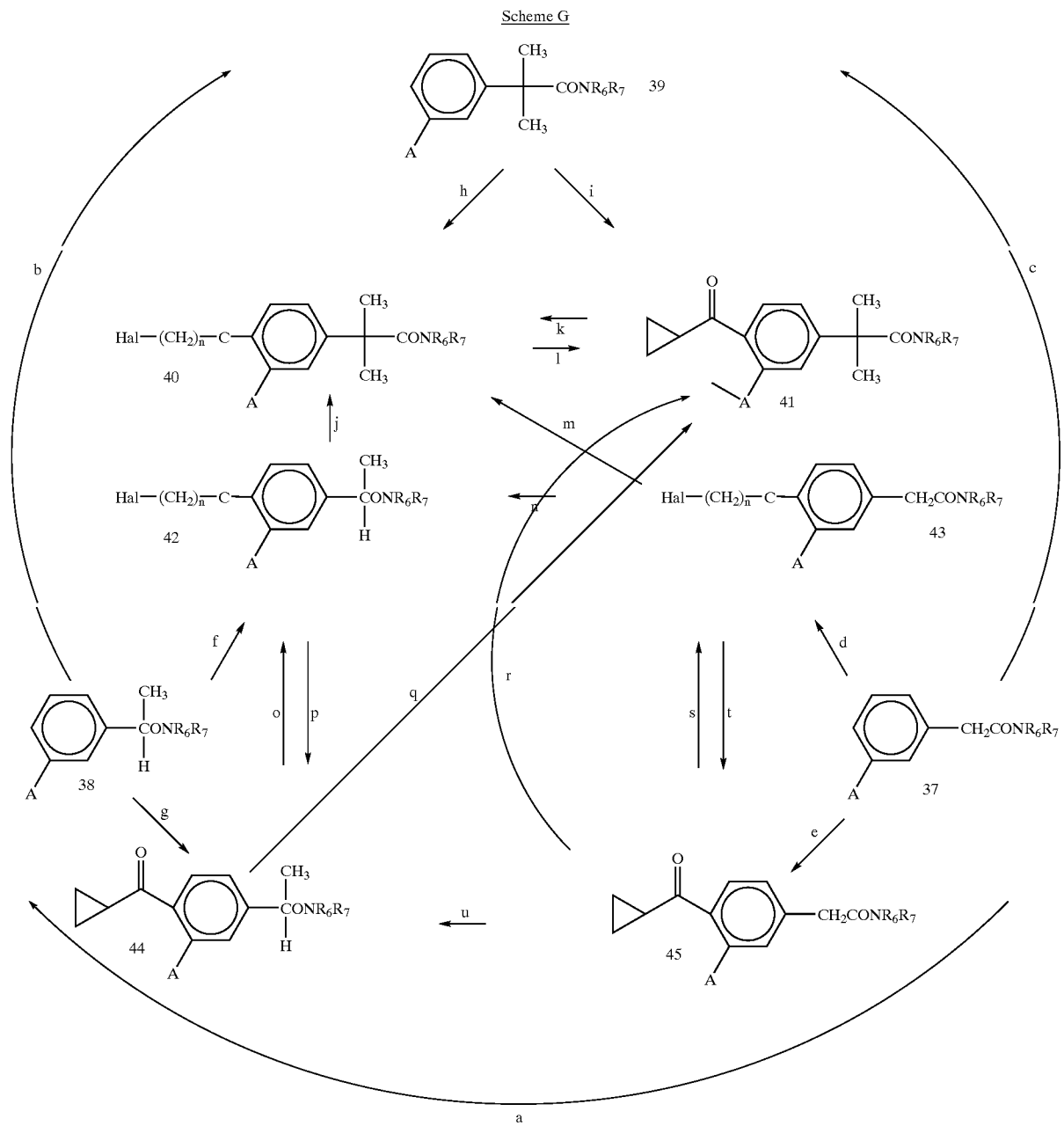

Scheme G

Scheme G provides alternative various general synthetic procedures for preparing the novel intermediates of formula by hyrdolysis of the corresponding 2-cyano-2-propylbenzene compound of structure (27) by techniques and procedures well known and appreciated by one of ordinary skill in the art.

In step b, the appropriate α-methylphenylacetic acid amide compound of structure (38) is methylated to give the corresponding α,α-dimethylphenylacetic acid amide compound of structure (39) as described previously in Scheme A, step a.

Appropriate α-methylphenylacetic acid amide compound of structure (38) are prepared from the corresponding α-methylphenylacetic acid by standard amide-forming reactions as are known in the art as as described in step a.

In step c, the appropriate phenylacetic acid amide compound of structure (37) is dimethylated to give the corresponding α,α-dimethylphenylacetic acid amide compound of structure (39) as described previously in Scheme A, step c.

In step d, the appropriate phenylacetic acid amide compound of structure (37) is acylated with an appropriate ω-halo compound of the structure Hal-(CH$_2$)$_n$—C(=O)—B, wherein B is Hal or hydroxy, Hal is Cl, Br or I and n is as previously defined to give the corresponding ω'-halo-α'-keto-phenylacetic acid amide compound of structure (43) as described previously in Scheme A, step d.

In step e, the appropriate phenylacetic acid amide compound of structure (37) is acylated with an appropriate cyclopropyl compound of the structure

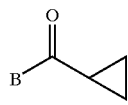

wherein B is as previously defined to give the corresponding cyclopropylketo-phenylacetic acid amide compound of structure (45) as described previously in Scheme A, step e.

In step f, the appropriate α-methylphenylacetic acid amide compound of structure (38) is acylated with an appropriate ω-halo compound of the structure Hal-(CH$_2$)$_n$—C(=O)—B, wherein B is Hal or hydroxy, Hal is Cl, Br or I and n is as previously defined to give the corresponding ω'-halo-α'-keto-α-methylphenylacetic acid amide compound of structure (42) as described previously in Scheme A, step d.

In step g, the appropriate α-methylphenylacetic acid amide compound of structure (38) is acylated with an appropriate cyclopropyl compound of the structure

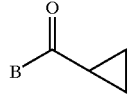

wherein B is as previously defined to give the corresponding cyclopropylketo-α-methylphenylacetic acid amide compound of structure (44) as described previously in Scheme A, step e.

In step h, the appropriate α,α-dimethylphenylacetic acid amide compound of structure (39) is acylated with an appropriate ω-halo compound of the structure Hal-(CH$_2$)$_n$—C(=O)—B, wherein B is Hal or hydroxy, Hal is Cl, Br or I and n is as previously defined to give the corresponding ω'-halo-α'-keto-α,α-di-methylphenylacetic acid amide compound of structure (40) as described previously in Scheme A, step d.

Appropriate α,α-dimethylphenylacetic acid amide compound of structure (39) are prepared from the corresponding α,α-dimethylphenylacetic acid by standard amide-forming reactions as are known in the art as as described in step a.

In step i, the appropriate α,α-dimethylphenylacetic acid amide compound of structure (39) is acylated with an appropriate cyclopropyl compound of the structure

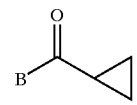

wherein B is as previously defined to give the corresponding cyclopropylketo-α,α-dimethylphenylacetic acid amide compound of structure (41) as described previously in Scheme A, step e.

In step j, the appropriate ω'-halo-α'-keto-α-methylphenylacetic acid amide compound of structure (42) is methylated to give the corresponding ω'-halo-α'-keto-α,α-di-methylphenylacetic acid amide compound of structure (40) as described previously in Scheme a, step a.

In step k, the cyclopropyl functionality of the appropriate cyclopropylketo-α,α-dimethylphenylacetic acid amide compound of structure (41) is ring-opened to give the corresponding ω'-halo-α'-keto-α,α-di-methylphenylacetic acid amide compound of structure (40) wherein n=3 as described previously in Scheme A, step j.

In step 1, the appropriate ω'-halo-α'-keto-α,α-di-methylphenylacetic acid amide compound of structure (40) wherein n=3 is ring-closed to give the corresponding cyclopropylketo-α,α-dimethylphenylacetic acid amide compound of structure (41) as described previously in Scheme A, step k.

In step m, the appropriate ω'-halo-α'-keto-phenylacetic acid amide compound of structure (43) is dimethylated to give the corresponding ω'-halo-α'-keto-α,α-di-methylphenylacetic acid amide compound of structure (40) as described previously in Scheme A, step c.

In step n, the appropriate ω'-halo-α'-keto-phenylacetic acid amide compound of structure (43) is methylated to give the corresponding ω'-halo-α'-keto-α-methylphenylacetic acid amide compound of structure (42) as described previously in Scheme A, step a.

In step o, the cyclopropyl functionality of the appropriate cyclopropylketo-α-,methylphenylacetic acid amide compound of structure (44) is ring-opened to give the corresponding ω'-halo-α'-keto-α-methylphenylacetic acid amide compound of structure (42) wherein n=3 as described previously in Scheme A, step j.

In step p, the appropriate ω'-halo-α'-keto-α-methylphenylacetic acid amide compound of structure (42) wherein n=3 is ring-closed to give the corresponding cyclopropylketo-α-methylphenylacetic acid amide compound of structure (44) as described previously in Scheme A, step k.

In step q, the appropriate cyclopropylketo-α-methylphenylacetic acid amide compound of structure (44) is methylated to give the corresponding cyclopropylketo-α,α-dimethylphenylacetic acid amide compound of structure (41) as described previously in Scheme A, step a.

In step r, the appropriate cyclopropylketo-phenylacetic acid amide compound of structure (45) is dimethylated to give the corresponding cyclopropylketo-α,α-dimethylphenylacetic acid amide compound of structure (41) as described previously in Scheme A, step c.

In step s, the cyclopropyl functionality of the appropriate cyclopropylketo-phenylacetic acid amide compound of structure (45) is ring-opened to give the corresponding ω'-halo-α'-keto-phenylacetic acid amide compound of structure (43) wherein n=3 as described previously in Scheme A, step j.

In step t, the appropriate ω'-halo-α'-keto-phenylacetic acid amide compound of structure (43) wherein n=3 is ring-closed to give the corresponding cyclopropylketo-phenylacetic acid amide compound of structure (45) as described previously in Scheme A, step k.

In step u, the appropriate cyclopropylketo-phenylacetic acid amide compound of structure (45) is methylated to give the corresponding cyclopropylketo-α-methylphenylacetic acid amide compound of structure (44) as described previously in Scheme A, step a.

Starting materials for use in Scheme G are readily available to one of ordinary skill in the art.

The following example present typical syntheses as described in Scheme G. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "µL" refers to microliters; "µg" refers to micrograms; and "µM" refers to micromolar.

EXAMPLE 22

Step h: 2-[4-(4-Chloro-butyryl)-phenyl]-2-methyl-propionic Acid, N-methoxy-N-methylamide Dissolve 2-methyl-2-phenyl-propionic acid (15.0 g, 91.2 mmol) in toluene (80 mL) and add, by dropwise addition over 5 minutes, thionyl chloride (15 mL, 206 mmol). Stir at room temperature overnight, add additional thionyl chloride (3 mL, 41.1 mmol) and heat to reflux for 1 hour. Remove excess thionyl chloride by azeotropic distillation with toluene (40 mL). Add toluene (20 mL) to the reaction mixture along with a solution of potassium carbonate (28.0 g, 203 mmol) in water (40 mL). Add, by dropwise addition, a solution of N,O-dimethylhydroxylamine hydrochloride (8.9 g, 91.2 mmol) in water (20 mL) without cooling and stir for 2 hours. Add tert-butylmethyl ether (75 mL) following by slow addition of aqueous HCl (2N, 75 mL) with vigorous stirring. Separate the organic layer and wash with aqueous HCl (2N, 75 mL), saturated sodium hydrogen carbonate (25 mL) and brine (50 mL). Dry the organic layer over ($Na_2SO_4$), filter, evaporate the filtrate in vacuo and purify by vacuum distillation to give 2-methyl-2-phenyl-propionic acid, N-methoxy-N-methylamide (18.0 g, 95%); bp 91–103° C./5 mm Hg.

MS (CI, $CH_4$) m/e 208 ($M^++1$, 100), 119.

Slurry $AlCl_3$ (10.15 g, 76.1 mmol) and methylene chloride (45 mL) under a nitrogen atmosphere at room temperature. Add 4-chlorobutyryl chloride (4.27 mL, 38.1 mmol), stir for 20 minutes and add, by dropwise addition over 10 minutes, a solution of 2-methyl-2-phenyl-propionic acid, N-methoxy-N-methylamide (6.58 g, 31.7 mmol) in methylene chloride (15 mL). Stir at room temperature for 45 minutes, then heat at 30–35° C. for 7 hours. Pour into ice water (150 mL) and separate the layers. Wash the aqueous layer with water (3×75 mL), combine the aqueous layers and extract with methylene chloride (2×75 mL). Combine the organic layers and dry ($Na_2SO_4$). Filter, evaporate the filtrate in vacuo and purify by silica gel chromatography (3:1 hexane/ethyl acetate) give the title compound (6.19 g, 63%) as a light yellow oil.

MS (CI,$CH_4$) m/e 312 ($M^++1$), 276.

EXAMPLE 23

Step h: 2-[4-(4-Chloro-butyryl)-phenyl]-2-methyl-propionic Acid, Dimethylamide

Dissolve 2-methyl-2-phenyl-propionic acid (15.0 g, 91.2 mmol) in toluene (80 mL) and add, by dropwise addition over 5 minutes, thionyl chloride (15 mL, 206 mmol). Stir at room temperature overnight, add additional thionyl chloride (3 mL, 41.1 mmol) and heat to reflux for 1 hour. Remove excess thionyl chloride by azeotropic distillation with toluene (40 mL). Add toluene (20 mL) to the reaction mixture along with a solution of potassium carbonate (28.0 g, 203 mmol) in water (40 mL). Add, by dropwise addition, a 40% aqueous solution of dimethylamine hydrochloride (20 mL, 0.18 mol) without cooling and stir for 2 hours. Add tert-butylmethyl ether (75 mL) following by slow addition of aqueous HCl (2N, 75 mL) with vigorous stirring. Separate the organic layer and wash with aqueous HCl (2N, 75 mL), saturated sodium hydrogen carbonate (25 mL) and brine (50 mL). Dry the organic layer over ($Na_2SO_4$), filter, evaporate the filtrate in vacuo and purify by crystallization to give 2-methyl-2-phenyl-propionic acid, dimethylamide (15.35 g, 88%) as a white solid; mp 57–59° C.

Anal. Calcd for $C_{12}H_{17}NO$: C, 75.35; H, 8.96; N, 7.32; Found: C, 75.12; H, 8.86; N, 7.26.

Add $AlCl_3$ (1.12 g, 8.40 mmol) to carbon tetrachloride (6 mL) under a nitrogen atmosphere at room temperature. Add 4-chlorobutyryl chloride (0.49 mL, 4.37 mmol), stir for 15 minutes and add, by dropwise addition over 3 minutes, a solution of 2-methyl-2-phenyl-propionic acid, dimethylamide (0.64 g, 3.36 mmol) in carbon tetrachloride (6 mL). Stir at room temperature for 17 hours, dilute with methylene chloride (10 mL), pour into ice water (50 mL) and separate the layers. Wash the aqueous layer with methylene chloride (2×70 mL), 5% aqueous sodium hydrogen carbonate, combine the organic layers and dry ($Na_2SO_4$). Filter, evaporate the filtrate in vacuo and purify by silica gel chromatography (5:2 hexane/ethyl acetate) to give the title compound (0.72 g, 72%) as a light yellow oil.

EXAMPLE 24

Step h: 2-[4-(4-Chloro-butyryl)-phenyl]-2-methyl-propionic Acid, Pyrrolidineamide Dissolve 2-methyl-2-phenyl-propionic acid (15.0 g, 91.2 mmol) in toluene (80 mL) and add, by dropwise addition over 5 minutes, thionyl chloride (15 mL, 206 mmol). Stir at room temperature overnight, add additional thionyl chloride (3 mL, 41.1 mmol) and heat to reflux for 1 hour. Remove excess thionyl chloride by azeotropic distillation with toluene (40 mL). Add tolune (20 mL) to the reaction mixture along with a solution of potassium carbonate (28.0 g, 203 mmol) in water (40 mL). Add, by dropwise addition, pyrrolidine (7.61 mL, 91 mmol) without cooling and stir for 2 hours. Add tert-butylmethyl ether (75 mL) following by slow addition of aqueous HCl (2N, 75 mL) with vigorous stirring. Separate the organic layer and wash with aqueous HCl (2N, 75 mL), saturated sodium hydrogen carbonate (25 mL) and brine (50 mL). Dry the organic layer over ($Na_2SO_4$), filter, evaporate the filtrate in vacuo and purify by crystallization to give 2-methyl-2-phenyl-propionic acid, pyrrolidineamide (18.28 g, 92%) as a solid; mp 96–97° C.

Anal. Calcd for $C_{14}H_{19}NO$: C, 77.38; H, 8.81; N, 6.45; Found: C, 77.21; H, 8.70; N, 6.41.

Add $AlCl_3$ (8.31 g, 62.3 mmol) to carbon tetrachloride (65 mL) under a nitrogen atmosphere at room temperature. Add 4-chlorobutyryl chloride (03.5 mL, 31.2 mmol), stir for 15 minutes and add, by dropwise addition over 15 minutes, a solution of 2-methyl-2-phenyl-propionic acid, pyrrolidineamide (5.64 g, 26.0 mmol) in carbon tetrachloride (60 mL). Stir at room temperature for 17 hours, pour into ice water (100 mL) and separate the layers. Wash the aqueous layer with methylene chloride (2×70 mL), 5% aqueous sodium hydrogen carbonate, combine the organic layers and dry ($Na_2SO_4$). Filter, evaporate the filtrate in vacuo and purify by silica gel chromatography (5:2 hexane/ethyl acetate) to give the title compound (6.55 g, 78%) as a light yellow oil.

EXAMPLE 25

Step 1: 2-(4-Cyclopropanecarbonyl-phenyl)-2-methyl-propionic Acid, N-methoxy-N-methylamide Add potassium hydroxide (13 g) to 2-[4-(4-chloro-butyryl-phenyl]-2-methyl-propionamide, N-methoxy-N-methylamide (96.6 mmol) and stir at room temperature for 40 minutes, filter and wash the filtercake with ethanol. Evaporate the ethanol in vacuo, dissolve in methylene chloride (100 mL), wash with water (50 mL), 5% sodium hydrogen carbonate (50 mL) and water (50 mL). Evaporate the solvent in vacuo, removing water with toluene azeotrope. Purify the product by distillation followed by recrystallization (heptane) to give the title compound (7.4 g).

The following compounds can be prepared by procedures depicted in Scheme G:

(4-cyclopropanecarbonyl-phenyl)-acetic acid, N-methoxy-N-methylamide;
(4-cyclopropanecarbonyl-phenyl)-acetic acid, dimethylamide;
(4-cyclopropanecarbonyl-phenyl)-acetic acid, pyrrolidineamide;
2-(4-Cyclopropanecarbonyl-phenyl)-proprionic acid, N-methoxy-N-methylamide;
2-(4-Cyclopropanecarbonyl-phenyl)-proprionic acid, dimethylamide;
2-(4-Cyclopropanecarbonyl-phenyl)-proprionic acid, pyrrolidineamide;
2-(4-Cyclopropanecarbonyl-phenyl)-2-methyl-proprionic acid, N-methoxy-N-methylamide;
2-(4-Cyclopropanecarbonyl-phenyl)-2-methyl-proprionic acid, dimethylamide;
2-(4-Cyclopropanecarbonyl-phenyl)-2-methyl-proprionic acid, pyrrolidineamide;
[4-(4-Chloro-butyryl)-phenyl]-acetic acid, N-methoxy-N-methylamide;
[4-(4-Chloro-butyryl)-phenyl]-acetic acid, dimethylamide;
[4-(4-Chloro-butyryl)-phenyl]-acetic acid, pyrroldineamide;
2-[4-(4-Chloro-butyryl)-phenyl]-propionic acid, N-methoxy-N-methylamide;
2-[4-(4-Chloro-butyryl)-phenyl]-propionic acid, dimethylamide;
2-[4-(4-Chloro-butyryl)-phenyl]-propionic acid, pyrroldineamide;
2-[4-(4-Chloro-butyryl)-phenyl]-2-methyl-propionic acid, N-methoxy-N-methylamide;
2-[4-(4-Chloro-butyryl)-phenyl]-2-methyl-propionic acid, dimethylamide;
2-[4-(4-Chloro-butyryl)-phenyl]-2-methyl-propionic acid, pyrroldineamide;

The novel intermediates of formula (II), formula (III), formula (IV), formula (V), formula (VI) and formula (VII) wherein $R_5$ is COOH, COOalkyl or $CONR_6R_7$ may be prepared as described in Scheme H. In Scheme H, all substituents are as previously defined unless otherwise indicated.

Scheme H
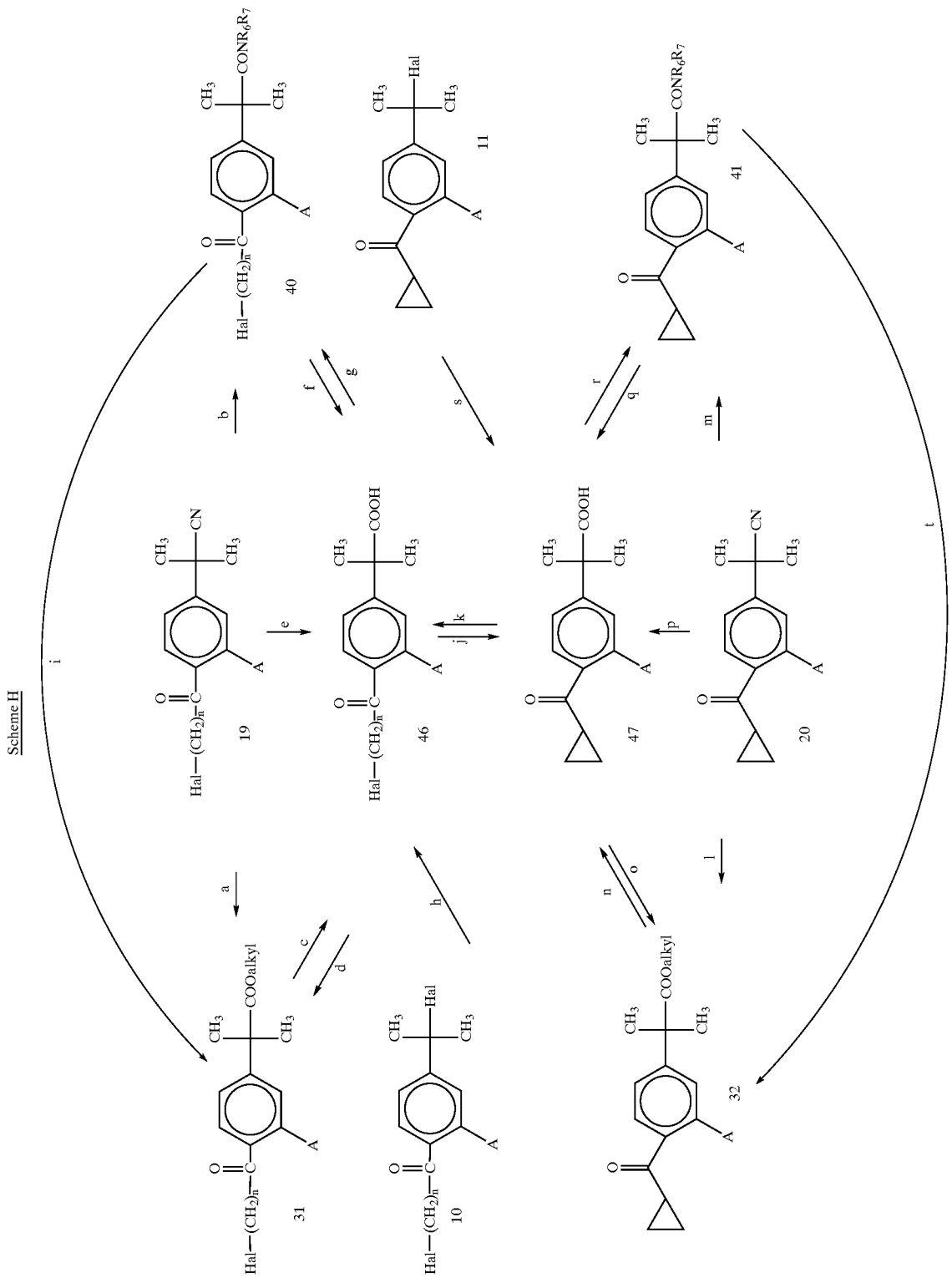

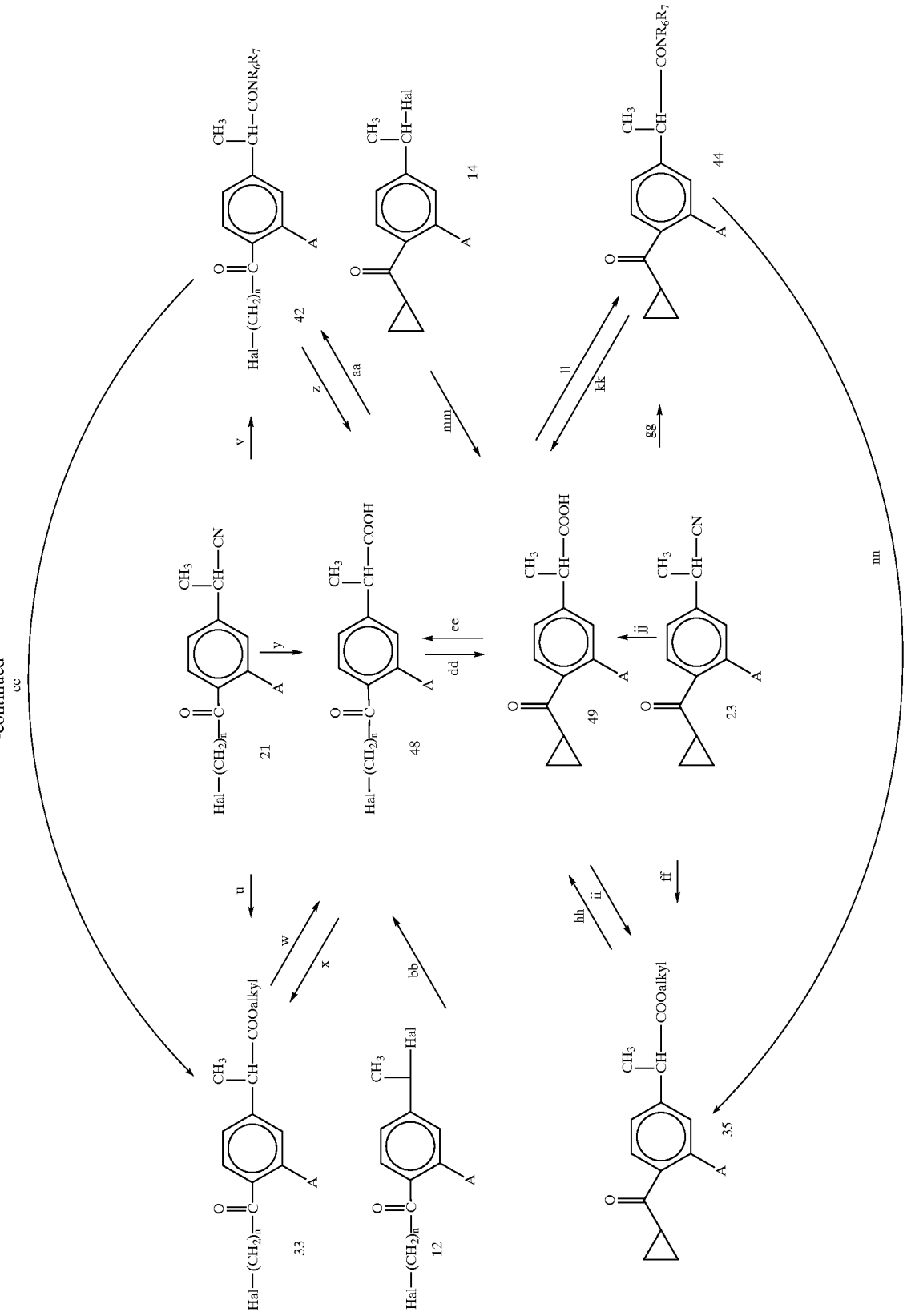

-continued
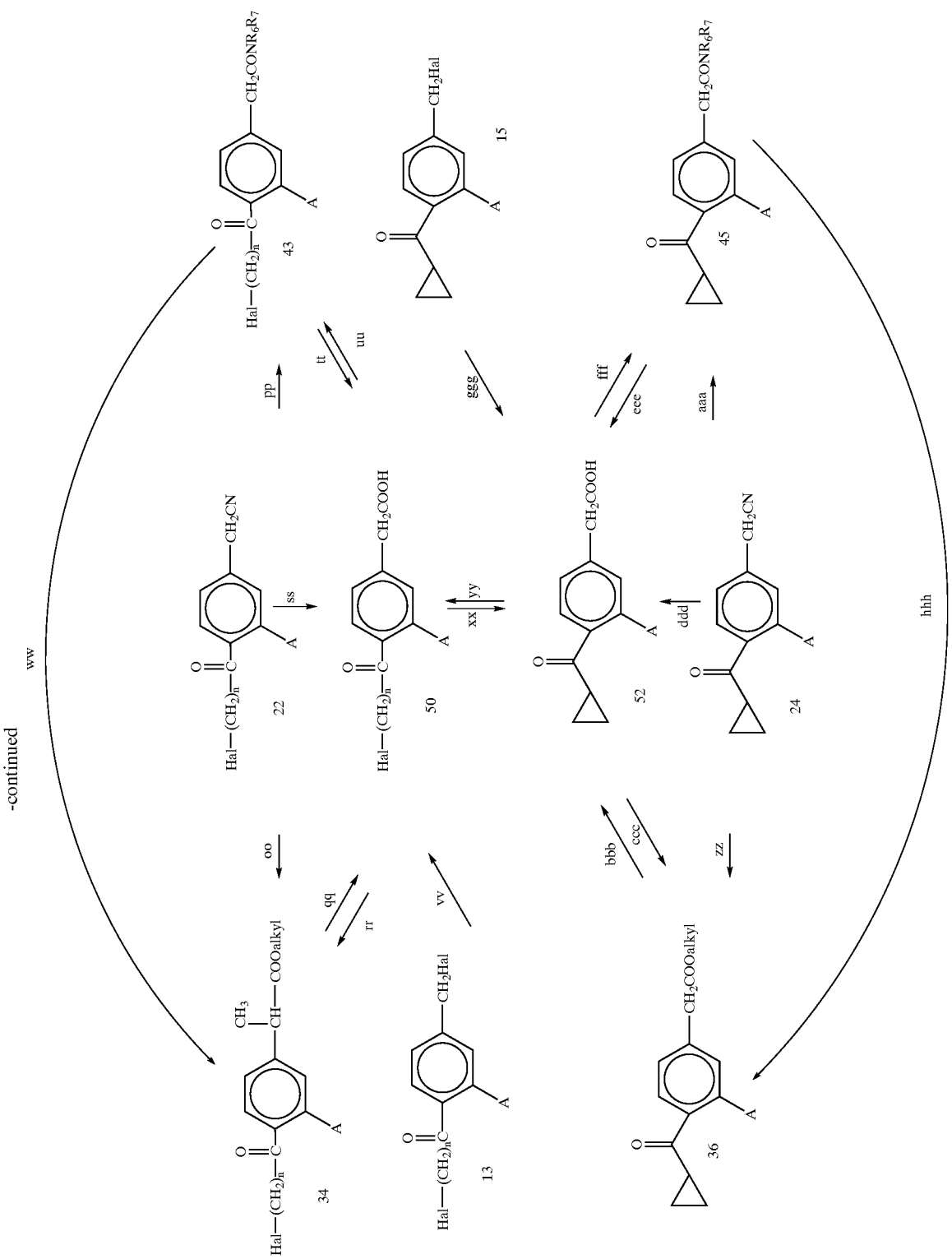

Scheme H provides various general synthetic procedures for preparing the novel intermediates of formula (II), formula (III), formula (IV), formula (V), formula (VI) and formula (VII) wherein $R_5$ is COOH, COOalkyl or $CONR_6R_7$.

In step a, the nitrile functionality of the appropriate ω-halo-cyanocumylketone compound of structure (19) is converted to the corresponding ester by reaction with an appropriate $C_1$ to $C_6$ alcohol to give the corresponding ω'-halo-α'-keto-α,α-dimethylphenylacetic acid ester compound of structure (31).

For example, the ω'-halo-α'-keto-α,α-dimethylphenylacetic acid ester compound of structure (31) may be prepared by reacting an appropriate ω-halo-cyanocumylketone compound of structure (19) with an appropriate $C_1$–$C_6$ alcohol in the presence of a suitable anhydrous acid followed by treatment with water. Examples of appropriate alcohols are methanol, ethanol, propanol, and the like, with methanol being preferred. Examples of appropriate acids are hydrogen chloride and hydrogen bromide, with hydrogen chloride being preferred. The reaction time varies from about ½ hour to 48 hours, preferably 3 to 5 hours and the reaction temperature varies from about −20° C. to room temperature, preferably −10° C. to 0 C. The ω'-halo-α'-keto-α,α-dimethylphenylacetic acid ester compound of structure (28) is recovered from the reaction zone by evaporation of the solvent followed by extraction as is known in the art. The ω'-halo-α'-keto-α,α-dimethylphenylacetic acid ester compound of structure (31) may be purified by procedures well known in the art, such as chromatography.

In step b, the nitrile functionality of the appropriate ω-halo-cyanocumylketone compound of structure (19) is converted to the corresponding amide to give the ω'-halo-α'-keto-α,α-dimethylphenylacetic acid amide compound of structure (40) wherein $R_6$ and $R_7$ are both hydrogen.

For example, hydrolysis may be achieved by using a suitable acid, such as concentrated hydrochloric acid as is known in the art.

In step c, the carboxy ester functionality of the appropriate ω'-halo-α'-keto-α,α-dimethylphenylacetic acid ester compound of structure (31) is hydrolyzed to give the corresponding ω'-halo-α'-keto-α,α-dimethylphenylacetic acid compound of structure (46).

For example, hydrolysis may be achieved by using a suitable non-nucleophilic base, such as sodium methoxide in methanol as is known in the art. Other methods known in the art for ester cleavage include potassium carbonate in methanol, methanolic ammonia, potassium carbonate, potassium hydroxide, calcium hydroxide, sodium hydroxide, magnesium hydroxide, sodium hydroxide/pyridine in methanol, potassium cyanide in ethanol and sodium hydroxide in aqueous alcohols, with potassium hydroxide being preferred. The reaction is typically carried out in an aqueous lower alcohol solvent, such as methanol, ethanol, isopropyl alcohol, n-butanol, 2-ethoxyethanol or ethylene glycol or pyridine, at temperatures ranging from room temperature to the reflux temperature of the solvent, and the reaction time varies from about ½ hour to 100 hours.

In step d, the carboxy functionality of the appropriate ω'-halo-α'-keto-α,α-dimethylphenylacetic acid compound of structure (46) may be esterified by techniques and procedures well known and appreciated by one of ordinary skill in the art to give the corresponding ω'-halo-α'-keto-α,α-dimethylphenylacetic acid ester compound of structure (31).

For example, one such method involves reacting an appropriate ω'-halo-α'-keto-α,α-dimethylphenylacetic acid compound of structure (46) with an excess of an appropriate $C_1$–$C_6$ alcohol which is straight or branched in the presence of a small amount of mineral acid, such as hydrochloric acid or sulfuric acid, hydrochloric acid being preferred, at reflux. Another suitable method involves reacting an appropriate ω'-halo-α'-keto-α,α-dimethylphenylacetic acid compound of structure (46) with an excess of diazomethane in a suitable solvent such as ether at room temperature to give the methyl ester. In addition, the ω'-halo-α'-keto-α,α-dimethylphenylacetic acid ester compound of structure (28) may also be prepared by reacting an appropriate ω'-halo-α'-keto-α,α-di-methylphenylacetic acid compound of structure (46) with an excess of 2,2-dimethoxypropane in a suitable solvent such as methanol at 0 C. to room temperature to give the methyl ester. Another suitable method involves first reacting an appropriate ω'-halo-α'-keto-α,α-dimethylphenylacetic acid compound of structure (46) with thionyl chloride in a suitable solvent such as methylene chloride to give an intermediate acid chloride, followed by addition of a suitable $C_1$ to $C_6$ alcohol which is straight or branched. Another suitable method involves the alkylation of the carboxylate anion with an appropriate electrophile, such as dimethyl sulfate or ethyl bromide, to give the corresponding ω'-halo-α'-keto-α,α-dimethylphenylacetic acid ester compound of structure (31). Such methods are well known in the art and are described in *J. Org. Chem.*, 29, 2490–2491 (1964).

Alternatively, step k and step d may be combined and the ω'-halo-α'-keto-α,α-dimethylphenylacetic acid ester compound of structure (34) wherein n=3 may be prepared from the corresponding cyclopropylketo-α,α-dimethylphenylacetic acid compound of structure (50).

Alternatively, step p, step k and step d may be combined and the ω'-halo-α'-keto-α,α-dimethylphenylacetic acid ester compound of structure (31) wherein n=3 may be prepared from the corresponding cyclopropyl cyanocumylketone compound of structure (20).

In step e, the nitrile functionality of the appropriate ω-halo-cyanocumylketone compound of structure (19) is converted to the corresponding carboxy to give the ω'-halo-α'-keto-α,α-dimethylphenylacetic acid compound of structure (46).

For example, hydrolysis may be achieved by using a suitable acid, such as concentrated hydrochloric acid as is known in the art.

In step f, the amide functionality of the appropriate ω'-halo-α'-keto-α,α-dimethylphenylacetic acid amide compound of structure (40) is converted to the corresponding acid by acid hydrolysis as is known in the art to give the corresponding ω'-halo-α'-keto-α,α-dimethylphenylacetic acid compound of structure (46).

For example, hydrolysis may be achieved by using a suitable non-nucleophilic base, such as sodium methoxide in methanol as is known in the art. Other methods known in the art for ester cleavage include potassium carbonate in methanol, methanolic ammonia, potassium carbonate, potassium hydroxide, calcium hydroxide, sodium hydroxide, magnesium hydroxide, sodium hydroxide/pyridine in methanol, potassium cyanide in ethanol and sodium hydroxide in aqueous alcohols, with potassium hydroxide being preferred. The reaction is typically carried out in an aqueous lower alcohol solvent, such as methanol, ethanol, isopropyl alcohol, n-butanol, 2-ethoxyethanol or ethylene glycol or pyridine, at temperatures ranging from room temperature to the reflux temperature of the solvent, and the reaction time varies from about ½ hour to 100 hours.

In step g, the carboxy functionality of the appropriate ω'-halo-α'-keto-α,α-dimethylphenylacetic acid compound of structure (46) may be amidated by techniques and procedures well known and appreciated by one of ordinary skill in the art to give the corresponding ω'-halo-α'-keto-α,α-dimethylphenylacetic acid amide compound of structure (40).

In step h, the α-halo functionality of the appropriate ω-halo-halocumylketone compound of structure (10) is carboxylated to give the corresponding ω'-halo-α'-keto-α,α-dimethylphenylacetic acid compound of structure (46).

For example, a solution of the appropriate ω-halo-halocumylketone compound of structure (10) and a suitable catalyst, such as tetraethylammonium bromide, in a suitable polar aprotic organic solvent, such as acetonitrile, N,N-dimethylacetamide, 1-methyl-2-pyrrolidinone or dimethylformamide, are placed in a jacketed glass cell and fitted with an expanded silver mesh cathode, magnesium anode and carbon dioxide delivery tube. Rotation of the electrodes provides stirring, while electrical contact with the electrodes is made via spring loaded sliding carbon brushes placed against the concentric metal shafts (insulated from each other with a length of plastic tubing) onto which the electrodes are mounted. Carbon dioxide is introduced into the cell at pressures of 1–10 atm, for a period of time ranging from 30 minutes to 50 hours and at a temperature range of from -30° C. to 50° C. The corresponding ω'-halo-α'-keto-α,α-dimethylphenylacetic acid compound of structure (46) is isolated, after acidification with a suitable mineral acid, such as hydrochloric acid, by extractive methods as are known in the art.

It is preferred that the ω-halo functionality of the appropriate ω-halo-halocumylketone compound of structure (10) for use in step h be a ω-chloro.

Alternatively, the treatment of appropriate ω-halo-halocumylketone compound of structure (10) with a transition metal catalyst such as palladium, nickel or cobalt, optionally in the presence of a phosphine catalysis using low to modest pressures of carbon monoxide as described by Stahly et al. in U.S. Pat. No. 4,990,658, 1991 also provides the corresponding ω-halo-α'-keto-α,α-dimethylphenylacetic acid compound of structure (46).

In step i, the appropriate the amide functionality of the appropriate ω'-halo-α'-keto-α,α-di-methylphenylacetic acid amide compound of structure (40) is converted to the corresponding ester to give the ω'-halo-α'-keto-α,α-dimethylphenylacetic acid ester compound of structure (31).

For example, the appropriate ω'-halo-α'-keto-α,α-di-methylphenylacetic acid amide compound of structure (40) is reacted with an appropriate hydrogen halide in an appropriate organic solvent such as ethanol. The reaction is typically conducted at a temperature range of from room temperature to reflux and for a period of time ranging from 5 minutes to 1 hour. The ω'-halo-α'-keto-α,α-dimethylphenylacetic acid ester compound of structure (31) is recovered from the reaction zone by extractive methods as is known in the art.

In step j, the appropriate ω'-halo-α'-keto-α,α-dimethylphenylacetic acid compound of structure (46) wherein n=3 is ring-closed to give the corresponding cyclopropylketo-α,α-dimethylphenylacetic acid compound of structure (47) as described previously in Scheme A, step k.

In step k, the appropriate cyclopropylketo-α,α-dimethylphenylacetic acid compound of structure (47) is ring-opened to give the corresponding ω'-halo-α'-keto-α,α-dimethylphenylacetic acid compound of structure (46) wherein n=3 as described previously in Scheme A, step j.

In step l, the nitrile functionality of the appropriate cyclopropyl cyanocumylketone compound of structure (20) is converted to the corresponding ester by reaction with an appropriate $C_1$ to $C_6$ alcohol to give the cyclopropylketo-α,α-dimethylphenylacetic acid ester compound of structure (32) as described previously in step a.

In step m, the nitrile functionality of the appropriate cyclopropyl cyanocumylketone compound of structure (20) is converted to the corresponding amide to give the ω'-halo-α'-keto-α,α-di-methylphenylacetic acid amide compound of structure (41) wherein $R_6$ and $R_7$ are both hydrogen as described previously in step b.

In step n, the carboxy ester functionality of the appropriate cyclopropylketo-α,α-dimethylphenylacetic acid ester compound of structure (32) is hydrolyzed to give the corresponding cyclopropylketo-α,α-dimethylphenylacetic acid compound of structure (47) as described previously in step c.

In step o, the carboxy functionality of the appropriate cyclopropylketo-α,α-dimethylphenylacetic acid compound of structure (47) may be esterified by techniques and procedures well known and appreciated by one of ordinary skill in the art to give the corresponding cyclopropylketo-α,α-dimethylphenylacetic acid ester compound of structure (32) as described previously in step d.

In step p, the nitrile functionality of the appropriate cyclopropyl cyanocumylketone compound of structure (20) is converted to the corresponding carboxy to give the cyclopropylketo-α,α-dimethylphenylacetic acid compound of structure (47) as described previously in step e.

In step q, the amide functionality of the appropriate cyclopropylketo-α,α-dimethylphenylacetic acid amide compound of structure (41) is converted to the corresponding acid by acid hydrolysis as is known in the art to give the corresponding cyclopropylketo-α,α-dimethylphenylacetic acid compound of structure (47) as described previously in step f.

In addition, step q and step k may be combined and the ω'-halo-α'-keto-α,α-dimethylphenylacetic acid compound of structure (46) wherein n=3 may be prepared from the corresponding cyclopropylketo-α,α-dimethylphenylacetic acid amide compound of structure (41) as described previously in Scheme A, step j.

In step r, the carboxy functionality of the appropriate cyclopropylketo-α,α-dimethylphenylacetic acid compound of structure (47) may be amidated by techniques and procedures well known and appreciated by one of ordinary skill in the art to give the corresponding cyclopropylketo-α,α-dimethylphenylacetic acid amide compound of structure (41) as described previously in step g.

In step s, the α-halo functionality of the appropriate cyclopropyl halocumylketone compound of structure (11) is carboxylated to give the corresponding cyclopropylketo-α,α-dimethylphenylacetic acid compound of structure (47) as described previously in step h.

In step t, the appropriate the amide functionality of the appropriate cyclopropylketo-α,α-dimethylphenylacetic acid amide compound of structure (41) is converted to the corresponding ester to give the cyclopropylketo-α,α-dimethylphenylacetic acid ester compound of structure (32) as described previously in step i.

In step u, the nitrile functionality of the appropriate ω-halo-cyanoethylphenylketone compound of structure (21) is converted to the corresponding ester by reaction with an appropriate $C_1$ to $C_6$ alcohol to give the ω'-halo-α'-keto-α- methylphenylacetic acid ester compound of structure (33) as described previously in step a.

In step v, the nitrile functionality of the appropriate ω-halo-cyanoethylphenylketone compound of structure (21) is converted to the corresponding amide to give the ω'-halo-α'-keto-α-methylphenylacetic acid amide compound of structure (42) wherein $R_6$ and $R_7$ are both hydrogen as described previously in step b.

In step w, the carboxy ester functionality of the appropriate ω'-halo-α'-keto-α-methylphenylacetic acid ester compound of structure (33) is hydrolyzed to give the corresponding ω'-halo-α'-keto-α-methylphenylacetic acid compound of structure (48) as described previously in step c.

In step x, the carboxy functionality of the appropriate ω'-halo-α'-keto-α-methylphenylacetic acid compound of structure (48) may be esterified by techniques and procedures well known and appreciated by one of ordinary skill in the art to give the corresponding ω-halo-α'-keto-α-methylphenylacetic acid ester compound of structure (33) as described previously in step d.

Alternatively, step ee and step x may be combined and the ω'-halo-α'-keto-α,α-dimethylphenylacetic acid ester compound of structure (33) wherein n=3 may be prepared from the corresponding cyclopropylketo-α-methylphenylacetic acid compound of structure (49) as described previously in step d.

Alternatively, step jj, step ee and step x may be combined and the ω'-halo-α'-keto-α,α-dimethylphenylacetic acid ester compound of structure (33) wherein n=3 may be prepared from the corresponding cyclopropyl cyanoethylphenylketone compound of structure (23) as described previously in step d.

In step y, the nitrile functionality of the appropriate ω-halo-cyanoethylphenylketone compound of structure (21) is converted to the corresponding carboxy to give the ω'-halo-α'-keto-α-methylphenylacetic acid compound of structure (48) as described previously in step e.

In step z, the amide functionality of the appropriate ω'-halo-α'-keto-α-methylphenylacetic acid amide compound of structure (42) is converted to the corresponding acid by acid hydrolysis as is known in the art to give the ω'-halo-α'-keto-α-methylphenylacetic acid compound of structure (48) as described previously in step f.

In step aa, the carboxy functionality of the appropriate ω'-halo-α'-keto-α-methylphenylacetic acid compound of structure (48) may be amidated by techniques and procedures well known and appreciated by one of ordinary skill in the art to give the corresponding ω'-halo-α'-keto-α-methylphenylacetic acid amide compound of structure (42) as described previously in step g.

In step bb, the α-halo functionality of the appropriate ω-halo-haloethylphenylketone compound of structure (12) is carboxylated to give the corresponding ω'-halo-α'-keto-α-methylphenylacetic acid compound of structure (48) as described previously in step h.

In step cc, the appropriate the amide functionality of the appropriate ω'-halo-α'-keto-α-methylphenylacetic acid amide compound of structure (42) is converted to the corresponding ester to give the ω'-halo-α'-keto-α-methylphenylacetic acid ester compound of structure (33) as described previously in step i.

In step dd, the appropriate ω'-halo-α'-keto-α-methylphenylacetic acid compound of structure (48) wherein n=3 is ring-closed to give the corresponding cyclopropylketo-α-methylphenylacetic acid compound of structure (49) as described previously in Scheme A, step k.

In step ee, the appropriate cyclopropylketo-α-methylphenylacetic acid compound of structure (49) is ring-opened to give the corresponding ω'-halo-α'-keto-α-methylphenylacetic acid compound of structure (48) wherein n=3 as described previously in Scheme A, step j.

In step ff, the nitrile functionality of the appropriate cyclopropyl cyanoethylphenylketone compound of structure (23) is converted to the corresponding ester by reaction with an appropriate $C_1$ to $C_6$ alcohol to give the cyclopropylketo-α-methylphenylacetic acid ester compound of structure (35) as described previously in step a.

In step gg, the nitrile functionality of the appropriate cyclopropyl cyanoethylphenylketone compound of structure (23) is converted to the corresponding amide to give the cyclopropylketo-α-methylphenylacetic acid amide compound of structure (44) wherein $R_6$ and $R_7$ are both hydrogen as described previously in step b.

In step hh, the carboxy ester functionality of the appropriate cyclopropylketo-α-methylphenylacetic acid ester compound of structure (35) is hydrolyzed to give the corresponding cyclopropylketo-α-methylphenylacetic acid compound of structure (49) as described previously in step c.

In step ii, the carboxy functionality of the appropriate cyclopropylketo-α-methylphenylacetic acid compound of structure (49) may be esterified by techniques and procedures well known and appreciated by one of ordinary skill in the art to give the corresponding cyclopropylketo-α-methylphenylacetic acid ester compound of structure (35) as described previously in step d.

In step jj, the nitrile functionality of the appropriate cyclopropyl cyanoethylphenylketone compound of structure (23) is converted to the corresponding carboxy to give the cyclopropylketo-α-methylphenylacetic acid compound of structure (49) as described previously in step e.

In step kk, the amide functionality of the appropriate cyclopropylketo-α-methylphenylacetic acid amide compound of structure (44) is converted to the corresponding acid by acid hydrolysis as is known in the art to give the corresponding cyclopropylketo-α-methylphenylacetic acid compound of structure (49) as described previously in step f.

In addition, step kk and step ee may be combined and the ω'-halo-α'-keto-α-methylphenylacetic acid compound of structure (48) wherein n=3 may be prepared from the corresponding cyclopropylketo-α-methylphenylacetic acid amide compound of structure (44) as described previously in Scheme A, step j.

In step 11, the carboxy functionality of the appropriate cyclopropylketo-α-methylphenylacetic acid compound of structure (49) may be amidated by techniques and procedures well known and appreciated by one of ordinary skill in the art to give the corresponding cyclopropylketo-α- methylphenylacetic acid amide compound of structure (44) as described previously in step g.

In step mm, the α-halo functionality of the appropriate cyclopropyl haloethylphenylketone compound of structure (14) is carboxylated to give the corresponding cyclopropylketo-α-methylphenylacetic acid compound of structure (49) as described previously in step h.

In step nn, the appropriate the amide functionality of the appropriate ω'-halo-α'-keto-α-methylphenylacetic acid amide compound of structure (42) is converted to the corresponding ester to give the ω'-halo-α'-keto-α-methylphenylacetic acid ester compound of structure (33) as described previously in step i.

In step oo, the nitrile functionality of the appropriate ω-halo cyanotolylketone compound of structure (22) is converted to the corresponding ester by reaction with an appropriate $C_1$ to $C_6$ alcohol to give the ω'-halo-α'-keto-phenylacetic acid ester compound of structure (34) as described previously in step a.

In step pp, the nitrile functionality of the appropriate ω-halo cyanotolylketone compound of structure (22) is converted to the corresponding amide to give the ω'-halo-α'-keto-phenylacetic acid amide compound of structure (43) wherein $R_6$ and $R_7$ are both hydrogen as described previously in step b.

In step qq, the carboxy ester functionality of the appropriate ω'-halo-α'-keto-phenylacetic acid ester compound of structure (34) is hydrolyzed to give the corresponding ω'-halo-α'-keto-methylphenylacetic acid compound of structure (50) as described previously in step c.

In step rr, the carboxy functionality of the appropriate ω'-halo-α'-keto-methylphenylacetic acid compound of structure (50) may be esterified by techniques and procedures well known and appreciated by one of ordinary skill in the art to give the corresponding ω'-halo-α'-keto-phenylacetic acid ester compound of structure (34) as described previously in step d.

Alternatively, step yy and step rr may be combined and the ω'-halo-α'-keto-phenylacetic acid ester compound of structure (34) wherein n=3 may be prepared from the corresponding ω'-halo-α'-keto-methylphenylacetic acid compound of structure (50) as described previously in step d.

Alternatively, step ddd, step yy and step rr may be combined the ω'-halo-α'-keto-phenylacetic acid ester compound of structure (34) wherein n=3 may be prepared from the corresponding cyclopropyl cyanotolylketone compound of structure (24) as described previously in step d.

In step ss, the nitrile functionality of the appropriate ω-halo cyanotolylketone compound of structure (22) is converted to the corresponding carboxy to give the ω'-halo-α'-keto-methylphenylacetic acid compound of structure (50) as described previously in step e.

In step tt, the amide functionality of the appropriate ω'-halo-α'-keto-phenylacetic acid amide compound of structure (43) is converted to the corresponding acid by acid hydrolysis as is known in the art to give the ω'-halo-α'-keto-methylphenylacetic acid compound of structure (50) as described previously in step f.

In step uu, the carboxy functionality of the appropriate ω'-halo-α'-keto-methylphenylacetic acid compound of structure (50) may be amidated by techniques and procedures well known and appreciated by one of ordinary skill in the art to give the corresponding ω'-halo-α'-keto-phenylacetic acid amide compound of structure (43) as described previously in step g.

In step vv, the α-halo functionality of the appropriate ω-halo halotolylketone compound of structure (13) is carboxylated to give the corresponding ω'-halo-α'-keto-methylphenylacetic acid compound of structure (50) as described previously in step h.

In step ww, the appropriate the amide functionality of the appropriate ω'-halo-α'-keto-phenylacetic acid amide compound of structure (43) is converted to the corresponding ester to give the ω'-halo-α'-keto-phenylacetic acid ester compound of structure (34) as described previously in step i.

In step xx, the appropriate ω'-halo-α'-keto-methylphenylacetic acid compound of structure (50) wherein n=3 is ring-closed to give the corresponding cyclopropylketo-phenylacetic acid compound of structure (51) as described previously in Scheme A, step k.

In step yy, the appropriate cyclopropylketo-phenylacetic acid compound of structure (51) is ring-opened to give the corresponding ω'-halo-α'-keto-methylphenylacetic acid compound of structure (50) wherein n=3 as described previously in Scheme A, step j.

In step zz, the nitrile functionality of the appropriate cyclopropyl cyanotolylketone compound of structure (24) is converted to the corresponding ester by reaction with an appropriate $C_1$ to $C_6$ alcohol to give the cyclopropylketo-phenylacetic acid ester compound of structure (36) as described previously in step a.

In step aaa, the nitrile functionality of the appropriate cyclopropyl cyanotolylketone compound of structure (24) is converted to the corresponding amide to give the cyclopropylketo-phenylacetic acid amide compound of structure (45) wherein $R_6$ and $R_7$ are both hydrogen as described previously in step b.

In step bbb, the carboxy ester functionality of the appropriate cyclopropylketo-phenylacetic acid ester compound of structure (36) is hydrolyzed to give the corresponding cyclopropylketo-phenylacetic acid compound of structure (51) as described previously in step c.

In step ccc, the carboxy functionality of the appropriate cyclopropylketo-phenylacetic acid compound of structure (51) may be esterified by techniques and procedures well known and appreciated by one of ordinary skill in the art to give the corresponding cyclopropylketo-phenylacetic acid ester compound of structure (36) as described previously in step d.

In step ddd, the nitrile functionality of the appropriate cyclopropyl cyanotolylketone compound of structure (24) is converted to the corresponding carboxy to give the cyclopropylketo-phenylacetic acid compound of structure (51) as described previously in step e.

In step eee, the amide functionality of the appropriate cyclopropylketo-phenylacetic acid amide compound of structure (45) is converted to the corresponding acid by acid hydrolysis as is known in the art to give the corresponding cyclopropylketo-phenylacetic acid compound of structure (51) as described previously in step f.

In addition, step yy and step eee may be combined and the ω'-halo-α'-keto-methylphenylacetic acid compound of structure (50) wherein n=3 may be prepared from the corresponding cyclopropylketo-phenylacetic acid amide compound of structure (45) as described previously in Scheme A, step j.

In step fff, the carboxy functionality of the appropriate cyclopropylketo-phenylacetic acid compound of structure (51) may be amidated by techniques and procedures well known and appreciated by one of ordinary skill in the art to give the corresponding cyclopropylketo-phenylacetic acid amide compound of structure (45) as described previously in step g.

In step ggg, the α-halo functionality of the appropriate cyclopropyl halotolylketone of structure (15) is carboxylated to give the corresponding cyclopropylketo-phenylacetic acid compound of structure (51) as described previously in step h.

In step hhh, the appropriate the amide functionality of the appropriate cyclopropylketo-phenylacetic acid amide compound of structure (45) is converted to the corresponding ester to give the cyclopropylketo-phenylacetic acid ester compound of structure (36) as described previously in step i.

Starting materials for use in Scheme H are readily available to one of ordinary skill in the art.

The following examples present typical syntheses as described in Scheme E. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "$\mu$L" refers to microliters; "$\mu$g" refers to micrograms; and "$\mu$M" refers to micromolar.

EXAMPLE 26

Step a: 2-[4-(4-Chloro-butyryl)-phenyl]-2-methyl-propionic Acid, Methyl Ester

Place anhydrous methanol (5 mL) under argon, cool to 0° C. and add hydrogen chloride until saturated. Add 2-[4-(4-chloro-butyryl)-phenyl]-2-methyl-propionitrile (103 mg, 4.12 mmol), remove the ice bath and stir for 5 hours at room temperature. Allow to stand at −10° C. overnight, and stir an additional 3 hours at room temperature. Pour into cracked ice (20 g) and allow to stand for 5 minutes. Evaporate the solvent in vacuo to 1/2 volume, dilute with water and extract with methylene chloride (3×). Combine the organic layers, wash with saturated sodium hydrogen carbonate and brine. Dry (MgSO$_4$), filter and evaporate the solvent in vacuo. Extract the residue into hot hexane (12 mL), filter hot and evaporate the solvent in vacuo to give the title comound as a colorless oil (97 mg, 83%).

EXAMPLE 27

Step d: 2-[4-(4-Chloro-butyryl)-phenyl]-2-methyl-propionic Acid, Ethyl Ester

Add anhydrous hydrogen chloride gas (18.0 g) to anhydrous ethanol DB (210 g) by purging the solution. Add this hot solution (60° C.) to a solution of 2-[4-(4-chloro-butyryl)-phenyl]-2-methyl-propionic acid (31 g, 115.6 mmol) and reflux under a nitrogen atmosphere for 2.5 hours. Evaporate the solvent in vacuo, dissolve the residue in methylene chloride (150 mL) and wash with water (2×100 mL). Dry (MgSO$_4$), filter through silica gel, washing the gel with methylene chloride (250 mL). Combine the organic washings and evaporate the solvent in vacuo to give the title compound as a colorless oil (33.3 g, 97%).

$^1$H NMR (300 MHz, CDCl$_3$) $\delta$7.96 (d, J=8.3 Hz, 2H), 7.45 (d, J=8.3 Hz, 2H), 4.15 (q, J=7.1 Hz, 2H), 3.70 (t, J=6.6 Hz, 2H), 3.19 (t, J=6.8 Hz, 2H), 2.25 (p, J=6.6 Hz, 2H), 1.61 (s, 6H), 1.20 (q, J=7.1 Hz, 3H); $^{13}$C NMR (75 MHz, CDCl$_3$) $\delta$198.4, 176.0, 150.3, 135.1, 128.1, 126.0, 61.0, 46.8, 44.6, 35.2, 26.7, 26.3, 14.0; IR (neat) 2978, 1728, 1686, 1606, 1254, 1231, 1148, 1097 cm$^{-1}$.

Anal. Calcd for C$_{16}$H$_{21}$O$_3$Cl: C, 64.75; H, 7.13; Found: C, 64.24; H, 7.18.

EXAMPLE 28

Step d: 2-[4-(4-Chloro-butyryl)-phenyl]-2-methyl-propionic Acid, Methyl Ester

Dissolve 2-[4-(4-chloro-butyryl)-phenyl]-2-methyl-propionic acid (6.2 g, 23.1 mmol) in hot methanolic solution of anhydrous hydrogen chloride (42 mL of a methanol containing 3.2 g of anhydrous hydrogen chloride). Reflux for 42 minutes, evaporate the solvent in vacuo, dissolve the residue in methylene chloride and wash with water. Dry (MgSO$_4$), filter through silica gel, washing the gel with methylene chloride. Combine the organic washings and evaporate the solvent in vacuo to give the title compound as a clear oil (6.21 g, 94%).

$^1$H NMR (30 MHz, CDCl$_3$) $\delta$7.95 (d, J=8.5 Hz, 2H), 7.44 (d, J=8.5 Hz, 2H), 3.66 (s, 3H), 3.67 (t, J=6.6 Hz, 2H), 3.17 (t, J=6.6 Hz, 2H), 2.30 (p, J=6.6 Hz, 2H), 1.61 (s, 6H); $^{13}$C NMR (75 MHz, CDCl$_3$) $\delta$198.0, 176.2, 149,8, 135.0, 128.0, 125.8, 52.4, 46.9, 44.7, 35.3, 26.8, 26.5.

Anal. Calcd for C$_{15}$H$_{19}$O$_3$Cl: C, 63.72; H, 6.77; Found: C, 63.50; H, 6.67.

EXAMPLE 29

Step d: 2-[4-(4-Chloro-butyryl)-phenyl]-2-methyl-propionic Acid, Methyl Ester

Mix 2-[4-(4-chloro-butyryl)-phenyl]-2-methyl-propionic acid (10.0 g, 37.3 mmol) and anhydrous potassium carbonate (3.5 g, 25.3 mmol). Heat to 40° C. in acetonitrile (100 mL) and stir under a nitrogen atmosphere. Add dimethyl sulfate (13.3 g, 105 mmol) and reflux for 45 minutes. Evaporate the solvent in vacuo, dissolve the residue in ethyl acetate (50 mL) and wash with water (4×50 mL). Dry (MgSO$_4$), filter through silica gel and evaporate the solvent in vacuo to give the title compound (6.4 g, 89%).

EXAMPLE 30

Step h: 2-[4-(4-Chloro-butyryl)-phenyl]-2-methyl-propionic Acid

Fit a jacketed glass cell of about 6 L capacity with a rotating expanded silver mesh cathode/magnesium anode assembly, a carbon dioxide delivery tube, and a stainless steel thermocouple. Load the cell with acetonitrile (5.8 L) and tetraethylammonium bromide (26 g). Sparge with carbon dioxide and cool in cooling bath. When the contents of the cell reach −10° C., add hydrogen chloride remediated 1-[4-(1-bromo-1-methyl-ethyl)-phenyl]-4-chloro-butan-1-one and 1-[4-(1-chloro-1-methyl-ethyl)-phenyl]-4-chloro-butan-1-one (424.9 g, 53.5 mole % bromo and 20.4 mole % chloro by HPLC analysis, 1087 mmol total active tertiary benzylic halide) and perform electrolysis at a controlled current of 8 amps (20 mA cm$^{-2}$) for 6 hours. Drain the contents, acidify with chilled aqueous 6M hydrochloric acid, extract, evaporate the solvent in vacuo and recrystallize to give the title compound (186 g, 64%); 78.5–80.3° C.

$^1$H NMR (300 MHz, CDCl$_3$) δ10.5 (br s, 2H), 7.96 (d, J=8.2 Hz, 2H), 7.50 (d, J=8.2 Hz, 2H), 3.67 (t, J=6.8 Hz, 2H), 3.17 (t, J=6.8 Hz, 2H), 2.22 (m, J=6.7 Hz, 2H), 1.63 (s, 6H); $^{13}$C NMR (75 MHz, CDCl$_3$) δ198.2, 181.9, 149.0, 135.2, 128.1, 126.1, 46.7, 44.7, 35.3, 26.9, 26.7; MS (CIMS (Methane)) 271 (3), 269 (11), 233 (100), 187 (75).

Anal. Calcd for C$_{14}$H$_{17}$O$_3$Cl: C, 62.57; H, 6.38; Found: C, 63.10; H, 6.59.

EXAMPLE 31

Step h: 2-[4-(4-Chloro-butyryl)-phenyl]-2-methyl-propionic Acid

Fit a jacketed glass cell of about 50 mL capacity with an expanded silver mesh cathode (14 cm$^2$ geometric area), a roughly concentric magnesium sacrificial anode, a tube to deliver carbon dioxide gas and a magnetic stir bar. Add a solution of hydrogen chloride remediated 1-[4-(1-bromo-1-methyl-ethyl)-phenyl]-4-chloro-butan-1-one and 1-[4-(1-chloro-1-methyl-ethyl)-phenyl]-4-chloro-butan-1-one (2.79 g, 89 mole %, 3:1 ratio of tertiary benzylic bromide to tertiary benzylic chloride by NMR, approximately 8.6 mmol total active tertiary benzylic halide) in acetonitrile (45 mL) and tetraethylammonium bromide (0.19 g). Close the cell and cool to −10° C. with a continuous carbon dioxide sparge for 169 minutes at an average current density of 13 mA cm$^{-2}$. Warm to contents of the cell to ambient temperature, drain the contents, acidify with chilled aqueous 6M hydrochloric acid, extract and evaporate the solvent in vacuo to give the title compound (1.53 g, 66%).

EXAMPLE 32

Step h: 2-[4-(4-Chloro-butyryl)-phenyl]-2-methyl-propionic Acid

Fit a jacketed glass cell of 50 mL capacity with an expanded silver mesh cathode (14 cm2 geometric area), a roughly concentric magnesium sacrificial anode, a tube to deliver carbon dioxide gas, and a magnetic stir bar. Cool the cell to −10° C. under carbon dioxide. Add a solution of tetraethylammonium chloride (40 mL of a 0.02M solution in dimethylformamide) and 1-[4-(1-chloro-1-methyl-ethyl)-phenyl]-4-chloro-butan-1-one (2.91 g, 85% pure by NMR, 9.81 mmol) and carry out electrolysis for 178 minutes at an average current density of 12.4 mA cm−2; the total charge passed is equal to 98% of the calculated theoretical two electron value. Warm the contents of the cell to ambient temperature, drain the contents, acidify with chilled aqueous 6M hydrochloric acid, extract and evaporate the solvent in vacuo to give the title compound (1.89 g, 72%).

EXAMPLE 33

Step m: 2-(4-Cyclopropanecarbonyl-phenyl)-2-methyl-propionamide

Dissolve 2-(4-cyclopropanecarbonyl-phenyl)-2-methyl-propionitrile (100 mg) in aqueous ethanolic potassium hydroxide (2 mL) (prepared from ethanol (5 mL), water (5 mL) and solid potassium hydroxide (1.5 g). Stir overnight at room temperature, then heat at reflux for 6 hours. Cool and evaporate the solvent in vacuo to give the title compound.

EXAMPLE 34

Step t: 2-(4-Cyclopropanecarbonyl-phenyl)-2-methyl-propionic Acid, Ethyl Ester

Dissolve 2-(4-cyclopropanecarbonyl-phenyl)-2-methyl-propionamide (100 mg) in ethanol and bubble in hydrochloride gas for 5 minutes while stirring. Reflux for 10 hours, distill off the ethanol and extract into ethyl acetate. Evaporate the solvent in vacuo to give the title compound as an oil (50 mg).

EXAMPLE 35

Step k and step q: 2-[4-(4-Bromo-butyryl)-phenyl]-2-methyl-propionic Acid

Treat 2-(4-cyclopropanecarbonyl-phenyl)-2-methyl-N-methyl-N-methoxy-propionamide (0.15 g, 0.53 mmol) with 48% HBr (1 mL) for 2 hours at 80° C. Cool to room temperature, dilute with water (5 mL) and neutralize with aqueous sodium hydrogen carbonate until pH 7. Extract with methylene chloride (3×15 mL), dry (Na$_2$SO$_4$), filter and evaporate the solvent in vacuo. Purify by silica gel chromatography (3:1 hexane/ethyl acetate) to give the title compound (0.15 g, 95%).

$^1$H NMR (CDCl$_3$) δ7.97 (d, 2H), 7.51 (d, 2H), 3.53 (t, 2H), 3.16 (t, 2H), 2.30 (quin, 2H), 1.60 (s, 6H); $^{13}$C NMR (CDCl$_3$) δ198.4, 181.8, 149.5, 131.0, 128.3, 126.3, 46.6, 36.5, 33.6, 26.9, 26.1; MS (CI) (M$^+$+H) 303 (100), 315 (98), 233 (80).

EXAMPLE 36

Step p: 2-(4-Cyclopropanecarbonyl-phenyl)-2-methyl-propionic Acid

Combine 2-(4-cyclopropanecarbonyl-phenyl)-2-methyl-propionitrile (0.5 g) in 12.5% sodium hydroxide (20 mL) and ethanol (12.5 mL). Heat to reflux for 21 hours, cool and remove the ethanol by vacuum distillation. Extract the residual aqueous suspension with methylene chloride (40 mL), acidify the aqueous phase with 20% HCl and extract with methylene chloride (2×40 mL). Combine the organic phases, dry (Na$_2$SO$_4$) and evaporate the solvent in vacuo to give the title compound as a crystalline solid (350 mg, 70%); mp 83–85° C.

$^1$H NMR (CDCl$_3$) δ7.50–8.00 (4H, d), 2.66 (1H, m), 1.62 (6H, s), 1.24 (2H, m), 1.04 (2H, m).

The following compounds can be prepared by using the procedures depicted in Scheme H:

(4-Cyclopropanecarbonyl-phenyl)-acetic acid;
2-(4-Cyclopropanecarbonyl-phenyl)-propionic acid;
2-(4-Cyclopropanecarbonyl-phenyl)-2-methyl-propionic acid;
[4-(4-Chloro-butyryl)-phenyl)-acetic acid;
2-[4-(4-Chloro-butyryl)-phenyl]-propionic acid;
2-[4-(4-Chloro-butyryl)-phenyl]-2-methyl-propionic acid;
(4-Cyclopropanecarbonyl-phenyl)-acetic acid, ethyl ester;
2-(4-Cyclopropanecarbonyl-phenyl)-propionic acid, ethyl ester;
[4-(4-Chloro-butyryl)-phenyl]-acetic acid, ethyl ester;
2-[4-(4-Chloro-butyryl)-phenyl]-propionic acid, ethyl ester;
2-[4-(4-Chloro-butyryl)-phenyl]-2-methyl-propionic acid, ethyl ester;
(4-Cyclopropanecarbonyl-phenyl)-acetamide;
2-(4-Cyclopropanecarbonyl-phenyl)-propionamide;
[4-(4-Chloro-butyryl)-phenyl]-acetamide;
2-[4-(4-Chloro-butyryl)-phenyl]-propionamide; and
2-[4-(4-Chloro-butyryl)-phenyl]-2-methyl-propionamide.

In addition, the novel intermediate of formula (II) wherein R$_5$ is COOH may be prepared as described in Scheme I. In Scheme I, all substituents are as previously defined unless otherwise indicated.

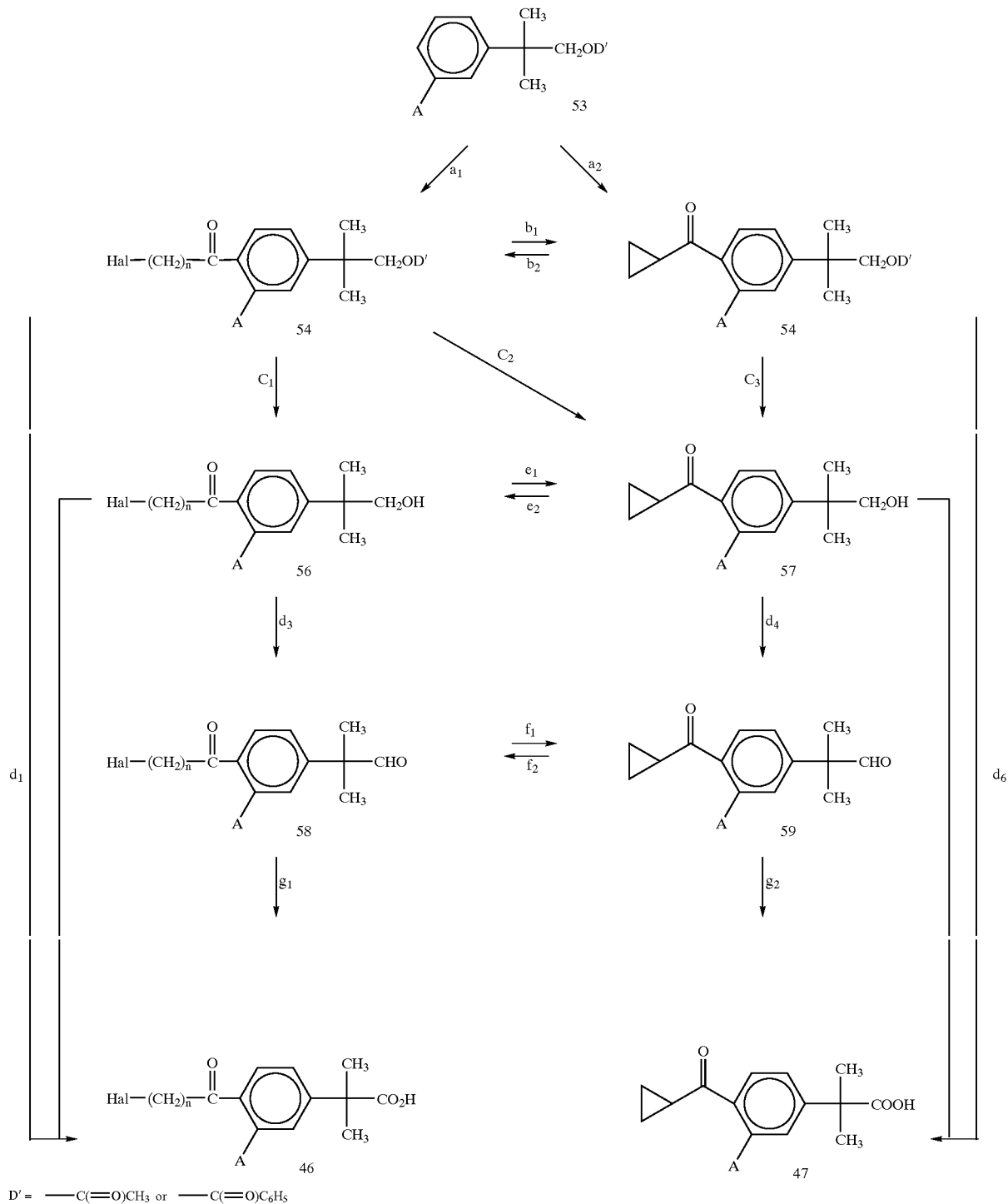

D' = —C(=O)CH₃ or —C(=O)C₆H₅

Scheme I provides a general synthetic procedure for preparing the novel intermediate of formula (II) wherein $R_5$ is COOH.

In step a, the neophyl acetate of benzoate of structure (53) is acylated with an appropriate ω-halo compound of the structure Hal-$(CH_2)_n$—C(=O)—B, wherein B is Hal or hydroxy, Hal is Cl, Br or I and n is as previously defined to give the corresponding ω'-halo-α'-keto-(2-methylpropanol) benzene acetate or benzoate compound of structure (54) as described previously in Scheme A, step d.

The neophyl acetate of benzoate of structure (53) is prepared by reacting a methallyl halide of structure

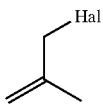

wherein Hal is Cl, Br or I with sodium acetate or sodium benzoate in a suitable organic solvent such as 1-methyl-2-pyrrolidinone. The reactants are heated at a temperature of approximately 100 to 130° C. and the corresponding to give the methallyl acetate or benzoate of structure

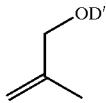

wherein D' is —C(=O)CH$_3$ or —C(=O)C$_6$H$_5$ which is collected by distillation.

A benzene compound of structure

wherein A is defined above is then alkylated with the methylallyl acetate or benzoate of structure

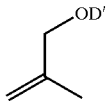

wherein D' is —C(=O)CH$_3$ or —C(=O)C$_6$H$_5$ to give the neophyl acetate or benzoate of structure (53) as described previously in Scheme A, step d.

In step a$_2$, the neophyl acetate or benzoate of structure (53) is acylated with an appropriate cyclopropyl compound of the structure

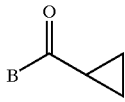

wherein B is as previously defined to give the corresponding cyclopropyl neophyl acetate or benzoate of structure (55) as described previously in Scheme A, step e.

In step b$_1$, the appropriate ω'-halo-α'-keto-(2-methylpropanol)benzene acetate or benzoate compound of structure (54) wherein n=3 is ring-closed to give the corresponding cyclopropyl neophyl acetate or benzoate of structure (55) as described previously in Scheme A, step k.

In step b$_2$, the appropriate cyclopropyl neophyl acetate or benzoate of structure (55) is ring-opened to give the corresponding ω'-halo-α'-keto-(2-methylpropanol)benzene acetate or benzoate compound of structure (54) wherein n=3 as described previously in Scheme H, step j.

In step c$_1$, the acetate or benzoate functionality of the appropriate ω'-halo-α'-keto-(2-methylpropanol)benzene acetate or benzoate compound of structure (54) is hydrolyzed with concentrated hydrochloric acid in ethanol at reflux temperature for a period of time ranging from 1–10 hours. The corresponding ω'-halo-α'-keto-(2-methylpropanol)benzene compound of structure (56) is recovered from the reaction zone by extractive methods as is known in the art.

In step c$_2$, the appropriate ω'-halo-α'-keto-(2-methylpropanol)benzene acetate or benzoate compound of structure (54) wherein n=3 is ring closed and the acetate or benzoate functionality hydrolyzed with base to give the cyclopropyl neophyl alcohol compound of structure (57).

For example, the appropriate ω'-halo-α'-keto-(2-methylpropanol)benzene acetate or benzoate compound of structure (54) wherein n=3 is reacted with 40% aqeuous tetrabutylammonium hydroxide and 50% aqeuous sodium hydroxide at reflux temperature for a period of time ranging from 5–72 hours. The cyclopropyl neophyl alcohol compound of structure (57) may be recovered from the reaction zone by extractive methods as are known in the art.

In step c$_3$, the acetate or benzoate functionality of the appropriate cyclopropyl neophyl acetate or benzoate of structure (55) is hydrolyzed to give the corresponding cyclopropyl neophyl alcohol of structure (57).

For example, the appropriate cyclopropyl neophyl acetate or benzoate of structure (55) is reacted with 50% aqueous sodium hydroxide at reflux temperature for a period of time ranging from 5 minutes to 5 hours. The corresponding cyclopropyl neophyl alcohol of structure (57) is recovered from the reaction zone by extractive methods as are known in the art.

In step d$_1$, the ω'-halo-α'-keto-(2-methylpropanol) benzene acetate or benzoate compound of structure (54) is converted to the corresponding ω'-halo-α'-keto-α,α-dimethylphenylacetic acid compound of structure (46).

For example, the appropriate cyclopropyl neophyl alcohol of structure (54) may be reacted with ruthenium chloride/sodium periodate in a suitable organic solvent such as acetonitrile and/or carbon tetrachloride, ruthenium chloride/sodium hypochloride in a suitable solvent such as acetic acid/water, potassium permanganate in a suitable solvent such as acetic acid/water, fumic nitric acid in acetic acid or sodium nitrite/concentrated nitric acid in acetic acid. The reactants are typically mixed stirred together at a temperature range of 10° C. to 50° C. and for a period of time ranging from 30 minutes to 10 hours. The corresponding cyclopropylketo-α,α-dimethylphenylacetic acid compound of structure (46) is recovered from the reaction zone by extractive methods as is known in the art.

In step d$_2$, the ω'-halo-α'-keto-(2-methylpropanol) benzene compound of structure (56) is converted to the corresponding ω'-halo-α'-keto-α,α-dimethylphenylacetic acid compound of structure (46).

For example, the appropriate ω'-halo-α'-keto-(2-methylpropanol)benzene compound of structure (56) may be oxidized with potassium permanganate in suitable acid solvent such as acetic acid. The reactants are typically reacted at a temperature range of from about 0° C. to 5° C. for a period of time ranging from 30 minutes to 10 hours. The corresponding ω'-halo-α'-keto-α,α-dimethylphenylacetic acid compound of structure (46) is recovered from the reaction zone by extractive methods as are known in the art and may be purified by recrystallization. Other oxidizing reagents suitable for the oxidation of the appropriate ω'-halo-α'-keto-(2-methylpropanol)benzene compound of structure (56) to the corresponding ω'-halo-α'-keto-α,α-dimethylphenylacetic acid compound of structure (46) are nitric acid, chromium (IV) oxide, nitrogen dioxide, ruthenium (VIII) oxide, nickel peroxide, silver oxide, t-butyl chromate, xenic acid.

In step $d_3$, the hydroxymethyl functionality of the appropriate ω'-halo-α'-keto-(2-methylpropanol)benzene compound of structure (56) is oxidized with a variety of oxidizing agents and methods to give the corresponding ω'-halo-α'-keto-α,α-dimethylphenylacetaldehyde compound of structure (58).

One such method involves a procedure in which the hydroymethyl functionality of the appropriate ω'-halo-α'-keto-(2-methylpropanol)benzene compound of structure (56) is oxidized to the corresponding aldehyde functionality using, for example, Swern Oxidation conditions (dimethyl sulfoxide, oxalyl chloride and triethylamine), as is known in the art. The Swern Oxidation is carried out in a suitable aprotic organic solvent such as methylene chloride at temperatures ranging from about −78° C. to room temperature, and the reaction time vaires from about ½ hours to 8 hours. Other suitable reagents for the oxidation of the hydroxyethyl functionality of the appropriate ω'-halo-α'-keto-(2-methylpropanol)benzene compound of structure (56) to the corresponding ω'-halo-α'-keto-α,α-dimethylphenylacetaldehyde compound of structure (58) are Dess-Martin reagent, chromium (IV) oxide, nickel peroxide, sodium dichromate, potassium dichromate, t-butyl chromate, silver oxide, argentic picolinate, manganese dioxide, lead tetraacetate, dicyclohexylcarbodiimide, 2,3-dichloro-5,6-dicyanoquinone, tetrachloro-1,2-benzoquinone, 2,2,6,6-tetramethylpiperidinyl-1-oxy (TEMPO) or quinolinium chlorochromate.

In step $d_4$, the hydroxymethyl functionality of the appropriate cyclopropyl neophyl alcohol of structure (57) is oxidized to give the corresponding cyclopropylketo-α,α-dimethylphenylacetaldehyde compound of structure (59) as described previously in step $d_3$.

In step $d_5$, the appropriate cyclopropyl neophyl alcohol of structure (57) is converted to the corresponding cyclopropylketo-α,α-dimethylphenylacetic acid compound of structure (47) as described previously in step $d_2$.

In step $d_6$, the appropriate cyclopropyl neophyl acetate or benzoate of structure (55) is converted to the corresponding cyclopropylketo-α,α-dimethylphenylacetic acid compound of structure (47) as described previously in step $d_f$.

In step $e_1$, the appropriate ω'-halo-α'-keto-(2-methylpropanol)benzene compound of structure (56) wherein n=3 is ring-closed to give the corresponding cyclopropyl neophyl alcohol of structure (57) as described previously in Scheme H, step j.

In step $e_2$, the appropriate cyclopropyl neophyl alcohol of structure (57) is ring-opened to give the corresponding ω'-halo-α'-keto-(2-methylpropanol)benzene compound of structure (56) wherein n=3 as described previously in Scheme H, step k.

In step $f_1$, the appropriate ω'-halo-α'-keto-α,α-dimethylphenylacetaldehyde compound of structure (58) wherein n=3 is ring-closed to give the corresponding cyclopropylketo-α,α-dimethylphenylacetaldehyde compound of structure (59) as described previously in Scheme H, step j.

In step $f_2$, the appropriate cyclopropylketo-α,α-dimethylphenylacetaldehyde compound of structure (59) is ring-opened to give the corresponding ω'-halo-α'-keto-α,α-dimethylphenylacetaldehyde compound of structure (58) wherein n=3 as described previously in Scheme H, step k.

In step $g_1$, the aldehyde functionality of the appropriate ω'-halo-α'-keto-α,α-dimethylphenylacetaldehyde compound of structure (58) is oxidized to give the corresponding ω'-halo-α'-keto-α,α-dimethylphenylacetic acid compound of structure (46).

For example, the appropriate ω'-halo-α'-keto-α,α-dimethylphenylacetaldehyde compound of structure (58) is reacted with, for example, potassium permanganate. The potassium permanganate oxidation is carried out in a suitable acidic medium such as hydrochloric acid/acetone at a temperature ranging from about 0° C. to room temperature and the reaction time varies from about ½ hour to 8 hours. Other suitable reageants for the oxidation of the ω'-halo-α'-keto-α,α-dimethylphenylacetaldehyde compound of structure (58) to the corresponding ω'-halo-α'-keto-α,α-dimethylphenylacetic acid compound of structure (46) are chromium (IV) oxide, silver (I) oxide, silver oxide, argentic picolinate, peroxide, nitric acid, m-chloroperbenzoic acid and peracetic acid.

In step 92, the aldehyde functionality of the appropriate cyclopropylketo-α,α-dimethylphenylacetaldehyde compound of structure (59) is oxidized to give the corresponding cyclopropylketo-α,α-dimethylphenylacetic acid compound of structure (47) as described previously in step $g_1$.

Starting materials for use in Scheme I are readily available to one of ordinary skill in the art.

The following examples present typical syntheses as described in Scheme I. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "$\mu$L" refers to microliters; "$\mu$g" refers to micrograms; and "$\mu$M" refers to micromolar.

EXAMPLE 37

Step $a_1$: 2-(4-(4-Chloro-1-oxo-butyl))-phenyl-2-methyl Propanyl Acetate

Mix 1-methyl-2-pyrrolidinone (400 mL, sodium acetate (205 g, 2.5 mol), stir at heat to 100° C. in a reaction flask which is fitted with a distillation head. Add, by dropwise addition, methylallyl chloride (181 g, 2.0 mol) over 1 hour. Heat the pot to 120° C. for 30 minutes collect methallyl acetate by distillation (193 g).

Mix methallyl acetate (228 g, 2.0 mol) and benzene (1 L) and cool to 5° C. Add aluminum chloride (266 g, 2.0 mol) over approximately 30 minutes while maintaining the temperature below 10° C. Add, in portions of 50 mL to 80 mL each, to a 5° C. mixture of aluminum chloride (15 g) in benzene (600 mL). After addition is complete, stir at 0–3° C. for ½ hour, pour onto ice (2kg) and separate the organic layer. Wash with water (2×300 mL), dry ($Na_2SO_4$), and distill to give neophyl acetate.

Dissolve neophyl acetate (150 g, 0.78 mol) in methylene chloride (390 mL) and cool to 5° C. Add anhydrous aluminum chloride (104 g, 0.78 mol) at such a rate that the temperature is maintained below 10° C. Cool the reaction mixture to 5° C. Dissolve anhydrous aluminum chloride (122 g) in methylene chloride (390 mL) and cool to 5° C. Add 4-chlorobutyryl chloride (132 g, 0.94 mol) at such a rate that the temperature is kept below 10° C. Cool the reaction to 5° C. and add the neophyl acetate-aluminum chloride solution in one portion and stir between −5° C. and 5° C. for 19 hours. Pour slowly over crushed ice (1.5 kg), separate the organic phase and wash with water (3×300 mL), cold aqueous potassium carbonate (10%, 300 mL) and water (300 mL). Evaporate the solvent in vacuo and filter to give the title compound as a light-brown oil (221.1 g, 95.6%).

$^1$H NMR (300 MHz, $CDCl_3$) δ1.34 (6H, s), 1.95 (3H, s), 2.18 (2H, quent.), 3.13 (2H, t), 3.65 (2H, t), 4.12 (2H, s), 7.43, 7.90 (2H each, d).

EXAMPLE 38

Step $b_1$: 2-(4-(1-Oxo-1-cyclopropanyl)-phenyl-2-methylpropanyl Acetate

Mix 2-(4-(4-chloro-1-oxo-butyl))-phenyl-2-methyl propanyl acetate (37.0 g, 0.125 mol), tetrabutylammonium hydroxide (8.1 g of a 40% aqueous solution), methylene chloride (300 mL) and 50% sodium hydroxide (40 mL). Stir vigorously at room temperature for 4 hours, add water (100 mL) and separate the organic layer. Wash with water (2×100 mL), dry ($MgSO_4$) and evaporate the solvent in vacuo to give the title compound (29.99).

$^1$H NMR (300 MHz, $CDCl_3$) δ1.00, 1.19 (2H each, m), 1.34 (6H, s), 1.95 (3H, s), 2.65 (1H, m), 4.13 (2H, s), 7.44, 7.95 (2H each, d).

EXAMPLE 39

Step $C_1$: 2-(4-(4-Chloro-1-oxobutyl)-phenyl-2-methylpropanol

Mix 2-(4-(4-chloro-1-oxo-butyl))-phenyl-2-methyl propanyl acetate, concentrated hydrochloric acid (555 mL), and ethanol (2.5 L) and reflux for 2.5 hours under a nitrogen atmosphere. Evaporate the solvent in vacuo and take the residue up in methylene chloride (1 L). Wash sequentially with water (2×400 mL), aqueous potassium carbonate (10%, 200 mL) and water (300 mL). Evaporate the solvent in vacuo to give the title compound as a light-brown oil (200 g, 90%).

$^1$H NMR (300 MHz, $CDCl_3$) δ1.35 (6H, s), 2.21 (2H, quent.) 3.15, (2H, t), 3.64 (2H, s), 3.66 (2H, 5), 7.48, 7.93 (2H each, d).

EXAMPLE 40

Step $c_2$: 2-(4-(1-Oxo-1-cyclopropanyl))-phenyl-2-methylpropanol

Mix 2-(4-(4-chloro-1-oxobutyl)-phenyl-2-methylpropanol (101 g, 0.34 mol), methylene chloride (800 mL), 40% aqueous solution of tetrabutylammonium hydroxide (33 g), and 50% aqueous solution of sodium hydroxide (162 mL) and reflux for 48 hours. Add water (300 mL), separate the organic phase and wash with water (2×300 mL). Dry ($MgSO_4$) and evaporate the solvent in vacuo to give the title compound as a light-brown oil (71.1 g, 96%).

EXAMPLE 41

Step $c_3$: 2-(4-(1-Oxo-1-cyclopropanyl))-phenyl-2-methylpropanol

Mix 2-(4-(1-oxo-1-cyclopropanyl))-phenyl-2-methylpropanyl acetate (4.16 g, 14 mmol), ethanol (50 mL) and water (5 mL). Add 50% aqeuous sodium hydroxide (4.48 mL, 56 mmol). Stir and heat at reflux for 30 minutes then remove the ethanol in vacuo. Extract the aqueous residue with methylene chloride (2×25 mL), wash with water (2×25 mL), dry ($MgSO_4$) and evaporate the solvent in vacuo to give the title compound as a brown oil (2.91 g, 95.3%).

$^1$H NMR (300 MHz, $CDCl_3$) δ1.03, 1.20 (2H each, m), 1.35 (6H, s), 1.70 (1H, t, br), 2.66 (1H, m), 3.64 (2H, d), 7.48, 7.98 (2H each, d).

EXAMPLE 42

Step $d_2$: 2-(4-(4-Chloro-2-oxo-butyl))-phenyl-2-methylpropionic Acid

Mix powdered potassium permanganate (39.5 g, 0.25 mol), water (34 mL) and acetic acid (200 mL). Stir and cool at 0° C., then add 85% phosphoric acid (4.2 g). Stir vigorously and add 2-(4-(4-chloro-1-oxo-butyl))-phenyl-2-methylpropanol (24.5 g, 0.1 mol) in acetic acid (50 mL) at such a rate as to keep the temperature below 5° C. Stir for 5.5 hours below 5° C., add ice water (300 mL), then sodium metabisulfite (45 g) in small portions until the dark brown mixture becomes colorless. Extract the aqueous solution with methylene chloride (3×150 mL), wash with water (100 mL) then extract with 20% aqueous potassium carbonate (2×150 mL). Wash the ageuous phase with methylene chloride (50 mL), cool in an ice-bath and acidify carefully with concentrated hydrochloric acid until pH 3. Extract with methylene chloride (2×150 mL), wash wih water (2×80 mL) and dry ($MgSO_4$). Evaporate the solvent in vacuo to give the title compound as a crystalline solid (21.259).

$^1$H NMR (300 MHz, $CDCl_3$) δ1.63 (6H, s), 2.22 (2H, quent.), 3.17 (2H, t), 3.67 (2H, t), 7.50, 7.92 (2H each, d), 12.3 (1H, s, br).

EXAMPLE 43

Step d₅: 2-(4-(1-oxo-1-cyclopropanyl))-phenyl-2-methylpropionic Acid

Method A

Mix 2-(4-(1-oxo-1-cyclopropanyl))-phenyl-2-methylpropanol (1.46 g, 6.7 mmol), ruthenium chloride (0.036 g, 0.17 mmol), acetonitrile (14 mL), carbon tetrachloride (14 mL) and water (20 mL). Stir vigorously and add sodium periodate (5.85 g) in one portion. Stir at room temperature for one hour longer, partition between methylene chloride (20 mL) and water (5 mL), s separate the organic layer, extract the aqeuous layer with methylene chloride (15 mL) and wash the combined methylene chloride layers with water (15 mL) and extract with 20% aqueous potassium carbonate (2×25 mL). Cool the base solution in an ice-bath, acidify carefully with concentrated hydrochloride acid to pH 3 and extract into methylene chloride (2×30 mL). Wash with water (15 mL), dry (MgSO₄) and evaporate the solvent in vacuo to give the title compound as a yellow oil (1.41 g, 90%).

$^1$H NMR (300 MHz, CDCl₃) δ1.04, 1.23 (2H each, d), 1.63 (6H, s), 2.65 (1H, m), 7.50, 7.99 (2H each, d).

Method B

Mix 2-(4-(1-oxo-1-cyclopropanyl))-phenyl-2-methylpropanol (10.9 g, 50 mmol), ruthenium chloride (0.032 g, 0.16 mmol), acetic acid (100 ml) and water (25 mL). Cool to 10° C. and add, by dropwise addition, an aqueous solution of sodium hypochloride (70 ml), stirring vigorously over a 30-minute period. Stir below 10° C. for 30 minutes longer, evaporate most of the solvent in vacuo and take the residue up in methylene chloride (120 mL). Wash the methylene chloride solution with water (2×40 mL) and extract with 20% aqueous potassium carbonate (2×50 mL). Cool the base solution in an ice-bath, acidify carefully with concentrated hydrochloride acid to ph 3 and extract into methylene chloride (2×50 mL). Wash the organic layer with water (40 mL), dry (MgSO₄) and evaporate the solvent in vacuo to give the title compound as a light-yellow oil (5.46 g, 47%).

Method C

Mix potassium permanganate (3.61 g, 22.8 mmol), water (2 mL) and acetic acid (10 mL). Stir and cool to 10° C. and add 85% phosphoric acid (500 mg). Add, by dropwise addition, a solution 2-(4-(1-oxo-1-cyclopropanyl))-phenyl-2-methylpropanol (1.66 g, 7.6 mmol) in acetic acid (5 mL) over 5 minutes. Stir below 10° C. for 1 hour and then at room temperature for 5 hours. Add water (20 mL) followed by addition of Na₂S₂O₅ in small portions until the solution becomes colorless. Extract with methylene chloride (2×50 mL), wash the methylene chloride solution with water (30 mL) and then extract with 10% aqueous potassium carbonate (2×50 mL). Cool the base solution in an ice-bath, acidify carefully with concentracted hydrochloric acid to pH 3 and extract with methylene chloride (2×50 mL). Wash the organic layer with water (20 mL), dry (MgSO₄) and evaporate the solvent in vacuo to give the title compound as a colorless needles (1.20 g, 68%).

$^1$H NMR (300 MHz, CDCl₃) δ1.00 (4H, d), 1.50 (6H, s), 7.49, 8.00 (2H each, d), 12.6 (1H, s, br).

Method D

Mix 2-(4-(1-oxo-1-cyclopropanyl))-phenyl-2-methylpropanol (2.30 g, 10.6 mmol), acetic acid (5.5 mL) and fuming nitric acid (6.5 mL). Stir and heat at 48–50° C. for 2 hours, cool and add ice water (20 mL) followed by methylene chloride (60 mL). Separate the organic layer, wash with water (2×20 mL) and extract into 10% aqueous potassium carbonate (2×40 mL). Wash the alkaline solution with methylene chloride (10 mL) and cool in an ice-bath. Acidify carefully with concentrated hydrochloric acid to ph 3, extract with methylene chloride (2×40 mL), wash the combined organic layers with water (20 mL), dry (MgSO₄) and evaporate the solvent in vacuo to give the title compound as light-yellow needles (1.89 g, 77%).

Method E

Mix 2-(4-(1-oxo-1-cyclopropanyl))-phenyl-2-methylpropanol (2.26 g, 10.4 mmol), sodium nitrite (60 mg), acetic acid (5 mL) and concentrated nitric acid (6 mL, d=1.42, 70%, 94 mmol). Stir and heat at 48–50° C. for 2 hours, cool and dilute with ice water (20 mL). Extract into methylene chloride (2×30 mL), wash the combined organic layers with water (2×20 mL) and extract into 10% aqeuous potassium carbonate (2×40 mL). Wash the alkaline solution with methylene chloride (10 mL) and cool in an ice-bath. Acidify carefully with concentrated hydrochloric acid to pH 3 and extract into methylene chloride (2×40 mL). Wash the combined organic layers with water (20 mL), dry (MgSO₄) and evaporate the solvent in vacuo to give the title compound as light yellow needels (2.01 g, 83%).

EXAMPLE 44

Step d₆: 2-(4-(1-Oxo-1-cyclopropanyl))-phenyl-2-methylpropionic Acid

Mix 2-(4-(1-oxo-1-cyclopropanyl))-phenyl-2-methylpropanyl acetate (5.0 g, 0.0197 mol), sodium nitrite (100 mg), acetic acid (10 mL) and concentrated nitric acid (8.7 mL, d=1.42, 70%, 0.137 mol). Stir and heat at 48–50° C. for 5.5 hours, cool and dilute with ice water (40 mL). Extract into methylene chloride (2×70 mL), wash the combined methylene chloride extracts with water (2×50 mL) and reduce the volue to 50 mL in vacuo. Extract with 10% aqueous potassium carbonate (2×50 mL), was the base solution with methylene chloride (20 mL) and cool in an ice-bath. Acidify carefully with concentrated hydrochloric acid to pH 3 and extract into methylene chloride (2×60 mL). Wash the combined methylene chloride extracts with water (30ml), dry (MgSO₄) and evaporate the solvent in vacuo to give the title compound asa crystalline solid (4.12 g, 90%).

The novel intermediates of formula (X) wherein R₅ is H, Br, Cl, I, CN, —COOH, —COOalkyl or —CONR₆R₇ may be prepared as described in Scheme J. In Scheme J, all substituents are as previously defined unless otherwise indicated.

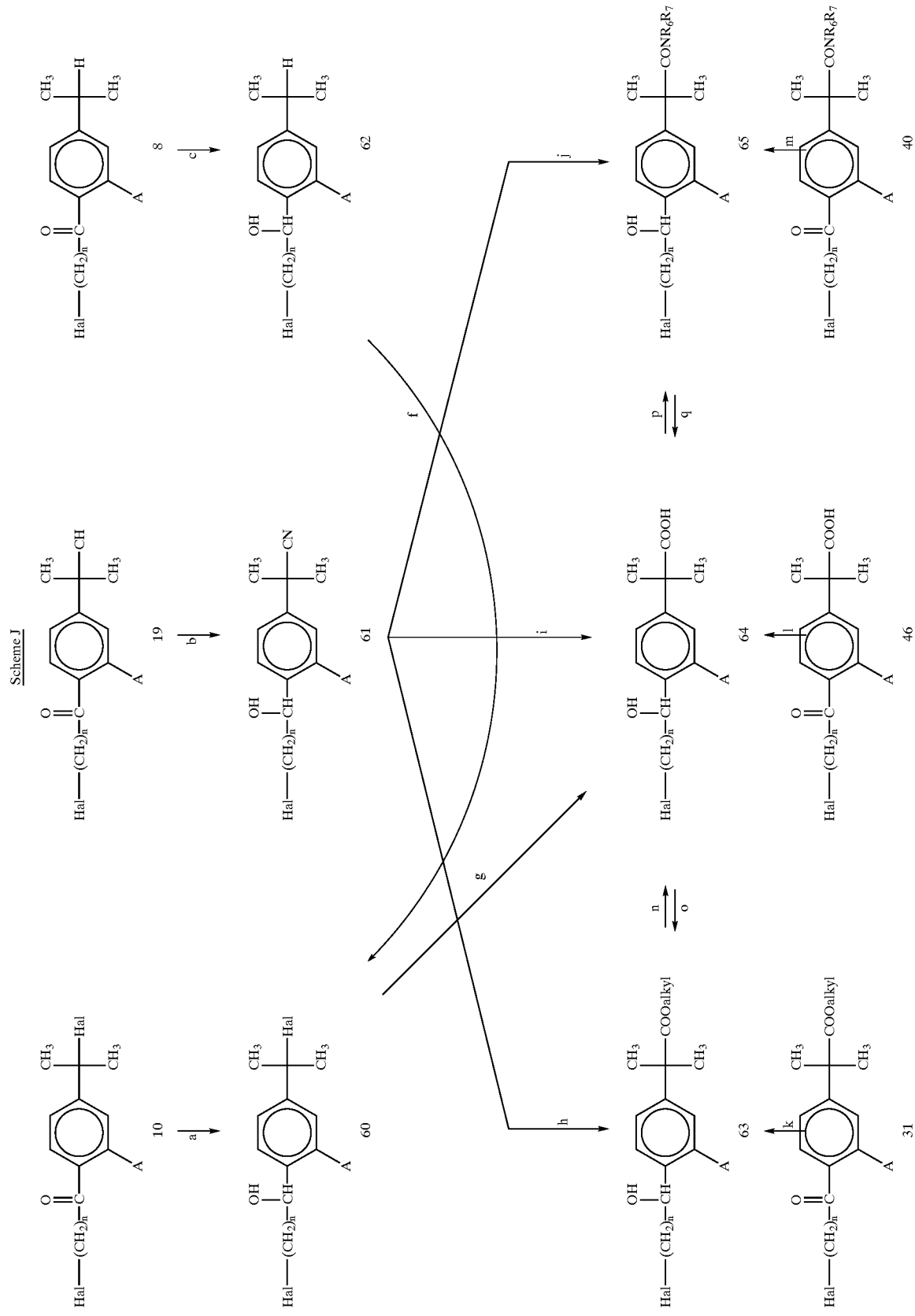

Scheme J provides various general synthetic procedures for preparing the novel intermediates of formula (X) wherein $R_5$ is H, Br, Cl, I, CN, —COOH, —COOalkyl or —CONR$_6$R$_7$.

In step a, the ketone functionality of the appropriate ω-halo-halocumylketone compound of structure (10) is reduced to give the corresponding ω-halo-halocumylalcohol compound of structure (60).

For example, reduction of the appropriate ω-halo-halocumylketone compound of structure (10), using, for example, a suitable reducing agent such as sodium borohydride, potassium borohydride, sodium cyanoborohydride, or tetramethylammonium borohydride is carried out in lower alcohol solvents, such as, methanol, ethanol, isopropyl alcohol or n-butanol at temperatures ranging from about 0° C. to the reflux temperature of the solvent, and the reaction time varies from about ½ hour to 8 hours. Other suitable reducing agents are, for example, lithium tri-tert-butylaluminohydride and diisobutylaluminum hydride. These reduction reactions are carried out in suitable solvents diethyl ether, tetrahydrofuran or dioxane at temperatures ranging from about 0° C. to the reflux temperature of the solvent, and the reaction time varies from about ½ hour to 8 hours.

Catalytic reduction may also be employed in the preparation of appropriate ω-halo-halocumylalcohol compound of structure (60) from an appropriate ω-halo-halocumylketone compound of structure (10), using hydrogen gas in the presence of a suitable catalyst such as Raney nickel, palladium, platinum or rhodium catalysts in lower alcohol solvents, such as, methanol, ethanol, isopropyl alcohol or n-butanol or acetic acid or their aqueous mixtures, or by the use of aluminum isopropoxide in isopropyl alcohol.

In addition, a chiral reduction of the appropriate ω-halo-halocumylketone compound of structure (10), using, for example, (+)-B-chlorodiisopinocamphenylborane gives the corresponding (R)-ω-halo-halocumylalcohol compound of structure (60) and (−)-B-chlorodiisopinocamphenylborane gives the corresponding (S)-ω-halo-halocumylalcohol compound of structure (60). Other suitable chiral reducing agents are, (R) and (S)-oxazaborolidine/BH$_3$, potassium 9-O-(1,2:5,6-di-O-isopropylidine-α-D-glucofuransoyl)-9-boratabicyclo[3.3.1]nonane, (R) and (S)-B-3-pinanyl-9-borabicyclo[3.3.1]nonane, NB-Enantride, Lithium (R)-(+) and (S)-(−)-2,2'-dihydroxy-1,1'-binaphthyl alkoxyl aluminum hydride, (R)-(+) and (S)-(−)-2,2'-dihydroxy-6,6'-dimethylbiphenyl borane-amine complex, tris[[(1S,2S,5R)-2-isopropyl-5-methyl-cyclohex-1-yl]methyl]aluminum, [[(1R,3R)-2,2-dimethylbicyclo[2.2.1]hept-3-yl]methyl]beryllium chloride, (R)-BINAP-ruthenium complex/H$_2$ and 6,6'-bis-(diphenylphosphino)-3,3'-dimethoxy-2,2',4,4'-tetramethyl-1,1'-biphenyl.

In step b, the ketone functionality of the appropriate ω-halo-cyanocumylketone compound of structure (19) is reduced to give the corresponding ω-halo-cyanocumylalcohol compound of structure (61) as described previously in step a.

In step c, the ketone functionality of the appropriate ω-halo-cyanocumylketone compound of structure (8) is reduced to give the corresponding ω-halo-cyanocumylalcohol compound of structure (62) as described previously in step a.

In step d, the α-halo functionality of the appropriate ω-halo-halocumylalcohol compound of structure (60) is cyanated to give the corresponding ω-halo-cyanocumylalcohol compound of structure (61) as described previously in Scheme D, step a.

In step e, the appropriate ω-halo-cyanocumylalcohol compound of structure (62) is cyanated to give the corresponding ω-halo-cyanocumylalcohol compound of structure (61) as described previously in Scheme D, step b.

In step f, the appropriate appropriate ω-halo-cyanocumylalcohol compound of structure (62) is halogenated to give the corresponding ω-halo-halocumylalcohol compound of structure (60) as described previously in Scheme B, step a.

In step g, the α-halo functionality of the appropriate ω-halo-halocumylalcohol compound of structure (60) is converted to the corresponding carboxy to give the ω'-halo-α'-hydroxy-α,α-dimethylphenylacetic acid compound of structure (64) as described previously in Scheme H, step h.

In step h, the nitrile functionality of the appropriate ω-halo-cyanocumylalcohol compound of structure (61) is converted to the corresponding ester to give the ω'-halo-α'-hydroxy-α,α-dimethylphenylacetic acid ester compound of structure (63) as described previously in Scheme H, step a.

In step i, the nitrile functionality of the appropriate ω-halo-cyanocumylalcohol compound of structure (61) is converted to the corresponding acid to give the ω'-halo-α'-hydroxy-α,α-dimethylphenylacetic acid compound of structure (64) as described previously in Scheme H, step e.

In step j, the nitrile functionality of the appropriate ω-halo-cyanocumylalcohol compound of structure (61) is converted to the corresponding amide to give the ω'-halo-α'-hydroxy-α,α-dimethylphenylacetic acid amide compound of structure (65) wherein R$_6$ and R$_7$ are each hydrogen as described previously in Scheme H, step b.

In step k, the ketone functionality of the appropriate ω'-halo-α'-keto-α,α-dimethylphenylacetic acid ester compound of structure (31) is reduced to give the corresponding ω'-halo-α'-hydroxy-α,α-dimethylphenylacetic acid ester compound of structure (63) as described previously in step a.

In step 1, the ketone functionality of the appropriate ω'-halo-α'-keto-α,α-dimethylphenylacetic acid compound of structure (46) is reduced to give the corresponding ω'-halo-α'-hydroxy-α,α-dimethylphenylacetic acid compound of structure (64) as described previously in step a.

In step m, the ketone functionality of the appropriate ω'-halo-α'-keto-α,α-dimethylphenylacetic acid amide compound of structure (40) is reduced to give the corresponding ω'-halo-α'-hydroxy-α,α-dimethylphenylacetic acid amide compound of structure (65) as described previously in step a.

In step n, the carboxy ester functionality of the appropriate ω'-halo-α'-hydroxy-α,α-dimethylphenylacetic acid ester compound of structure (63) is hydrolyzed to give the corresponding ω'-halo-α'-hydroxy-α,α-dimethylphenylacetic acid compound of structure (64) as described previously in Scheme H, step c.

In step o, the carboxy functionality of the appropriate ω'-halo-α'-hydroxy-α,α-dimethylphenylacetic acid compound of structure (64) may be esterified by techniques and procedures well known and appreciated by one of ordinary skill in the art to give the corresponding ω'-halo-α'-hydroxy-α,α-dimethylphenylacetic acid ester compound of structure (63) as described previously in Scheme H, step d.

In step p, the carboxy functionality of the appropriate ω'-halo-α'-hydroxy-α,α-dimethylphenylacetic acid compound of structure (65) may be amidated by techniques and procedures well known and appreciated by one of ordinary skill in the art to give the corresponding ω'-halo-α'-hydroxy-α,α-dimethylphenylacetic acid amide compound of structure (57) as described previously in Scheme H, step g.

In step q, the amide functionality of the appropriate ω'-halo-α'-hydroxy-α,α-dimethylphenylacetic acid amide compound of structure (65) is converted to the corresponding acid by acid hydrolysis as is known in the art to give the ω'-halo-α'-hydroxy-α,α-dimethylphenylacetic acid compound of structure (64) as described previously in Scheme H, step f.

In addition, the novel intermediates of formula (X) wherein $R_5$ is —$CH_2OD$ may be prepared as described in Scheme K. In Scheme K, all substituents are as previously defined unless otherwise indicated.

Scheme K

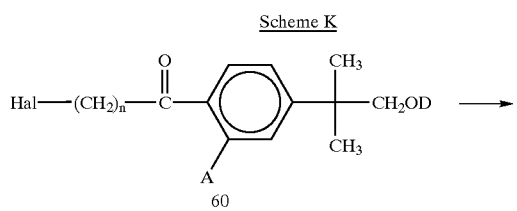

60

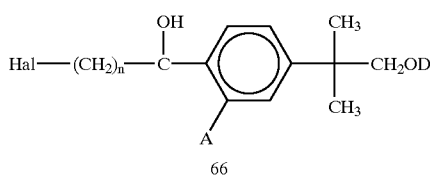

66

$D = H, \quad —C(=O)CH_3, \quad —C(=O)C_6H_5,$

In Scheme K, the ketone functionality of the appropriate ω'-halo-α'-keto-(2-methylpropanol)benzene compound of structure (60) is reduced to give the corresponding ω'-halo-α'-hydroxy-(2-methylpropanol)benzene compound of structure (66) as described previously in Scheme J, step a.

The novel intermediates of formula (XI) wherein $R_5$ is hydrogen, CN, COOalkyl or $CONR_6R_7$ may be prepared as described in Scheme L. In Scheme L, all substituents are as previously defined unless otherwise indicated.

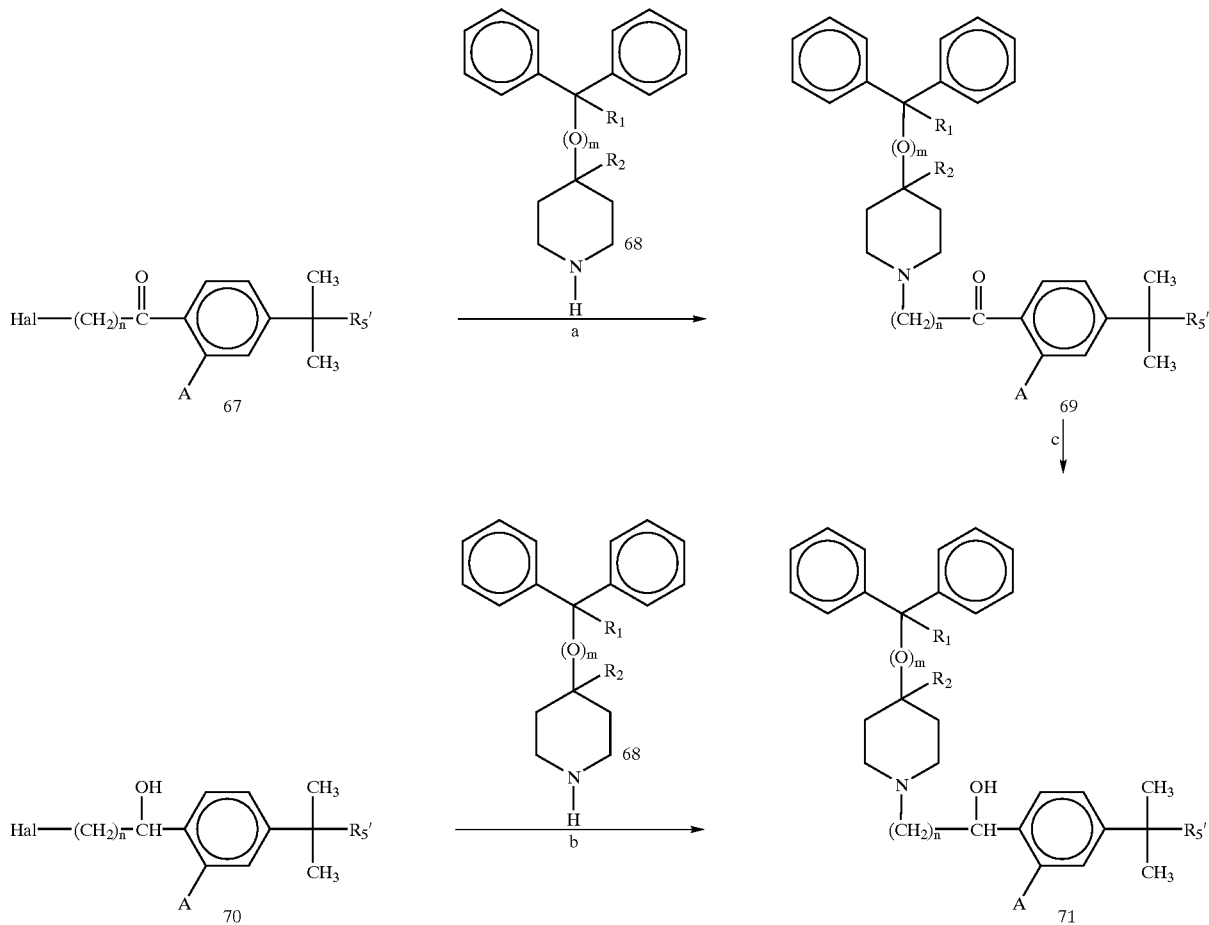

$R_5'$ is H, CN, COOalkyl or $CONR_6R_7$

Scheme L provides various general synthetic procedures for preparing the novel intermediates of formula (XI) wherein $R_5$ is hydrogen, CN, COOalkyl or $CONR_6R_7$.

In step a, the ω'-halo functionality of the appropriate ω'-halo-α'-keto-α,α-dimethylphenyl compound of structure (67) wherein $R_5$ is hydrogen, CN, COOalkyl or $CONR_6R_7$ is alkylated with the appropriate piperidine compound of structure (68) to give the corresponding ω'-piperidine-α'-keto-α,α-dimethylphenyl compound of structure (69) wherein $R_5$ is hydrogen, CN, COOalkyl or $CONR_6R_7$.

For example, the ω'-piperidine-α'-keto-α,α-dimethylphenyl compound of structure (69) wherein $R_5$ is hydrogen, CN, COOalkyl or $CONR_6R_7$ may be prepared by reacting the appropriate ω'-halo-α'-keto-α,α-dimethylphenyl compound of structure (67) wherein $R_5$ is hydrogen, CN, COOalkyl or $CONR_6R_7$ with the appropriate piperidine compound of structure (68) in a suitable solvent preferably in the present of a suitable non-nucleophilic base and optionally in the presence of a catalytic amount of an iodide source, such as potassium or sodium iodide. The reaction time varies from about 4 to 120 hours and the reaction temperature varies from about 70° C. to the reflux temperature of the solvent. Suitable solvent for the alkylation reaction include alcohol solvents such as, methanol, ethanol, isopropyl alcohol, or n-butanol; ketone solvents, such as, cyclohexanone, methyl isobutyl ketone; hydrocarbon solvents, such as, benzene, toluene or xylene; halogenated hydrocarbons, such as, chlorobenzene or methylene chloride or dimethylformamide. Suitable non-nucleophilic bases for the alkylation reaction include inorganic bases, for example, sodium bicarbonate, potassium carbonate, or potassium bicarbonate or organic bases, such as, a trialkylamine, for example, triethylamine or pyridine, or an excess of an appropriate piperidine compound of structure (68) may be used.

For those piperidine compounds of structure (68), wherein $R_1$ is hydroxy, it is preferred that $R_1$ be unprotected for utilization in the alkyation reaction of step a, but those hydroxy functionalities present in the piperidine compounds of structure (68), wherein $R_1$ is hydroxy may be protected with a suitable protecting group. The selection and utilization of suitable protecting groups for the piperidine compounds of structure (68), wherein $R_1$ is hydroxy is well known by one of ordinary skill in the art and is described in "Protective Groups in Organic Syntheses", Theodora W. Greene, Wiley (1981). For example, suitable protecting groups for those hydroxy functionalities present include ethers such as tetrahydrothiopyranyl, tetrahydrothiofuranyl, 2-(phenylselenyl)ethyl ether, o-nitrobenzyl ether, trimethylsilyl ether, isopropyldimethylsilyl ether, t-butyldimethylsilyl ether, t-butyldiphenylsilyl ether, tribenzylsilyl ether, triisopropylsilyl ether; and esters, such as acetate ester, isobutyrate ester, pivaloate ester, adamantoate ester, benzoate ester, 2,4,6-trimethylbenzoate (mesitoate) ester, methyl carbonate, p-nitrophenyl carbonate, p-nitrobenzyl carbonate, S-benzyl thiocarbonate and N-phenylcarbamate.

The piperidine compounds of structure (68) are readily available to one of ordinary skill in the art and are described in U.S. Pat. No. 4,254,129, Mar. 3, 1981, U.S. Pat. No. 4,254,130, Mar. 3, 1981, U.S. Pat. No. 4,285,958, Apr. 25, 1981 and U.S. Pat. No. 4,550,116, Oct. 29, 1985. The piperidine compounds of structure (68) wherein $R_1$ and $R_2$ form a second bond between the carbon atoms bearing $R_1$ and $R_2$ may be prepared by dehydration of the corresponding compound wherein $R_1$ is hydroxy by procedures generally known in the art, such as refluxing in strongly acidic solution.

The piperidine compounds of structure (68) include the limitations provided for previously for piperidine derivatives of formula (I) and (XI) in that when $R_1$ and $R_2$ are taken together to form a second bond between the carbon atoms bearing $R_1$ and $R_2$ or where $R_1$ represented hydroxy, m is an integer 0.

In step b, the ω'-halo functionality of the appropriate ω-halo-α'-hydroxy-α,α-dimethylphenyl compound of structure (70) wherein $R_5$ is hydrogen, CN, COOalkyl or $CONR_6R_7$ is alkylated with the appropriate piperidine compound of structure (68) to give the corresponding ω'-piperidine- α'-hydroxy-α,α-dimethylphenyl compound of structure (71) wherein $R_5$ is hydrogen, CN, COOalkyl or $CONR_6R_7$ as described previously in step a.

In step c, the ketone functionality of the appropriate ω'-piperidine-α'-keto-α,α-dimethylphenyl compound of structure (69) wherein $R_5$ is hydrogen, CN, COOalkyl or $CONR_6R_7$ is reduced to give the corresponding ω'-piperidine-α'-hydroxy-α,α-dimethylphenyl compound of structure (71) wherein $R_5$ is hydrogen, CN, COOalkyl or $CONR_6R_7$.

For example, reduction of the appropriate ω'-piperidine-α'-keto-α,α-dimethylphenyl compound of structure (69) wherein $R_5$ is hydrogen, CN, COOalkyl or $CONR_6R_7$, using, for example, a suitable reducing agent such as sodium borohydride, potassium borohydride, sodium cyanoborohydride, or tetramethylammonium borohydride is carried out in lower alcohol solvents, such as, methanol, ethanol, isopropyl alcohol or n-butanol at temperatures ranging from about 0° C. to the reflux temperature of the solvent, and the reaction time varies from about ½ hour to 8 hours. Other suitable reducing agents are, for example, lithium tri-tert-butylaluminohydride and diisobutylaluminum hydride. These reduction reactions are carried out in suitable solvents diethyl ether, tetrahydrofuran or dioxane at temperatures ranging from about 0° C. to the reflux temperature of the solvent, and the reaction time varies from about ½ hour to 8 hours.

Catalytic reduction may also be employed in the preparation of appropriate ω'-piperidine-α'-hydroxy-α,α-dimethylphenyl compound of structure (71) wherein $R_5$ is hydrogen, CN, COOalkyl or $CONR_6R_7$ from an appropriate ω'-piperidine-α'-keto-α,α-dimethylphenyl compound of structure (69) wherein $R_5$ is hydrogen, CN, COOalkyl or $CONR_6R_7$, using hydrogen gas in the presence of a suitable catalyst such as Raney nickel, palladium, platinum or rhodium catalysts in lower alcohol solvents, such as, methanol, ethanol, isopropyl alcohol or n-butanol or acetic acid or their aqueous mixtures, or by the use of aluminum isopropoxide in isopropyl alcohol.

Reduction using sodium borohydride or potassium borohydride is preferred over catalytic reduction for those ω'-piperidine-α'-keto-α,α-dimethylphenyl compound of structure (69) wherein $R_5$ is hydrogen, CN, COOalkyl or $CONR_6R_7$ and wherein $R_1$ and $R_2$ taken together form a second bond between the carbon atoms bearing $R_1$ and $R_2$.

In addition, a chiral reduction of the appropriate ω'-piperidine-α'-keto-α,α-dimethylphenyl compound of structure (69) wherein $R_5$ is hydrogen, CN, COOalkyl or $CONR_6R_7$, using, for example, (+)-B-chlorodiisopinocamphenylborane gives the corresponding (R)-ω'-piperidine-α'-keto-α,α-dimethylphenyl compound of structure (69) wherein $R_5$ is hydrogen, CN, COOalkyl or $CONR_6R_7$ and (−)-B-chlorodiisopinocamphenylborane gives the corresponding (S)-ω'-piperidine-α'-keto-α,α-dimethylphenyl compound of structure (69) wherein $R_5$ is hydrogen, CN, COOalkyl or $CONR_6R_7$. Other suitable chiral reducing agents are, (R) and (S)-oxazaborolidine/$BH_3$, potassium 9-O-(1,2:5,6-di-O-isopropylidine-α-D-glucofuransoyl)-9-boratabicyclo[3.3.1] nonane, (R) and (S)-B-3-pinanyl-9-borabicyclo[3.3.1]

nonane, NB-Enantride, Lithium (R)-(+) and (S)-(–)-2,2'-dihydroxy-1,1'-binaphthyl alkoxyl aluminum hydride, (R)-(+) and (S)-(–)-2,2'-dihydroxy-6,6'-dimethylbiphenyl borane-amine complex, tris[[(1S,2S,5R)-2-isopropyl-5-methyl-cyclohex-1-yl]methyl]aluminum, [[(1R,3R)-2,2-dimethylbicyclo[2.2.1]hept-3-yl]methyl]beryllium chloride, (R)-BINAP-ruthenium complex/$H_2$ and 6,6'-bis(diphenylphosphino)-3,3'-dimethoxy-2,2',4,4'-tetramethyl-1,1'-biphenyl.

Starting materials for use in Scheme L are readily available to one of ordinary skill in the art.

The following examples present typical syntheses as described in Scheme K. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "µL" refers to microliters; "µg" refers to micrograms; and "µM" refers to micromolar.

EXAMPLE 45

Step a: 4-[4-[4-(Hydroxydiphenylmethyl)-1-piperidinyl]-1-oxobutyl]-α,α-dimethylbenzeneacetic Acid Methyl Ester Mix methyl 4'-(4-chloro-1-oxobutyl)-α,α-dimethylbenzene acetate (0.335 mol), α,α-diphenyl-4-piperidinemethanol (101.8 g, 0.335 mol), potassium hydrogen carbonate (83.8 g, 0.838 mol), potassium iodide (1.00 g, 0.006 mol), toluene (600 mL) and water (220 mL). Stir at reflux for 72 hours, add toluene (200 mL) and deionized water (100 mL). Filter through filter aid while at 80° C. and separate the organic phase. Dry ($MgSO_4$), filter and purify by chromatography to give the title compound.

EXAMPLE 46

Step a: 4-[4-[4-(Hydroxydiphenylmethyl)-1-piperidinyl]-1oxobutyl]-α,α-dimethylbenzeneacetic Acid Ethyl Ester Method A: Remove the still head from the reaction flask containing a solution of ethyl 4'-(4-chloro-1-oxobutyl)-α,α-dimethylbenzene acetate and xylenes obtained from Example 11, Method G and reattach a reflux condenser. At ambient temperature, add azacyclonol free base which has been recrystallized from toluene (178.28 g, 0.660 mol) and stir at 175 RPM while heating by heating mantle. After the temperature of the reaction slurry reaches 137 (approximately 30 minutes), stir the reaction for 5.5 hours, maintaining the temperature betwwen 137–144° C. Remove the heating mantle, add mixed xylenes (100 mL) and allow the reaction slurry to cool to 64° C. Increase the stirring rate to 300 RPM and add glacial acetic acid (15.17 g, 0.253 mol). Maintain the temperature at 64–69° C. for 1.9 hours by heating with mantle, cool from 64–60° C. over a period of 15 minutes; and from 60–50° C. over a period of 32 minutes; from 50–42° C. over a period of 33 minutes. Filter at 42° C. by suction through a 350 mL coarse sintered glass filter funnel and wash the filtercake with mixed xylenes (200 mL) at ambient temperature. Allow the filtrate to stand at ambient temperature overnight then place in a 1 L flask. Add isopropanol (40 mL) and attached an overhead paddle stirrer. With stirring at 150 RPM, slowly add 37% aqeuous concentrated HCl at ambient temperature, adding 2.00 g during the first 17 minutes, adding a total of 33.13 g of HCl over 245 minutes. After the slurry has been digested, collect the solids by suction filtration through a 350 mL coarse sintered glass funnel and wash the filtercake with fresh xylenes (200 mL) and then with n-heptane (100 mL). Dry the filtercake under vacuum at 47° C. for 2.5 days to give the title compound as an off-white solid (141.17 g, 81%).

Concentrate the filtrate by rotary evaporator to give a thick residue of solids and syrup (23.78 g). Add acetone (68 g) and agitate by swirling until the syrup dissolves or releases as a solid. Collect the solids by suction filtration through a medium sintered glass funnel, wash with fresh acetone (17 g) and dry under vacuum to give the title compound as a light tan solid (3.75 g).

Method B: Place the solution of ethyl 4'-(4-chloro-1-oxobutyl)-α,α-dimethylbenzene acetate and xylenes obtained from Example 11, Method G in a 1 L, 3-neck round bottom flask and add azacyclonol free base recrystallied prom toluene (192.2 g, 0.719 mol). Stir the resulting slurry by overhead stirrer and heat to 140° C. for 5.5 hours. Allow to cool to ambient temperature and add a mixture of 4-[4-[4-(hydroxydiphenylmethyl)-1-piperidinyl)-1-oxobutyl]-α,α-dimethylbenzeneacetic acid ethyl ester hydrochloride (33.8 g, 0.0318 mol) and azacyclonol hydrochloride (0.0534 mol), slurried in mixed xylenes (100 mL). Reheat the resulting slurry to 135° C. with stirring and then allow to cool slowly to ambient temperature.

Vacuum filter and wash the filtercake with xylenes. Dry the filtercake under vacuum to give a solid (122.4 g). Concentrate the filtrate by rotary evaporator to a weight ot 486 g and add, by dropwise addition, 91 g (2.75 g, 0.0753 mol) of a solution of HCl gas (5.6 g) in absolute 2B ethanol (180 mL) at 70–80° C. over a 1.5 hour period. Cool slowly to 30° C. and filter by vacuum. Wash the filtercake with mixed xylenes and dry under vacuum at 50° C. to give the title compound as a solid (49.1 g).

To the filtrate from the second filtercake, add absolute 2B ethanol (100 mL), heat to 50° C. and sparge gaseous HCl (about 5 g) into the solution. Add additional mixed xylenes (170 mL) and absolute 2B ethanol (100 mL) and heat to 70 C. Sparge in additional HCl gas until the total HCl added is 10 g (0.274 mol). Cool to 50° C. and stir for 2 hours then cool to ambient temperature and stir overnight.

Distill a total of 240 mL of ethanol and xylenes from the slurry under reduced pressure (80 mm, with pot temperature from 50 to 70 C.). Cool to 30 C. over a 1 hour period and filter by vacuum. Wash the filtercake with toluene and dry under vacuum at 50 C. to give the title compound as a solid (119.2 g).

Method C: Place ethyl 4'-(4-chloro-1-oxobutyl)-α,α-dimethylbenzene acetate (15.00 g, 49.53 mmol), azacyclonol free base (29.66 g, 49.53 mmol) and mixed xylenes (60 mL) in a 250 mL 1-neck round bottom flask fitted with a magentic stir bar and reflux condenser. Beat the reaction mixture to reflux over a period of 15 minutes and then continue at reflux for 5.5 hours. Cool to ambient temperature and then to ice/water bath temperature. Separate the solids from the orange xylenes solution by suction filtration through a coarse sintered glass funnel, wash the filtercake with cold xylenes (25 mL) and dry in a vacuum oven at 60 C. to give the title compound as an off-white solid (16.21 g).

Method D: Place azacyclonol free base (35.00 g, 125.68 mmol), ethyl 4'-(4-chloro-1-oxobutyl)-α,α-dimethylbenzene acetate (17.30 g, 57.13 mmol) and mixed xylenes (60 mL) into a 250 mL round bottom flask. Heat to reflux by mantel in 13 minutes and stir by megnetic bar and heat at reflux for 6.3 hours. Remove the heat from the reaction flask and cool by ice/water bath. Filter the cold reaction slurry by suction through a coarse sintered glass funnel and wash the filtercake with fresh mixed xylenes (40 mL). Vacuum dry the filtercake at 40 C. overnight to give the title compound as a solid (17.87 g).

Add concentrated 37% HCl (2.18 g, 22.1 mmol) to the filtrate, stirred by magnetic bar. Stir overnight at ambient temperature, filter through suction through a coarse sintered glass funnel and wash the filtercake with fresh mixed xylenes (35 mL) Vacuum dry the filtercake at 50 C. to give the title compound as a solid (8.23 g).

Add concentrated 37% HCl (6.42 g, 65.2 mmol) to the filtrate stirred by magnetic bar. Add mixed xylenes (70 mL) and filter though a coarse sintered glass funnel, at ambient temperature. Wash the filtercake with fresh mixed xylenes (50 mL) and vacuum dry the filtercake to give the title compound as a solid (27.25 g).

Purify by recrystallization as follows: Mix the title compound (15 g), absolute 2B ethanol (45 mL) and n-heptane (90 mL) in a 500 mL round bottom flask with a magentic stir bar. Heat at reflux with stirring for 30 minutes, cool by ice/water bath and collect the solids by suction filtration through a coarse sintered glass funnel. Wash the filtercake with 3:1 n-heptane/ethanol (24 mL) and dry under vacuum at 55 C. to give the title compound as a white solid.

EXAMPLE 47

Step c: 4-[4-[4-(Hydroxydiphenylmethyl)-1-piperidinyl]-1-hydroxybutyl]-α,α-dimethylbenzeneacetic Acid Add sodium borohydride (0.105 g, 2.77 mmol) to a solution of sodium hydroxide (0.053 g, 1.33 mmol) in deionized water (2 mL) and add, by dropwise addition, to a solution of 4-[4-[4-(hydroxydiphenylmethyl)-1-piperidinyl]-1-oxobutyl]-α,α-dimethylbenzeneacetic acid hydrochloride (0.70 g, 1.31 mmol) in ethanol (30 mL). Stir at room temperature for 3.5 hours at pH 7–8. Evaporate the solvent in vacuo and stir the residue with methylene chloride (15 mL) and deionized water (15 mL). Dry ($MgSO_4$), acidify to pH 3 with gaseous hydrogen chloride and evaporate the solvent. Add ether with stirring, filter the white solid and wash with additional ether. Dry to give the title compound.

EXAMPLE 48

Step c: (R)-4-[4-[4-(Hydroxydiphenylmethyl)-1-piperidinyl]-1-hydroxybutyl]-α,α-dimethylbenzeneacetic, Ethyl Ester Dissolve (+)-B-chlorodiisopinocamphenylborane (2.5 g, 7.8 mmol) in anhydrous tetrahydrofuran (5 mL). Add a solution of 4-[4-[4-(hydroxydiphenylmethyl)-1-piperidinyl]-1-oxobutyl]-α,α-dimethylbenzeneacetic, ethyl ester (2 g, 3.54 mmol) in anhydrous tetrahydrofuran (5 mL). Stir at room temperature for 3 days and cool to 0° C. Add water (1 mL) and 30% hydrogen peroxide (2 mL) and stir for 20 minutes. Add methylene chloride (30 mL) and wash with brine 430 mL), then aqueous sodium hydrogen carbonate (30 mL), then brine (30 mL). Dry ($MgSO_4$), evaporate the solvent in vacuo and purify by chromatography to give the title compound.

EXAMPLE 49

Step c: (S)-4-[4-[4-(Hydroxydiphenylmethyl)-1-piperidinyl]-1-hydroxybutyl]-α,α-dimethylbenzeneacetic Acid, Ethyl Ester Dissolve (−)-B-chlorodiisopinocamphenylborane (2.5 g, 7.8 mmol) in anhydrous tetrahydrofuran (5 mL). Add a solution of 4-[4-[4-(hydroxydiphenylmethyl)-1-piperidinyl]-1-oxobutyl]-α,α-dimethylbenzeneacetic acid, methyl ester (3.54 mmol) in anhydrous tetrahydrofuran (5 mL). Stir at room temperature for 3 days and cool to 0° C. Add water (1 mL) and 30% hydrogen peroxide (2 mL) and stir for 20 minutes. Add methylene chloride (30 mL) and wash with brine (30 mL), then aqueous sodium hydrogen carbonate (30 mL), then brine (30 mL). Dry ($MgSO_4$), evaporate the solvent in vacuo and purify by chromatography to give the title compound.

EXAMPLE 50

Step a: N,N-Dimethyl-2-(4-{4-[4-hydroxy-diphenylmethyl)-piperidin-1-yl]-butyryl}-phenyl)-isobutyramide Dissolve N,N-dimethyl-2-[4-(4-chlorobutyryl)-phenyl]-isobutyramide (1.00 g, 3.38 mmol) in xylene (3 mL) and add α,α-diphenyl-4-piperidinemethanol (1.09 g, 4.07 mmol) and potassium hydrogen carbonate (0.68 g, 6.76 mmol) in water (2.5 mL). Heat at 100° C. for 20 hours, remove hot water by pipette, dilute with ethyl acetate (20 mL) and wash with water (20 mL). Cool the organic layer to room temperature, dry ($MgSO_4$), evaporate the solvent in vacuo and purify by silica gel chromatography (9:1 ethyl acetate/methanol) and recrystallize (ethyl acetate/hexane) to give the title compound (1.13 g, 63%) as a crystalline solid; mp 135–137° C.

EXAMPLE 51

Step c: N,N-Dimethyl-2-(4-{1-hydroxy-4-[4-hydroxy-diphenylmethyl)-piperidin-1-yl]-butyryl}-phenyl)-isobutyramide Dissolve N,N-dimethyl-2-(4-{4-[4-hydroxy-diphenylmethyl)-piperidin-1-yl]-butyryl}-phenyl)-isobutyramide (3.00 g, 5.69 mmol) in ethanol (30 mL), cool using an ice/water bath and add sodium borohydride (0.87 g, 23.04 mmol) in tetrahydrofuran (10 mL). Remove the cold bath and stir at room temperature for 2.5 hours. Add water (25 mL) and ethyl acetate (25 mL) and separate the layers. Extract the aqueous layer with ethyl acetate (20 mL), dry ($MgSO_4$) and evaporate the solvent in vacuo to give the title compound (3.06 g, 100%) as a white foam; mp 166–169° C.

MS (CI, $CH_4$) m/e 529 ($M^+$+1), 280, 183.

Anal. Calcd for $C_{34}H_{44}N_2O_3 \cdot 0.3H_2O$: C, 77.24; H, 8.39; N, 5.30; Found: C, 76.99; H, 8.36; N. 5.17.

EXAMPLE 52

Step a: N-Methoxy-N-methyl-2-(4-{4-[4-hydroxy-diphenylmethyl)-piperidin-1-yl]-butyryl}-phenyl)-isobutyramide Dissolve N-methoxy-N-methyl-2-[4-(4-chlorobutyryl)-phenyl]-isobutyramide (1.44 g, 4.62 mmol) in 2:1 xylene/water (5 mL) and add α,α-diphenyl-4-piperidinemethanol (1.36 g, 5.07 mmol) and potassium hydrogen carbonate (0.93 g, 9.24 mmol). Heat at 108° C. for 22 hours, remove hot water by pipette, cool to room temperature and stir for 2 days. Evaporate the solvent in vacuo and purify by silica gel chromatography (10:1 ethyl acetate/methanol) and recrystallize (ethyl acetate) to give the title compound (1.77 g, 71%) as a white crystalline solid; mp 159–160.5° C.

MS (CI, $CH_4$) m/e 543 ($M^+$+1), 293, 250, 183.

Anal. Calcd for $C_{34}H_{42}N_2O_4 \cdot 0.3H_2O$: C, 74.50; H, 7.83; N, 5.11; Found: C, 74.75; H, 7.96; N, 5.15.

EXAMPLE 53

Step c: N-Methoxy-N-methyl-2-(4-{1-hydroxy-4-[4-hydroxy-diphenylmethyl)-piperidine-1-yl]-butyryl}-phenyl)-isobutyramide Dissolve N-methoxy-N-methyl-2-(4-{4-[4-hydroxy-diphenylmethyl)-piperidin-1-yl]-butyryl}-phenyl)- isobutyramide (8.83 g, 16.27 mmol) in 3.5:1 methanol/tetrahydrofuran (85 mL). Add sodium borohydride (0.62 g, 16.27 mmol) in 8 portions over 20 minutes at room temperature. Stir at room temperature for 2 hours, evaporate the solvent in vacuo, dissolve the residue in ethyl acetate (60 mL) and add water (25m). Stir at room temperature for 10 minutes, separate the layers and wash the organic layer with brine (2×25 mL). Combine the organic layers, extract with ethyl acetate (35 mL), dry ($Na_2SO_4$), evaporate the solvent in vacuo and dry to give the title compound (8.89 g, 100%) as a foam; mp 80–83° C.

MS (CI, $CH_4$) m/e 545 ($M^+$+1), 280, 236, 183.

Anal. Calcd for $C_{34}H_{44}N_2O_4·0.2H_2O$: C, 74.47; H, 8.16; N, 5.12; Found: C, 74.08; H, 8.16; N, 4.93.

EXAMPLE 54

Step a: 1-]4-(1,1-Dimethyl-2-oxo-2-pyrrolidin-1-yl-ethyl)-phenyl]-4-[4-hydroxy-diphenylmethyl)-piperidine-1-yl]-butan-1-one Dissolve 4-chloro-1-[4-(1,1-dimethyl-2-oxo-2-pyrrolidin-1-yl-ethyl)-phenyl]-butan-1-one (6.88 g, 21.38 mmol) in xylene (14 mL) and add a suspension of α,α-diphenyl-4-piperidinemethanol hydrochloride (6.50 g, 23.51 mmol) and potassium carbonate (6.14 g, 4.44 mmol) in water (30 mL). Heat at 100° C. for 24 hours, cool to room temperature, add methylene chloride (100 mL) and separate the layers. Extract the aqueous layer with methylene chloride (100 mL), wash with water (150 mL), dry ($Na_2SO_4$), evaporate the solvent in vacuo and purify by silica gel chromatography (4:1 ethyl acetate/methanol) to give the title compound (8.20 g, 70%) as an off-white solid.

Anal. Calcd for $C_{36}H_{44}N_2O_3·2H_2O$: C, 77.72; H, 8.04; N, 5.08; Found: C, 77.38; H, 7.91; N, 4.93.

EXAMPLE 55

Step c: 2-(4-{1-Hydroxy-4-[4-hydroxydiphenylmethyl)-piperidin-1-yl]-butyl}-phenyl)-2-methyl-1-pyrrolidin-1-yl-propan-1-one Dissolve 1-[4-(1,1-dimethyl-2-oxo-2-pyrrolidin-1-yl-ethyl)-phenyl]-4-[4-hydroxy-diphenylmethyl)-piperidine-1-yl]-butan-1-one (0.55 g, 1.00 mmol) in methanol (10 mL) and add sodium borohydride (38 mg, 1.00 mmol) at 10° C. Stir at room temperature for 2 hours, evaporate the solvent in vacuo and dissolve the residue in methylene chloride (60 mL). Add water (10 mL) and stir for 10 minutes. Separate the layers, wash with brine (5 mL), dry ($Na_2SO_4$) and evaporate the solvent in vacuo to give the title compound (0.53 g, 96%) as a white foam; mp 87–93° C.

EXAMPLE 56

Step a: 4-[4-[4-(Hydroxydiphenylmethyl)-1-piperidinyl]-1-oxobutyl]-α,α-dimethylbenzeneacetic Acid, Ethyl Ester Hydrochloride Dissolve 2-[4-(4-chloro-butyryl)-phenyl]-2-methyl-propionic acid, ethyl ester (15.0 g, 49.53 mmol) and α,α-diphenyl-4-piperidinemethanol (29.669, 106.4 mmol) in xylene (60 mL). Reflux for 5.5 hours, cool in an ice bath, filter and wash with cold xylenes (25 mL). Filter the filtrate though silica gel (20 g) and wash the gel with xylenes (40 mL). Add xylene (60 mL) and concentrated hydrochloric acid (6.45 g, 65.6 mmol) with stirring. Add additional xylenes (40 mL) and stir for 2 hour. Filter, wash with xylene (50 mL), vacuum dry and slurry with a mixture of ethanol (60 mL) and hexane (120 mL) at 70–72° C. for 30 minutes. Filter, wash with 3:1 v/v solution of n-heptane/ethanol (30 mL) and dry to give the title compound as a light white solid (19.7 g, 70%); mp 206–208° C.

$^1$H NMR (300 MHz, $CDCl_3$) δ7.90 (d, J=8.7 Hz, 2H), 7.47 (m, 4H), 7.41 (d, J=8.7 Hz, 2H), 7.27 (m, 4H), 7.15 (m, 4H), 4.10 (q, J=7.1 Hz, 2H), 2.93 (m, 4H), 2.37 (m, 3H), 2.2 (broad s, 1H), 1.92 (m, 4H), 1.59 (s, 6H), 1.39 (m, 4H), 1.16 (t, J=7.1 Hz, 3H); $^{13}$C NMR (75 MHz, $CDCl_3$) δ199.5, 176.1, 149.8, 146.0, 135.5, 128.2, 128.1, 126.4, 125.9, 125.7, 79.4, 61.0, 57.8, 53.9, 46.7, 44.1, 36.3, 26.3, 26.2, 21.9, 14.0; IR ($CDCl_3$) 3514, 2945, 1726, 1682, 1446, 1254, 1147, 1097 $cm^{-1}$;

Anal. Calcd for $C_{34}H_{41}O_4N·HCl$: C, 72.39; H, 7.50; N, 2.48; Found: C, 71.68; H, 7.52; N, 2.34.

EXAMPLE 57

Step a: 4-[4-[4-(Hydroxydiphenylmethyl)-1-piperidinyl]-1-oxobutyl]-α,α-dimethylbenzeneacetic Acid, Methyl Ester Hydrochloride Dissolve 2-[4-(4-chloro-butyryl)-phenyl]-2-methyl-propionic acid, methyl ester (2.82 g, 10.0 mmol) and α,α-diphenyl-4-piperidinemethanol (5.58 g, 21.0 mmol) in toluene (20 mL). Reflux for 29 hours, cool in an ice bath, filter, filter the filtrate though silica gel (5 g) and wash the gel with toluene (10 mL). Evaporate the solvent in vacuo and dissolve the residue in ethyl ether (100 mL). Add anhydrous hydrogen chloride and filter to give the title compound as an off-white powder (4.2 g, 76%); mp 165–175° C.

$^1$ NMR (300 MHz, $CDCl_3$) δ7.93 (d, J=8.3 Hz, 2H), 7.47 (m, 4H), 7.42 (d, J=8.3 Hz, 2H), 7.30 (m, 4H), 7.18 (m, 2H), 3.64 (s, 3H), 2.96 (m, 4H), 2.42 (m, 4H), 1.96 (m, 4H), 1.62 (s, 6H), 1.41 (m, 4H); $^{13}$C NMR (75 MHz, $CDCl_3$) δ199.1, 176.3, 149.4, 145.8, 135.5, 128.1, 128.0, 127.7, 126.3, 125.7, 1225.6, 79.4, 57.9, 54.0, 52.4, 46.9, 44.1, 36.4, 26.4, 26.3, 22; MS ($CI/NH_3$) 514 (100 (M+H)), 293 (4), 268 (7).

Anal. Calcd for $C_{33}H_{39}O_4N·HCl$: C, 72.05; H, 7.33; N, 2.55; Found: C, 71.85; H, 7.23; N, 2.33.

EXAMPLE 58

Step c: 4-[4-[4-(Hydroxydiphenylmethyl)-1-piperidinyl]-1-hydroxybutyl]-α,α-dimethylbenzeneacetic Acid, Methyl Ester Hydrochloride Dissolve 4-[4-[4-(hydroxydiphenylmethyl)-1-piperidinyl]-1-oxobutyl]-α,α-dimethylbenzeneacetic acid, methyl ester hydrochloride (550 mg, 1.00 mmol) in methanol (5 mL) and add sodium borohydride (62.8 mg) in three batches. Stir for 1 hour, add 50% aqueous sodium hydroxide (800 mg) and heat to reflux with stirring. After 3 hours, cool to −10° C., add approximately 1.5 mL of 6N HCl over 10 minutes, filter the solid and wash with ice water (12 mL) such that the final filtrate is pH=5. Dry the resulting solid in vacuo (50–60° C., $10^{-1}$ mm) overnight to give the title compound (515 mg, 94%); mp 165–180° C.

$^1$H NMR (300 MHz, 5% $MeOD_4$ in $CDCl_3$) δ7.50 (d, J=7.3 Hz, 4H), 7.30 (m, 8H), 7.18 (t, J=7.0 Hz, 2H), 4.66 (t, J=5.3 Hz, 1H), 3.47 (m, 6H), 2.97 (m, 2H), 2.69 (m, 3H), 1.6–2.2 (m, 6H), 1.55 (s, 6H); $^{13}$C NMR (75 MHz, 5% $MeOD_4$ in $CDCl_3$) δ179.1, 145.3, 143.8, 142.3, 128.2, 126.6, 125.7, 125.5, 125.4, 78.4 (bis benzylic), 72.5 (benzylic), 57.4, 53.2, 46.2, 24.2, 35.9, 26.6, 24.1, 20.8: MS ($CI/NH_3$) 502 (100 (M+H)), 280 (5), 200 (10).

EXAMPLE 59

Step c: 2-(4-(1-Hydroxy-4-(4-(hydroxydiphenylmethyl)-1-piperidinyl)-butyl)-phenyl)-2-methyl-propanol Dissolve 2-(4-(1-oxo-4-(4-(hydroxydiphenylmethyl)-1-piperidinyl)-butyl)-phenyl)-2-methylpropanol in methanol (450 mL) and stir for 15 minutes at room temperature. Add, by dropwise addition, a solution of sodium borohydride (2.25 g, 0.06 mol) in water (10 mL) over 15 minutes. Stir for another 30 minutes and cool in an ice-bath. Slowly add concentrated hydrochloric acid (4 mL) and water (8 mL) and stir for an additional 20 minutes. Evaporate the solvent in vacuo and partition the residue between methylene chloride (150 mL) and water (70 mL). Separate the organic phase and extract the aqueous phase with methylene chloride (25 mL). Wash the combined organic layers with water (2×50 mL), evaporate the solvent in vacuo and recrystallize (acetone) to give the title compound as white needles (9.53 g, 79%).

$^1$H NMR (300 MHz, DMSO-$d_6$) δ7.50 (4H, m), 7.23 (8H, m), 7.12 (2H, m), 5.34 (1H, s, br), 4.65 (1H, t), 4.45 (1H, s), 3.38 (2H, t), 2.60 (2H, m), 2.44 (2H, m), 2.20 (2H, t), 1.62 (2H, t), 1.50 (6H, m), 1.98 (6H, S); $^{13}$C NMR (DMSO-$d_6$) δ147.2, 146.0, 143.4, 127.6, 125.6, 125.5, 125.2, 78.4, 72.0, 70.9, 58.0, 53.6, 53.5, 43.6, 38.0, 30.5, 25.9, 25.5, 23.1.

Alternatively, the novel intermediates of formula (XI) may be prepared as described in Scheme M. In Scheme M, all substituents are as previously defined unless otherwise indicated.

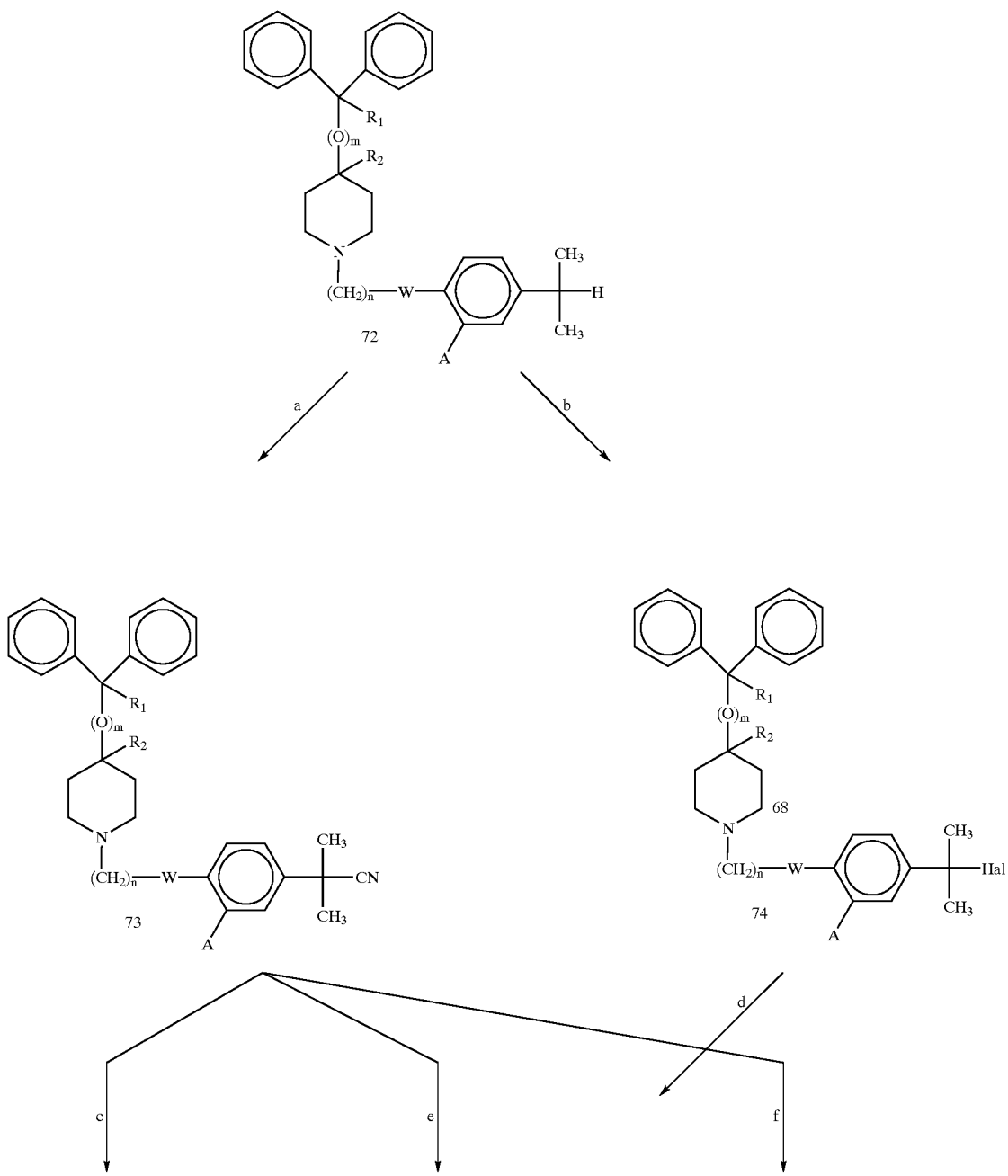

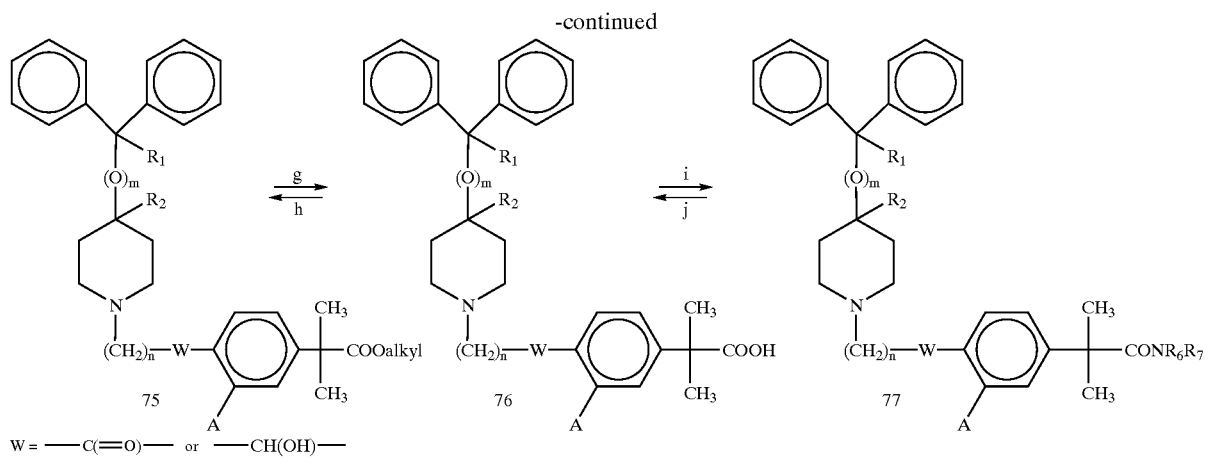

W = —C(=O)— or —CH(OH)—

Scheme M provides various alternative general synthetic procedures for preparing the novel intermediates of formula (XI).

In step a, the appropriate ω'-piperidine-2-methylethylphenyl compound of structure (72) is cyanated to give the corresponding ω'-piperidine-α,α-dimethylphenylacetonitrile compound of structure (73) as described previously in Scheme D, step b.

In step b, the appropriate ω'-piperidine-2-methylethylphenyl compound of structure (72) is halogenated to give the corresponding ω'-piperidine-α,α-dimethylbenzyl halide compound of structure (74) as described previously in Scheme B, step a.

In step c, the nitrile functionality of the appropriate ω'-piperidine-α,α-dimethylphenylacetonitrile compound of structure (73) is converted to the corresponding ester to give the ω'-piperidine-α,α-dimethylphenylacetic acid ester compound of structure (75) as described previously in Scheme H step a.

In step d, the halo functionality of the appropriate ω'-piperidine-α,α-dimethylbenzyl halide compound of structure (74) is converted to the corresponding carboxy to give the ω'-piperidine-α,α-dimethylphenylacetic acid compound of structure (76) as described previously in Scheme H, step h.

In step e, the nitrile functionality of the appropriate ω'-piperidine-α,α-dimethylphenylacetonitrile compound of structure (73) is converted to the corresponding carboxy to give the ω'-piperidine-α,α-dimethylphenylacetic acid compound of structure (76) as described previously in Scheme H, step e.

In step f, the nitrile functionality of the appropriate ω'-piperidine-α,α-dimethylphenylacetonitrile compound of structure (73) is converted to the corresponding amide to give the ω'-piperidine-α,α-dimethylphenylacetic acid amide compound of structure (77) wherein $R_6$ and $R_7$ are each hydrogen as described previously in Scheme H, step b.

In step g, the carboxy ester functionality of the appropriate ω'-piperidine-α,α-dimethylphenylacetic acid ester compound of structure (75) is hydrolyzed to give the corresponding ω'-piperidine-α,α-dimethylphenylacetic acid compound of structure (76) as described previously in Scheme H, step c.

In step h, the carboxy functionality of the appropriate ω'-piperidine-α,α-dimethylphenylacetic acid compound of structure (76) may be esterified by techniques and procedures well known and appreciated by one of ordinary skill in the art to give the corresponding ω'-piperidine-α,α-dimethylphenylacetic acid ester compound of structure (75) as described previously in Scheme H, step d.

In step i, the carboxy functionality of the appropriate ω'-piperidine-α,α-dimethylphenylacetic acid compound of structure (76) may be amidated by techniques and procedures well known and appreciated by one of ordinary skill in the art to give the corresponding ω'-piperidine-α,α-dimethylphenylacetic acid amide compound of structure (77) as described previously in Scheme H, step g.

In step j, the amide functionality of the appropriate ω'-piperidine-α,α-dimethylphenylacetic acid amide compound of structure (77) is converted to the corresponding acid by acid hydrolysis as is known in the art to give the ω'-piperidine-α,α-dimethylphenylacetic acid compound of structure (76) as described previously in Scheme H, step f.

Starting materials for use in Scheme M are readily available to one of ordinary skill in the art.

The following examples present typical syntheses as described in Scheme M. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "°C." refers to degrees Celsius; "mm Hg" refers to millimeters of mercury; "μL" refers to microliters; "μg" refers to micrograms; and "μM" refers to micromolar.

EXAMPLE 60

Step q: 4-[4-[4-(Hydroxydiphenylmethyl)-1-piperidinyl]-1-oxobutyl]-α,α-dimethylbenzeneacetic Acid Hydrochloride Dissolve 4-[4-[4-(hydroxydiphenylmethyl)-1-piperidinyl]-1-oxobutyl]-α,α-dimethylbenzeneacetic acid methyl ester (0.131 mol) in methanol (2.5 L) and add 10% sodium hydroxide (769 mL, 1.92 mol). Stir at reflux for 1.5 hours, cool to 68° C. and evaporate the solvent in vacuo to a residue. Add chloroform (1 L) and stir until the solids are dissolved. Separate the organic phase and extract the aqueous phase with chloroform (3×300 mL). Combine the organic phases, dry (MgSO$_4$) and evaporate the solvent in vacuo to give a residue. Treat the residue with ethereal HCl, filter and dry to give the title compound.

EXAMPLE 61

Step j: 4-[4-[4-(Hydroxydiphenylmethyl)-1-piperidinyl]-1-hydroxybutyl]-α,α-dimethylbenzeneacetic Acid Dissolve N-methoxy-N-methyl-2-(4-{1-hydroxy-4-[4-hydroxy-diphenylmethyl)-piperidine-1-yl]-butyryl}- phenyl)-isobutyramide (8.35 g, 15.33 mmol) in isopropanol (50 mL) and add potassium hydroxide (8.63 g, 153.7 mmol). Heat to reflux for 2 hours, add additional potassium hydroxide (4.35 g, 77.5 mmol) and heat at reflux for an additional 16 hours. Cool to room temperature, treat with concentrated HCl by dropwise addition until pH=3. Dilute with water (100 mL), stir vigorously for 2 hours, add ethyl acetate (30 mL) and stir for 1 hour. Filter to give the title compound (7.15 g, 87%) as an off-white solid.

MS (CI, $CH_4$) m/e 502 ($M^+$+1), 107.

Anal. Calcd for $C_{32}H_{39}NO_4 \cdot HCl \cdot 2.6H_2O$: C, 65.70; H, 7.61; N, 2.39; Found: C, 65.25; H, 7.70; N, 2.36.

EXAMPLE 62

Step j: 4-[4-[4-(Hydroxydiphenylmethyl)-1-piperidinyl]-1-hydroxybutyl]-α,α-dimethylbenzeneacetic Acid Dissolve N,N-dimethyl-2-(4-{1-hydroxy-4-[4-hydroxydiphenylmethyl)-piperidin-1-yl]-butyryl}-phenyl)-isobutyramide (15.33 mmol) in isopropanol (50 mL) and add potassium hydroxide (8.63 g, 153.7 mmol). Heat to reflux for 2 hours, add additional potassium hydroxide (4.35 g, 77.5 mmol) and heat at reflux for an additional 16 hours. Cool to room temperature, treat with concentrated HCl by dropwise addition until pH=3. Dilute with water (100 mL), stir vigorously for 2 hours, add ethyl acetate (30 mL) and stir for 1 hour. Filter to give the title compound (41%).

As one skilled in the art would appreciate, the compounds depicted in Schemes A through M which bear hydroxy or phenolic functionalities may be protected prior to use in the synthesis depicted in Schemes A through M using suitable protecting groups. For example, suitable protecting groups for the phenolic hydroxy include methyl ether, 2-methoxyethoxymethyl ether (MEM), cyclohexyl ether, o-nitrobenzyl ether, 9-anthryl ether, t-butyldimethylsilyl ether, acetate, benzoate, methyl carbamate, benzyl carbamate, aryl pivaloate and aryl methanesulfonate.

As one skilled in the art would appreciate, the compounds depicted in Schemes A through M which bear α-ketone functionalities may be protected prior to use in the synthesis depicted in Schemes A through M using suitable protecting groups. The selection and utilization of suitable protecting groups for ketone groups is well known by one of ordinary skill in the art and is described in "Protective Groups in Organic Syntheses", Theodora W. Greene, Wiley (1981). For example, suitable protecting groups for ketone functionalities include acyclic acetals and ketals such as dimethyl acetal, cyclic acetals and ketals such as 1,3-dioxanes and 1,3-dioxolanes, dithio acetals and ketals such as 1,3-dithiane and 1,3-dithiolane, hemithio acetals and ketals, O-substituted cyanohydrins, substituted hydrozones, imines, oxazolidines, imidazolidines and thiazolidines.

As one skilled in the art would appreciate, the compounds depicted in Schemes A through M which bear protected hydroxy and/or ketone functionalities may be reacting with appropriate deprotecting agents prior to use in any of the steps depicted in Schemes A through M. The selection and utilization of appropriate deprotecting reagents is well known by one of ordinary skill in the art and is described in "Protective Groups in Organic Syntheses", Theodora W. Greene, Wiley (1981). Examples of appropriate deprotecting reagents are mineral acids, strong organic acids, Lewis acids, aqueous mineral bases, catalytic hydrogenation and the like.

For example, cleavage of β-methoxyethoxymethyl (MEM) protecting groups on any of the compounds depicted in Schemes A through M which bear protected hydroxy ketone functionalities, for example, can be achieved by using trifluoroacetic acid at room temperature or using 5 to 8 equivalents of powdered anhydrous zinc bromide in methylene chloride at about 25° C. by the general procedure of E. J. Corey et al., *Tetrahedron Letters*, 11, 809–812 1976.

In addition, the individual (R) and (S) isomers of the ω'-piperidine-α'-hydroxy-α,α-dimethylphenyl compounds of structure (71) can be prepared by techniques are procedures well known and appreciated by one of ordinary skill in the art.

For example, the mixture of (R) and (S) isomers of the ω'-piperidine-α'-hydroxy-α,α-dimethylphenyl compounds of structure (71) may be subjected to chiral chromatography to give the corresponding individual (R)-ω'-piperidine-α'-hydroxy-α,α-dimethylphenyl compounds of structure (71) and (S)-ω'-piperidine-α'-hydroxy-α,α-dimethylphenyl compounds of structure (71).

In addition, the individual (R) and (S) isomers of the ω-halo-α'-hydroxy-α,α-dimethylphenyl compound of structure (70) and the ω'-piperidine-α'-hydroxy-α,α-dimethylphenyl compounds of structure (71) can be prepared by techniques and procedures well known and appreciated by one of ordinary skill in the art and described in "Enanatiomers, Racemates, and Resolutions", Jacques, Collet and Wilen, Wiley (1981).

One such method involves reacting the mixture of (R) and (S) isomers of the ω'-piperidine-α'-hydroxy-α,α-dimethylphenyl compounds of structure (71) with appropriate chiral acids to give the corresponding mixture of diastereomeric acid addition salts. The individual (R)-ω'-piperidine-α'-hydroxy-α,α-dimethylphenyl chiral acid addition salt compounds of structure (71) and (S)-ω'-piperidine-α'-hydroxy-α,α-dimethylphenyl chiral acid addition salt compounds of structure (71) are obtained by recrystallization and the individual ω'-piperidine-(R)-α'-hydroxy-α,α-dimethylphenyl compounds of structure (71) and ω'-piperidine-(S)-α'-hydroxy-α,α-dimethylphenyl compounds of structure (71) are obtained by subjecting the individual ω'-piperidine-(R)-α'-hydroxy-α,α-dimethylphenyl chiral acid addition salt compounds of structure (71) and ω'-piperidine-(S)-α'-hydroxy-α,α-dimethylphenyl chiral acid addition salt compounds of structure (71) to base in order to free the piperidine nitrogen from the acid addition complex. Examples of suitable chiral acids are tartaric acid (+), (−), O,O'-dibenzoyltartaric acid (+), (−), OO'-di-p-toluyltartaric acid (+), (−), 2-Nitrotartranillic acid (+), (−), mandelic acid (+), (−), malic acid (+), (−), 2-phenoxypropionic acid (+), hydratropic acid (+), (−), N-acetylleucine (−), (+), N-(α-methylbenzyl) succinamide (+), (−), N-(α-methylbenzyl)phthalamic acid (+), (−), camphor-10-sulfonic acid (+), 3-bromocamphor-9-sulfonic acid (+), (−), camphor-3-sulfonic acid (+), quinic acid (+), (−), Di-O-isopropylidene-2-oxo-L-gulonic acid (−), Lasalocid (−), 1,1'-binaphthyl-2,2'-phosphoric acid (+), (−), chloestenonesulfonic acid.

In addition, the individual (R) and (S) isomers of the ω'-piperidine-α'-hydroxy-α,α-dimethylphenyl compounds of structure (71) can be prepared by reacting the mixture of (R) and (S) isomers of the ω'-piperidine-α'-hydroxy-α,α-dimethylphenyl compounds of structure (71) with appropriate organic chiral acids to give the corresponding mixture of diastereomeric acid esters. The individual ω'-piperidine-(R)-α'-ester-α,α-dimethylphenyl compounds of structure (71) and ω'-piperidine-(S)-α'-ester-α,α-dimethylphenyl compounds of structure (71) are obtained by recrystallization or chromatography and the individual ω'-piperidine-(R)-α'-hydroxy-α,α-dimethylphenyl compounds of structure (71) and ω'-piperidine-(S)-α'-hydroxy-α,α-dimethylphenyl compounds of structure (71) are obtained by subjecting the individual ω'-piperidine-(R)-α'-ester-α,α-dimethylphenyl compounds of structure (71) and ω'-piperidine-(S)-α'-ester- α,α-dimethylphenyl compounds of structure (71) to hydrolysis conditions.

What is claimed is:

1. A process for preparing a compound of the formula

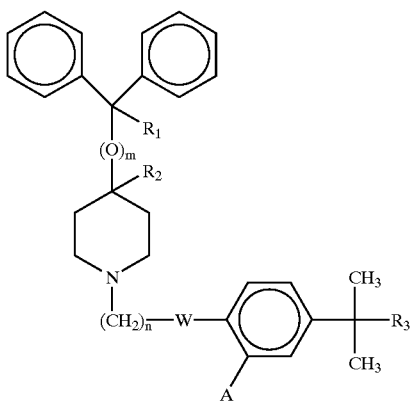

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_3$ is —COOH or —COOalkyl wherein the alkyl moiety has from 1 to 6 carbon atoms and is straight or branched;

each of A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represented hydroxy, m is an integer 0 comprising converting into said compound, an intermediate compound of the formula

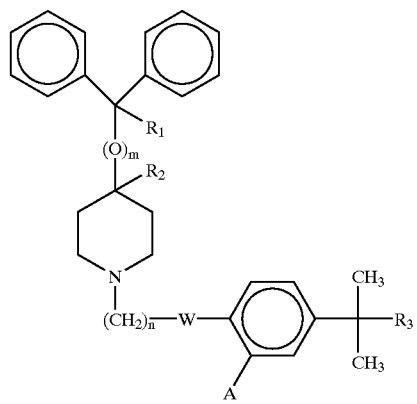

wherein

W represents —C(=O)— or —CH(OH)—;

$R_1$ represents hydrogen or hydroxy;

$R_2$ represents hydrogen; or $R_1$ and $R_2$ taken together form a second bond between the carbon atoms bearing $R_1$ and $R_2$;

n is an integer of from 1 to 5;

m is an integer 0 or 1;

$R_5$ is H, Br, Cl, I, CN or —CONR$_6$R$_7$ wherein one of $R_6$ and $R_7$ is $C_{1-C_6}$alkoxy and the other $R_6$ or $R_7$ is selected from H or $C_1$–$C_6$alkoxy;

A is hydrogen or hydroxy; and pharmaceutically acceptable salts and individual optical isomers thereof, with the proviso that where $R_1$ and $R_2$ are taken together to form a second bond between the carbon atoms bearing $R_1$ and $R_2$ or where $R_1$ represents hydroxy, m is an integer 0.

2. The process of claim 1 wherein $R_1$ is hydroxy; $R_2$ is hydrogen; m is zero; n is 3; W is —CH(OH)—; A is hydrogen; and $R_3$ is —COOH.

* * * * *